US009234044B2

(12) United States Patent
Matsushima et al.

(10) Patent No.: US 9,234,044 B2
(45) Date of Patent: Jan. 12, 2016

(54) AGONISTIC ANTI-CD40 IGG2 ANTIBODIES HAVING AMINO ACID MUTATIONS INTRODUCED THEREIN

(75) Inventors: Aki Matsushima, Shizuoka (JP);
Hiroshi Namisaki, Tokyo (JP);
Shigenori Yagi, Ibaraki (JP)

(73) Assignee: KYOWA HAKKO KIRIN CO., LTD, Tokyo (JP)

( * ) Notice: Subject to any disclaimer, the term of this patent is extended or adjusted under 35 U.S.C. 154(b) by 0 days.

(21) Appl. No.: 13/265,075

(22) PCT Filed: Apr. 20, 2010

(86) PCT No.: PCT/JP2010/057027
§ 371 (c)(1),
(2), (4) Date: Dec. 15, 2011

(87) PCT Pub. No.: WO2010/123012
PCT Pub. Date: Oct. 28, 2010

(65) Prior Publication Data
US 2012/0087927 A1    Apr. 12, 2012

Related U.S. Application Data

(60) Provisional application No. 61/170,738, filed on Apr. 20, 2009.

(51) Int. Cl.
*A61K 39/395* (2006.01)
*C07K 16/28* (2006.01)
*C12R 1/91* (2006.01)
*A61K 39/00* (2006.01)

(52) U.S. Cl.
CPC .............. *C07K 16/2878* (2013.01); *C12R 1/91* (2013.01); *A61K 2039/505* (2013.01); *C07K 2317/52* (2013.01); *C07K 2317/72* (2013.01); *C07K 2317/73* (2013.01); *C07K 2317/75* (2013.01); *C07K 2317/94* (2013.01)

(58) Field of Classification Search
None
See application file for complete search history.

(56) References Cited

U.S. PATENT DOCUMENTS

| 7,247,302 B1 * | 7/2007 | Rosok et al. ............... 424/133.1 |
| 2007/0148163 A1 * | 6/2007 | Takahashi et al. ......... 424/131.1 |
| 2010/0068145 A1 * | 3/2010 | Langer et al. .................. 424/9.1 |

FOREIGN PATENT DOCUMENTS

| JP | 2005-508176 A | 3/2005 |
| JP | 2007-525171 A | 9/2007 |
| WO | 03/040170 A2 | 5/2003 |
| WO | 2005063981 A1 | 7/2005 |

OTHER PUBLICATIONS

Written Opinion of the International Searching Authority for PCT/JP2010/057027 (English Translation) (mailed Jun. 8, 2010).*
Intellectual Property Office of New Zealand, Office Action Issued Apr. 13, 2012, in counterpart New Zealand Application No. 595825.
Intellectual Property Office of New Zealand, Office Action dated Jul. 19, 2012 issued in counterpart New Zealand Application No. 595825.
International Searching Authority, Written Opinion issued in corresponding International Patent Application No. PCT/JP2010/057027 on Jun. 8, 2010.
Martin J. Glennie et al., "Clinical trials of antibody therapy", Immunology Today, 2000, 21(8): 403-410.
Kiminori Kimura et al., "Pathogenic Role of B Cells in Anti-CD40-Induced Necroinflammatory Liver Disease", American Journal of Pathology, 2006, 168(3): 786-795.
Xuhui Zhou et al., "The Role of Complement in the Mechanism of Action of Rituximab for B-Cell Lymphoma: Implications for Therapy", The Oncologist, 2008, 13:1-13.
European Patent Office, Extended European Search Report, dated Apr. 8, 2013, issued in counterpart European Application No. 10767069.7.
Cole, M.S. et al: "Human IgG2 Variants of Chimeric Anti-CD3 are Nonmitogenic to T cells", The Journal of Immunology, The American Association of Immunologists, US, vol. 159, No. 7, Oct. 1, 1997, pp. 361303621, XP002226664, ISSN: 0022-1767.
European Patent Office, Communication dated Mar. 21, 2014, issued in counterpart European Patent Application No. 10 767 069.7.
Ozer et al., "The current state of serum biomarkers of hepatotoxicity", Toxicology, 2008, 245:194-205.
Notification of Reasons for Refusal, dated Aug. 26, 2014, issued by the Japanese Patent Office in counterpart Japanese Patent Application No. 2011-510330.

* cited by examiner

*Primary Examiner* — Phillip Gambel
(74) *Attorney, Agent, or Firm* — Sughrue Mion, PLLC

(57) ABSTRACT

The present invention can provide a monoclonal antibody which comprises a heavy chain constant region which is IgG2 wherein valine at position 234, glutamine at position 237 and proline at position 331 are at least substituted with alanine, alanine and serine, respectively (numbering is based on the EU index of Kabat et al); has an agonist activity; and binds to human CD40.

10 Claims, 7 Drawing Sheets

AGONISTIC ANTI-CD40 IGG2 ANTIBODIES HAVING AMINO ACID MUTATIONS INTRODUCED THEREIN

This is a 371 National Stage Entry of International Patent Application No. PCT/JP2010/057027, filed Apr. 20, 2010, which claims priority to Provisional Patent Application No. 61/170,738, filed Apr. 20, 2009, the contents of which are hereby incorporated by reference in their entirety.

TECHNICAL FIELD

The present invention relates to a monoclonal antibody which binds to human CD40, comprises a heavy chain constant region which is IgG2 in which valine at position 234, glycine at position 237 and proline at position 331 are at least substituted with alanine, alanine and serine, respectively, (numbering is based on the EU index of Kabat et al.), and has an agonist activity; a DNA which encodes the monoclonal antibody; a vector which comprises the DNA; a transformant obtainable by introducing the vector; a process for producing the monoclonal antibody using the transformant; and a pharmaceutical composition and a therapeutic agent comprising the monoclonal antibody.

BACKGROUND OF THE INVENTION

1. CD40

CD40 is an antigen which has a molecular weight of 50 kDa and is present on the surface of cell membrane, and expressed in B cells, dendritic cells (DCs), some types of cancer cells, and thymic epithelial cells. CD40 is known to play an important role in proliferation and differentiation of B cells and DCs. CD40 was identified as an antigen expressed on the surface of human B cells (Non-Patent Documents 1 and 2) and has been considered as a member of the TNF receptor family to which low-affinity NGF receptors, TNF receptors, CD27, OX40, CD30 and the like belongs. A ligand (CD40L) to human and murine CD40s has been found to be a type II membrane proteins expressed in activated CD4+ T cells. CD40L has been also found to introduce strong signals for activation into human or murine B cells.

It is considered that the expression of CD40 in DC is higher than that in B cell and it has become clear that CD40 plays an important role. Binding of CD40 to CD40L activates an antigen presenting cell (APC). Namely, it activates the expression of costimulator molecules such as CD80 (B7-1) and CD86 (B7-2) or enhances the production of IL-2 (Non-Patent Documents 3 and 4). DC has a strong antigen-presenting activity and a strong capacity to activate helper T (Th) cells. DC is also considered to control differentiation of naive Th cells into Th1 or Th2 cells. When peripheral blood monocytes which are myeloid dendritic cells are cultured in the presence of GM-CSF and IL-4, and matured by CD40L, the resulting matured dendritic cells (DC1) can produce IL-12 in vitro, and stimulate and activate allogeneic naive Th cells to induce IFNγ-producing T cells (i.e., to promote their differentiation into Th1). This function is inhibited by anti-IL-12 antibody and hence may be a reaction mediated by IL-12. On the other hand, when plasmacytoid T cells which are present in lymphoid T regions and peripheral blood are cultured in the presence of IL-3 and CD40L, the resulting lymphoid dendritic cells (DC2) are shown to be unable to produce IL-12, and stimulate and activate allogeneic naive Th cells to induce IL-4-producing T cells, which indicates promotion of their differentiation into Th2. It is considered that Th1 cells are involved in activation of cellular immunity, while Th2 cells are associated with enhancement of humoral immunity as well as restriction of cellular immunity. When cytotoxic T cells (CTL) are activated with the help of Th1 cells, they may eliminate pathogens (various virus, *listeria*, tuberculosis bacteria, *toxoplasma* protozoa, etc.) growing in the cytoplasm and tumor cells.

The monoclonal anti-CD40 antibody which recognizes CD40 expressed on the membrane surface has been demonstrated to have different biological activities to B cells. The monoclonal anti-CD40 antibody is generally classified into agonistic substance (antagonistic antibody) or antagonistic substance (antagonistic antibody) against CD40.

2. Agonistic Antibodies

As function of an agonistic antibody, the activation of B cells is known. For example, the anti-CD40 antibody has been reported to induce cell adhesion (Non-Patent Documents 5 and 6), increase cell size (Non-Patent Documents 6 and 7), induce cell division of B cells activated only by an anti-IgM antibody, anti-CD20 antibody or phorbol ester (Non-Patent Documents 8 to 10), induce cell division of B cells in the presence of IL-4 (Non-Patent Documents 7 and 11), induce expression of IgE by cultured cells stimulated with IL-4 and deprived of T cells (Non-Patent Documents 12 and 13), induce expression of IgG and IgM by those cultured cells (Non-Patent Documents 13), secrete soluble CD23/FceRII from cells due to IL-4 (Non-Patent Documents 14 and 15), enhance expression of soluble CD23/FceRII on the cells due to IL-4 (Non-Patent Documents 16), and promote IL-6 production (Non-Patent Document 17).

Furthermore, it has been reported that addition of IL-4 and an anti-CD40 antibody to human primary culture B cells in the presence of CDw32+ adhesive cells led to establishment of cloned B cells derived therefrom (Non-Patent Document 18), and apoptosis of germinal center cells was inhibited by CD40 regardless of whether its antigen receptor was active or inactive (Non-Patent Document 19). As described above, since CD40 has been identified as antigen expressed on the surface of human B cells, most of the isolated antibodies have been mainly evaluated by their induction potency for proliferation and/or differentiation of human B cells or their induction activity for cell death of cancer cells, as an index (Non-Patent Documents 20, 21 and 22).

In addition, the anti-CD40 antibody has been demonstrated to mature DC (Non-Patent Document 23). Furthermore, the role of CD4 T cells in priming antigen-specific CD8 T cells has been reported to be the activation of DC via CD40-CD40L signaling, and the anti-CD40 monoclonal antibody (mAb) has been found to be able to substitute CD40 helper T cells in activation of DC (Non-Patent Document 24). Also, administration of an anti-CD40 antibody in mice has been found to be able to protect the animal body from CD40-expressing tumor cells as well as CD40-non-expressing tumor cells (Non-Patent Document 25).

An anti-CD40 antibody having an agonist activity is expected to be effective for treatment of infectious diseases due to such as bacteria and virus; malignancy; and the like, based on their functions described above.

As an anti-CD40 antibody having an agonist activity, the antibody KM341-1-19 is disclosed in Patent Document 1. The hybridoma KM341-1-19 producing the antibody KM341-1-19 (Accession Number: FERM BP-7759) was deposited on 27, September 2001 for international deposit under the Budapest Treaty, to International Patent Organisms Depositary, National Institute of Advanced Industrial Science and Technology (central 6, 1-1, Higashi 1, Tsukuba, Ibaraki, Japan). The heavy chain constant region of the antibody KM341-1-19 and the antibody 341G2Ser having a heavy chain constant region which is IgG2 in which proline at position 331 is substituted with serine (this substitution is represented as P331S; hereinafter, represented as the same; numbering is based on the EU index of Non-Patent Document 26) are disclosed in Patent Document 2.

The anti-CD40 antibody 21.4.1 having an agonist activity is disclosed in Patent Document 3.

3. Mutation of Amino Acid

It has been reported that a region at positions 233-299 of a lower hinge region of IgG (numbering is based on the EU index of Kabat et al.) is one of the binding regions to an Fcγ receptor, which is a member of immunoglobulin Fc receptor (Non-Patent Document 27). The immunoglobulin Fc receptor plays an important role in antibody-mediated immune response. Specifically, it includes phagocytosis, ADCC activity (Non-Patent Documents 28 and 29) and the like. The Fcγ receptor is expressed on surfaces of leukocytes, and is divided into three classes of FcγRI (CD64), FcγRII (CD32), and FcγRIII (CD16). Further, FcγRII is subdivided into FcγRIIA and FcγRIIB, and FcγRIII is subdivided into FcγRIIIA and FcγRIIIB.

It has been reported that binding of an Fcγ receptor is lowered by substituting a lower hinge region of IgG1 with IgG2 which is a subclass having a weak effector function activity of an antibody through an Fcγ receptor. Specifically, examples of E233P, L234V, L235A, deletion of G236 and the like (numbering is based on the EU index of Kabat et al. (Non-Patent Documents 30 to 33). As discussed above, it is known that an effector function activity of an antibody through an Fcγ receptor is weak for an antibody having IgG2 as a subclass, and it has been reported that lysis of a target cell by an effector cell can be further inhibited by the substitution of V234A and G237A (numbering is based on the EU index of Kabat et al.) (Non-Patent Document 34). However, the effects of V234A and G237A on the agonist activity of an anti-CD40 antibody are not disclosed. Alternatively, the effects of V234A and G237A in IgG2 subclass on the blood kinetics of an anti-CD40 antibody are not disclosed. Still further, the effects of V234A and G237A in IgG2 subclass of an anti-CD40 antibody on the liver are not disclosed.

For example, L235, D265, D270, K322, P331 and P329 (numbering is based on the EU index of Kabat et al.) have been considered to play an important role in the complement-activating capacity of human IgG and the CDC activity can be reduced by substituting these sites with other amino acids (Non-Patent Documents 35 to 40). Specifically, the reduction in CDC activity can be achieved by substituting D270, K322, P329 and/or P331 with A. Alternatively, the reduction in CDC activity can be achieved by substituting P331 with S or G.

CITATION LIST

Patent Document

Patent Document 1: WO02/088186
Patent Document 2: WO2005/063981
Patent Document 3: WO03/040170

Non-Patent Document

Non-Patent Document 1: E. A. Clark et al., *Proc. Natl. Acad. Sci. USA* 83: 4494, 1986
Non-Patent Document 2: I. Stamenkovic et al., *EMBO J.* 8: 1403, 1989
Non-Patent Document 3: Caux, C., et al., *J. Exp. Med.*, 180: 1263, 1994
Non-Patent Document 4: Shu, U., et al., *Eur J. Immunol.*, 25: 1125, 1995
Non-Patent Document 5: Barrett et al., *J. Immunol.* 146: 1722, 1991
Non-Patent Document 6: Gordon et al., *J Immunol.* 140: 1425, 1998
Non-Patent Document 7: Valle et al., *Eur. J. Immunol.* 19: 1463, 1989
Non-Patent Document 8: Clark and Ledbetter, *Proc. Natl Acad. Sci. USA* 83: 4494, 1986
Non-Patent Document 9: Gordon et al., *LEUCOCYTE TYPING III.* A. J. McMicheal ed. Oxford University Press. Oxford. p. 426
Non-Patent Document 10: Paulie et al., *J. Immunol.* 142: 590, 1989
Non-Patent Document 11: Gordon et al., *Eur J. Immunol.* 17: 1535, 1987
Non-Patent Document 12: Jabara et al., *J. Exp. Med.* 172: 1861, 1990
Non-Patent Document 13: Gascan et al., *J. Immunol.* 147: 8, 1991
Non-Patent Document 14: Gordon and Guy, *Immunol. Today* 8: 39, 1987
Non-Patent Document 15: Cairns et al., *Eur J. Immunol.* 18: 349, 1988
Non-Patent Document 16: Challa, A., *Allergy*, 54: 576, 1999
Non-Patent Document 17: Clark and Shu, *J. Immunol.* 145: 1400, 1990
Non-Patent Document 18: Bancherauet al., *Science* 241: 70, 1991
Non-Patent Document 19: Liu et al., *Nature* 342: 929, 1989
Non-Patent Document 20: Katira, A. et al., *LEUKOCYTE TYPING* V. S. F. Schlossossman, et. al. eds. p. 547. Oxford University Press. Oxford
Non-Patent Document 21: W. C. Flansow et al., *LEUKOCYTE TYPING* V. S. F. Schlossossman, et al. eds. p. 555. Oxford University Press. Oxford
Non-Patent Document 22: J. D. Pound et al., *International Immunology*, 11: 11, 1999
Non-Patent Document 23: Z. H. Zhou et al., *Hybridoma*, 18: 471, 1999
Non-Patent Document 24: Shoenberger, S. P., et al., *Nature*, 480, 1998
Non-Patent Document 25: French, R. R., et al., *Nature Medicine*, 5, 1999
Non-Patent Document 26: Kabat et. al., Sequences of proteins of Immunological Interest, 1991 Fifth edition
Non-Patent Document 27: Duncan, A. R. et al., *Nature* 332: 563
Non-Patent Document 28: Gessner, J. E. et al., *Ann. Hematol.* 1998; 76: 231
Non-Patent Document 29: Da'ron, M. et al., Annu. Rev. Immunol. 1997, 15: 203
Non-Patent Document 30: Wines, B. D. et al., *J. Immunol.* 2000, 164: 5313
Non-Patent Document 31: Lund, J. et al., *Mol. Immunol.* 1992, 29: 53
Non-Patent Document 32: Sarmay. G et al., *Mol. Immunol.* 1992, 29: 633
Non-Patent Document 33: Jefferis, R. et al., *Mol. Immunol.* 1990, 27: 1237
Non-Patent Document 34: Michael, S., et al., *J. Immunol.*, 1997, 159: 3613
Non-Patent Document 35: Esohe E. Idusogie et al. *J. Immunol.* 2000, 164: 4178-4184
Non-Patent Document 36: Yuanyuan Xu et al. *J. Biol. Chem.* 1994, 269: 3469-3474

Non-Patent Document 37: Brekhe, O. H. et al. *Eur J. Imumunol.* 1994, 24: 2542

Non-Patent Document 38: Morgan. A., et al., *Immunology* 1995, 86: 3 19

Non-Patent Document 39: Lund. J., et al., *J. Imununol.*, 1996, 157: 4963

Non-Patent Document 40: Tao, M. H., et. al., *J. Exp. Med* 1993, 178:661

DISCLOSURE OF THE INVENTION

Problem that the Invention is to Solve

An object of the present invention is to provide a monoclonal antibody which has an agonist activity and binds to human CD40; a DNA which encodes the monoclonal antibody; a vector which contains the DNA; a transformant obtainable by introducing the vector; a process for producing the monoclonal antibody using the transformant; and a pharmaceutical composition and a therapeutic agent comprising the monoclonal antibody.

Means for Solving the Problem

The present inventors have constructed a monoclonal antibody (hereinafter referred to as "IgG2-AAS antibody") which has a heavy chain constant region which is IgG2 (hereinafter, referred to as "IgG2-AAS") in which valine at position 234, glycine at position 237 and proline at position 331 are at least substituted with alanine (V234A), alanine (G237A) and serine (P331S), respectively, (numbering is based on the EU index of Kabat et al) and binds to human CD40, and thus the present invention has been completed.

Namely, the present invention relates to the following:

(1) A monoclonal antibody which comprises a heavy chain constant region which is IgG2, in which valine at position 234, glycine at position 237 and proline at position 331 are at least substituted with alanine, alanine and serine, respectively, (numbering is based on the EU index of Kabat et al); has an agonist activity; and binds to human CD40;

(2) A monoclonal antibody which comprises the heavy chain constant region represented by SEQ ID NO:30, has an agonist activity, and binds to human CD40;

(3) The monoclonal antibody according to the above (1) or (2), which comprises a heavy chain variable region comprising CDR1, CDR2 and CDR3 represented by SEQ ID NOs:6, 8 and 10, respectively, and a light chain variable region comprising CDR1, CDR2 and CDR3 represented by SEQ ID NOs:16, 18 and 20, respectively;

(4) The monoclonal antibody according to the above (1) or (2), which comprises the heavy chain variable region represented by SEQ ID NO:4, and the light chain variable region represented by SEQ ID NO:14;

(5) The monoclonal antibody according to the above (1) or (2), which comprises a heavy chain variable region of an antibody produced by a hybridoma KM341-1-19 (FERM BP-7759) and a light chain variable region of an antibody produced by a hybridoma KM341-1-19 (FERM BP-7759);

(6) The monoclonal antibody according to the above (1) or (2), which competes with an antibody produced by a hybridoma KM341-1-19 (FERM BP-7759);

(7) The monoclonal antibody according to the above (1) or (2), which binds to a part or the entirety of an epitope on human CD40 to which an antibody produced by a hybridoma KM341-1-19 (FERM BP-7759) bind;

(8) A DNA which encodes the monoclonal antibody according to any one of the above (1) to (7);

(9) A recombinant vector which comprises the DNA according to the above (8);

(10) A transformant obtainable by introducing the recombinant vector according to the above (9) into a host cell;

(11) A process for producing the monoclonal antibody according to any one of the above (1) to (7), comprising culturing the transformant described in the above (10) in a medium to form and accumulate the monoclonal antibody described in any one of the above (1) to (7) in the culture and recovering the monoclonal antibody from the culture;

(12) The monoclonal antibody according to the above (1) or (2), which comprises a heavy chain constant region in which a signal is removed from the polypeptide represented by SEQ ID NO:2, and a light chain constant region in which a signal is removed from the polypeptide represented by SEQ ID NO:12;

(13) A recombinant vector comprising a DNA which encodes a polypeptide in which a signal is removed from the polypeptide represented by SEQ ID NO:2;

(14) A recombinant vector comprising a DNA which encodes a polypeptide in which a signal is removed from the polypeptide represented by SEQ ID NO:12;

(15) A recombinant vector comprising a DNA encoding a polypeptide in which a signal is removed from the polypeptide represented by SEQ ID NO:1, and a DNA encoding a polypeptide in which a signal is removed from a polypeptide represented by SEQ ID NO:11;

(16) A transformant obtainable by introducing the recombinant vectors according to the above (13) and (14) into a host cell;

(17) A transformant obtainable by introducing the recombinant vector according to the above (15) into a host cell;

(18) A process for producing the monoclonal antibody described in the above (12), comprising culturing the transformant described in the above (16) or (17) in a medium to form and accumulate the monoclonal antibody described in the above (12) in the culture and thereby obtaining the monoclonal antibody from the culture;

(19) A pharmaceutical composition comprising the monoclonal antibody according to any one of the above (1) to (7) and (12) as an active ingredient;

(20) A therapeutic agent for malignant tumors or infections, comprising the monoclonal antibody according to any one of the above (1) to (7) and (12) as an active ingredient;

(21) Use of the monoclonal antibody according to any one of the above (1) to (7) and (12) for the manufacture of a therapeutic agent for malignant tumors or infections;

(22) The monoclonal antibody according to any one of the above (1) to (7) and (12) for treating malignant tumors or infections; and

(23) A method for treating malignant tumors or infections, comprising administration antibody according to any one of the above (1) to (7) and (12).

Advantage of the Invention

As shown in the following Examples, a monoclonal antibody (IgG2-AAS antibody) which comprises a heavy chain constant region, IgG2-AAS, and binds to human CD40 exhibits a remarkably high agonist activity. Therefore, the present invention can provide the monoclonal antibody which comprises a heavy chain constant region which is IgG2, in which valine at position 234, glycine at position 237 and proline at position 331 are at least substituted with alanine, alanine and serine, respectively, (numbering is based on the EU index of Kabat et al); has an agonist activity; and binds to human CD40 (hereinafter referred to as "monoclonal antibody of the present invention"); a DNA which encodes the monoclonal antibody; a vector which comprises the DNA; a transformant obtainable by introducing the vector; a process for producing the monoclonal antibody using the transformant; and a pharmaceutical composition and a therapeutic agent comprising the monoclonal antibody. Alternatively, as shown in the following Example, IgG2-AAS(341) antibody, one of the monoclonal antibodies, has an increased plasma residence time compared to IgG2-S(341). Still further, IgG2-AAS(341) antibody has a decreased liver toxicity compared to IgG2-S(341).

DESCRIPTIONS OF EMBODIMENTS

Figure 1A:
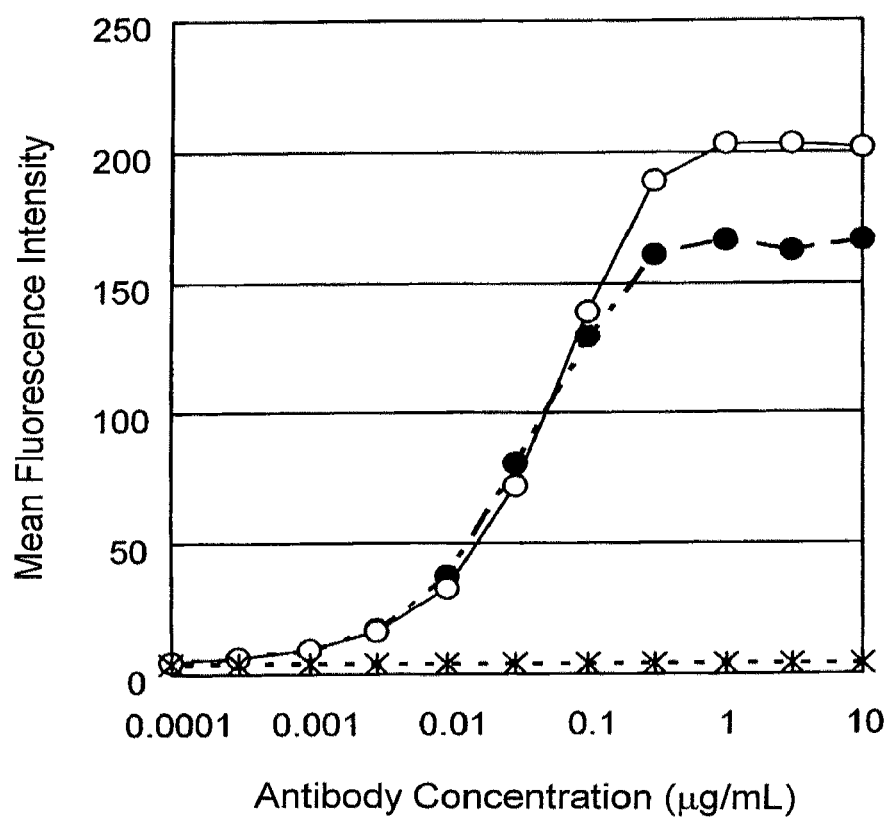
FIG. 1A shows a binding activity of IgG2-AAS(341) antibody. The abscissa represents the antibody concentration (μg/ml) and the ordinate represents the mean fluorescence intensity. The mean fluorescence intensity of IgG2-AAS(341) antibody is represented by the mark ● and the dashed line, the mean fluorescence intensity of IgG2-S(341) antibody is represented by the mark ○ and the solid line and the mean fluorescence intensity of the negative control antibody is represented by the mark * and the dotted line.

The present invention relates to a monoclonal antibody which binds to CD40, comprises a heavy chain constant region, IgG2-AAS and has an agonist activity.

The antibody of the present invention binds to an extracellular region of CD40.

The binding of the antibody of the present invention to CD40 can be confirmed by radioimmunoassay using a solid-phase sandwich method or the like, or by a known immunological detection method using enzyme immunoassay (ELISA) or the like for CD40-expressing cells, preferably a method capable of investigating a binding activity of an antibody for a cell expressing a particular antigen and the particular antigen, such as fluorescent cell staining method. Examples include a fluorescent antibody staining method [*Cancer Immunol. Immunother.*, 36, 373 (1993)] using such as an FMAT8100HTS System (manufactured by Applied Biosystems), a fluorescent cell staining method using flow cytometry, surface plasmon resonance using such as a Biacore System (manufactured by GE Healthcare), or other methods. Furthermore, in addition to the above method, a known immunological detection method [*Monoclonal Antibodies—Principles and practice*, Third edition, Academic Press (1996), *Antibodies—A Laboratory Manual*, Cold Spring Harbor Laboratory (1988), *Monoclonal Antibody Experimental Manual*, Kodan-sha Scientific (1987)] can be combined to confirm these.

The cell expressing CD40 may be any cell, so long as it expresses CD40, and examples include a cell which is naturally present in the human body, a cell line established from the cell which is naturally present in the human body, a cell obtained by gene recombination technique and the like.

The cell which is naturally present in the human body includes a cell expressing the polypeptide in the body of a patient with auto immune disease a patient with allergy, a patient with cancer, such as a cell expressing CD40 among tumor cells obtained by biopsy or the like.

Examples of the cell which is naturally present in the human body include a cell expressing CD40 among cell lines obtained by establishment of the CD40-expressing cells obtained from the above cancer patients, and specific examples include cell lines established from human, such as Ramas (ATCC CRL-1596), Raji (ATCC CCL-86), Daudi (ATCC CCL-213), T24 (ATCC HTB-4) and the like.

Specific Examples of the cell obtained by gene recombination techniques include a CD40-expressing cell obtained by introducing an expression vector comprising a CD40-encoding cDNA into an insect cell, an animal cell or the like, and the like. The nucleotide sequence and the amino acid sequence of human CD40 can be obtained from a known database such as NCBI (http://www.ncbi.nlm.nih.gov/), and are registered as the nucleotide sequence represented by SEQ ID NO:36 (NCBI accession NO: NM_001250) and the amino acid sequence represented by SEQ ID NO:37 (NCBI accession NO: NP_001240), respectively. In the present invention, CD40 means human CD40 in the absence of a particular explanation.

In the present invention, specific examples of the monoclonal antibody may include an antibody secreted by a single clone antibody-producing cell.

The monoclonal antibody means that an antibody which recognizes only one epitope (also called antigen determinant) and has uniform amino acid sequence (primary structure).

In the present invention, the monoclonal antibody comprises two heavy chains (a heavy chain constant region and a heavy chain variable region) and two light chains (a light chain constant region and a light chain variable region).

The epitope include a single amino acid sequence, a three-dimensional structure consisting of an amino acid sequence, an amino acid sequence having a sugar chain bound thereto, a three-dimensional structure consisting of an amino acid sequence having a sugar chain bound thereto, and the like, which a monoclonal antibody recognizes and binds to. The epitope of the monoclonal antibody of the present invention preferably exists in the extracellular region of CD40.

In the present invention, the recombinant antibody includes an antibody produced by gene recombination, such as a human chimeric antibody, a human antibody, a human antibody and an antibody fragment thereof. The CDR is an abbreviated name of a human type complementarity determining region which may be referred to as the CDR hereinafter. Among the recombinant antibodies, one having a character of a monoclonal activity, low immunogenecity and prolonged half-life in blood is preferable as a therapeutic agent.

The human chimeric antibody is an antibody comprising a heavy chain variable region (hereinafter referred to as "VH") and a light chain variable region (hereinafter referred to as "VL") of an antibody of a non-human animal and a heavy chain constant region (hereinafter referred to as "CH") and a light chain constant region (hereinafter referred to as "CL") of a human antibody.

The human chimeric antibody of the present invention can be produced as follows. Specifically, the human chimeric antibody can be produced by obtaining cDNAs encoding VH and VL from a hybridoma which produces a monoclonal antibody which specifically recognizes CD40 and binds to the extracellular region, inserting each of them into an expression vector for animal cell comprising DNAs encoding CH and CL of human antibody to thereby construct a vector for expression of human chimeric antibody, and then introducing the vector into an animal cell to express the antibody. A human CDR-grafted antibody is an antibody in which amino acid sequences of CDRs of VH and VL of an antibody derived from a non-human animal are grafted into appropriate positions of VH and VL of a human antibody.

The human CDR-grafted antibody of the present invention can be produced by constructing cDNAs encoding an antibody variable region (hereinafter referred to as "V region") in which the amino acid sequences of CDRs of VH and VL of an antibody derived from a non-human animal produced by a hybridoma which produces a monoclonal antibody which specifically recognizes CD40 and binds to the extracellular region are grafted into framework regions (hereinafter referred to as "FR") of VH and VL of any human antibody, inserting each of them into a vector for expression of animal cell comprising genes encoding CH and CL of a human antibody to thereby construct a vector for expression of human CDR-grafted antibody, and introducing it into an animal cell to thereby express and produce the human CDR-grafted antibody.

A class of a heavy chain constant region of a human antibody includes IgA, IgM, IgE and IgG, and a subclass of IgG includes IgG1, IgG2, IgG3 and IgG4. IgG2 has a plurality of allotypes (for example, SEQ ID NOs:33, 34 and 35, hereinafter as allotypes 1, 2 and 3, respectively, see AAN76042.1, CAC12842 and AAN76043.1 in NCBI Reference Sequences), and the monoclonal antibody of the present invention may be any one of the allotypes. A class of a light chain constant region of a human antibody includes κ and λ, and the light chain constant region of the monoclonal antibody of the present invention may be either one of them.

A human antibody is originally an antibody naturally existing in the human body, and it also includes antibodies obtained from a human antibody phage library or a human antibody-producing transgenic animal, which is prepared based on the recent advance in genetic engineering, cell engineering and developmental engineering techniques.

The antibody naturally existing in the human body can be prepared, for example by isolating a human peripheral blood lymphocyte, immortalizing it by infecting with EB virus or the like and then cloning it to thereby obtain lymphocytes capable of producing the antibody, culturing the lymphocytes thus obtained, and purifying the antibody from the supernatant of the culture.

The human antibody phage library is a library in which antibody fragments such as Fab and scFv are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the index. The antibody fragment can be converted further into a human antibody molecule comprising two full H chains and two full L chains by genetic engineering techniques.

A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it (Tomizuka. et al., *Proc Natl Acad Sci USA.*, 2000 Vol. 197: 722). A human antibody is prepared from the human antibody-producing transgenic non-human animal by obtaining a human antibody-producing hybridoma using a hybridoma preparation method usually carried out in non-human mammals, culturing the obtained hybridoma and forming and accumulating the human antibody in the supernatant of the culture.

In the present invention, the monoclonal antibody which binds to human CD40 comprises a heavy chain constant region, IgG2-AAS. The present inventors, as shown in Examples, have found that the IgG2-AAS antibody exhibits a higher agonist activity than an antibody (hereinafter, referred to also as "IgG2-S antibody") which comprises a heavy chain constant region which is IgG2 (hereinafter, referred to as "IgG2-S"), in which proline at position 331 is substituted with serine (the number is based on the EU index of Kabat et al.).

In addition, as is shown by Examples, it was found that the IgG2-AAS(341) antibody which was one of the monoclonal antibodies of the invention had an effect to prolong blood residence time in comparison with the IgG2-S(341) antibody. Also, it was further found that the IgG2-AAS(341) antibody had an effect that toxicity for the liver is lowered in comparison with the IgG2-S(341) antibody.

It is known that the CD40 ligand shows toxicity for the liver (*Journal of Clinical Oncology*, 19 (13), 3280-3287 (2001))

and similarly, it is known that a monoclonal antibody which binds to CD40 showing agonist activity also shows toxicity for the liver (*American Journal of Pathology*, 168(3), 786-795 (2006)). Although agonist activity of the IgG2-AAS antibody of the invention is enhanced in comparison with the IgG2-S antibody, its toxicity for the liver is lowered in comparison with the IgG2-S antibody. The lowering of toxicity can be confirmed by such as the decrease in blood concentration of aspartate aminotransferase (hereinafter also referred to as AST) or alanine aminotransferase (hereinafter also referred to as ALT). The antibody of the present invention include an antibody in which one or more amino acid residue(s) is/are deleted, added, substituted and/or inserted in the amino acid sequence which constitute the above-mentioned monoclonal antibody and which has a similar activity to the above-mentioned antibody. The position to which addition, substitution and/or insertion is introduced may specifically exist in a heavy chain constant region, a light chain constant region, a heavy chain variable region or a light chain constant region; more specifically CDR1, CDR2 or CDR3, or a framework region (FR) of the above heavy chain and light chain of variable region.

The number of amino acids which are deleted, substituted, inserted and/or added is one or more, and is not specifically limited, but it is within the range where deletion, substitution or addition is possible by known methods such as the site-directed mutagenesis described in *Molecular Cloning*, 2nd Edition; *Current Protocols in Molecular Biology*, John Wiley & Sons (1987-1997); *Nucleic Acids Research*, 10, 6487 (1982), *Proc. Natl. Acad. Sci. USA*, 79, 6409 (1982); *Gene*, 34, 315 (1985), *Nucleic Acids Research*, 13, 4431 (1985); *Proc. Natl. Acad. Sci. USA*, 82, 488 (1985) or the like. For example, the number is 1 to dozens, preferably 1 to 20, more preferably 1 to 10, and most preferably 1 to 5 (for example, 1, 2, 3, 4 or 5), other than the substitutions of valine at position 234 with alanine, glycine at position 237 with alanine and proline at position 331 with serine.

Therefore, in the present invention, amino acid residue may be deleted, added, substituted and/or inserted except for the substitution of AAS in the heavy chain constant region, IgG2-AAS, and the monoclonal antibody of the present invention include a monoclonal antibody which comprises such a heavy chain constant region.

The expression "one or more amino acid residue(s) is/are deleted, substituted, inserted and/or added" in the amino acid sequence of the above antibody means the followings. That is, it means there is deletion, substitution, insertion or addition of one or plural amino acids at optional positions in the same sequence and one or plural amino acid sequences. Also, the deletion, substitution, insertion or addition may occur at the same time and the amino acid which is substituted, inserted or added may be either a natural type or a non-natural type. The natural type amino acid includes L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Preferable examples of mutually substitutable amino acids are shown below. The amino acids in the same group are mutually substitutable.
Group A: leucine, isoleucine, norleucine, valine, norvaline, alanine, 2-aminobutanoic acid, methionine, O-methylserine, t-butylglycine, t-butylalanine, cyclohexylalanine
Group B: aspartic acid, glutamic acid, isoaspartic acid, isoglutamic acid, 2-aminoadipic acid, 2-aminosuberic acid
Group C: asparagine, glutamine
Group D: lysine, arginine, ornithine, 2,4-diaminobutanoic acid, 2,3-diaminopropionic acid
Group E: proline, 3-hydroxyproline, 4-hydroxyproline
Group F: serine, threonine, homoserine
Group G: phenylalanine, tyrosine The antibody of the present invention includes an antibody conjugate in which a monoclonal antibody which binds to the extracellular region of CD40 is chemically or genetically bound to a radioisotope, an agent having low molecular weight, an agent having high molecular weight, a protein such as antibody, and the like.

The antibody derivative of the present invention can be produced by chemically conjugating a radioisotope a radioisotope, an agent having low molecular weight, an agent having high molecular weight, an immunostimulator, a protein or the like to the N-terminal side or C-terminal side of an H chain or an L chain of the monoclonal antibody which binds to the extracellular region of CD40 in the present invention, an appropriate substituent or side chain of the antibody, a sugar chain in the antibody or the like [*Antibody Engineering Handbook*, edited by Osamu Kanemitsu, published by Chij in Shokan (1994)].

Also, the antibody derivative of the present invention can be genetically produced using a genetic technique, such as, by linking a DNA encoding the monoclonal antibody which binds to the extracellular region of CD40 in the present invention to other DNA encoding a protein to be conjugated or a therapeutic antibody, inserting the DNA into a vector for expression, and introducing the expression vector into an appropriate host cell to express the derivative.

The radioisotope includes $^{131}$I, $^{125}$I, $^{90}$Y, $^{64}$Cu, $^{199}$Tc, $^{77}$Lu, $^{211}$At and the like. The radioisotope can directly be conjugated with the antibody by Chloramine-T method. Also, a substance chelating the radioisotope can be conjugated with the antibody. The chelating agent includes methylbenzyldiethylene-triaminepentaacetic acid (MX-DTPA) and the like.

The agent having low molecular weight includes an antitumor agent such as an alkylating agent, a nitrosourea agent, a metabolism antagonist, an antibiotic substance, an alkaloid derived from a plant, a topoisomerase inhibitor, an agent for hormonotherapy, a hormone antagonist, an aromatase inhibitor, a P glycoprotein inhibitor, a platinum complex derivative, an M-phase inhibitor and a kinase inhibitor [*Rinsho Syuyogaku* (Clinical Oncology), Gan to Kagaguryoho-Sha (1996)], a steroid agent such as hydrocortisone and prednisone, a nonsteroidal agent such as aspirin and indomethacin, immune-regulating agent such as cyclophosphamide and azathioprine, anti-inflammatory agent such as anti-histamine agent (for example, chlorpheniramine maleate and clemastine) [*Ensho to Kouensho-Ryoho* (Inflammation and Anti-inflammation Therapy), Ishiyaku Shuppann (1982)] and the like.

Examples of the antitumor agent include amifostine (Ethyol), cisplatin, dacarbazine (DTIC), dactinomycin, mecloretamin (nitrogen mustard), streptozocin, cyclophosphamide, iphosphamide, carmustine (BCNU), lomustine (CCNU), doxorubicin (adriamycin), epirubicin, gemcitabine (Gemsal), daunorubicin, procarbazine, mitomycin, cytarabine, etoposide, methotrexate, 5-fluorouracil, fluorouracil, vinblastine, vincristine, bleomycin, daunomycin, peplomycin, estramustine, paclitaxel (Taxol), docetaxel (Taxotea), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, iphosphamide, idarubicin, mesna, irinotecan (CPT-11), nogitecan, mitoxantrone, topotecan, leuprolide, megestrol, melfalan, mercaptopurine, hydroxycarbamide, plicamycin, mitotane, pegasparagase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacytidine, UFT, oxaliplatin, gefitinib (Iressa), imatinib (STI 571), elrotinib, FMS-like tyrosine kinase 3 (Flt3) inhibitor, vascular endothelial growth factor receptor (VEGFR) inhibitor, fibroblast growth factor receptor (FGFR inhibitor), epidermal growth factor receptor (EGFR) inhibitor such as Iressa and Tarceva, radicicol, 17-allylamino-17-demethoxygeldanamycin, rapamycin, amsacrine, all-trans-retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestin substances, estrogen substances, anastrozole (Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, voltezomib, allopurinol, calicheamicin, ibritumomab tiuxetan, Targretin, ozogamine, clarithromycin, leucovorin, ifosfamide, ketoconazole, aminoglutethimide, suramin, methotrexate, maytansinoid and derivatives thereof.

The method for conjugating the agent with the antibody includes a method in which the chemotherapeutic agent having low molecular weight and an amino group of the antibody are conjugated via glutaraldehyde, a method in which an amino group of the chemotherapeutic agent and a carboxyl group of the antibody are bound via water-soluble carbodiimide, and the like.

The agent having high molecular weight includes polyethylene glycol (hereinafter referred to as "PEG"), albumin, dextran, polyoxyethylene, styrene-maleic acid copolymer, polyvinylpyrrolidone, pyran copolymer, hydroxypropylmethacrylamide, and the like. By binding these compounds having high molecular weight to an antibody or antibody fragment, the following effects are expected: (1) improvement of stability against various chemical, physical or biological factors, (2) remarkable prolongation of half life in blood, (3) disappearance of immunogenicity, suppression of antibody production, and the like [*Bioconjugate Drug*, Hirokawa Shoten (1993)]. For example, the method for binding PEG to an antibody includes a method in which an antibody is allowed to react with a PEG-modifying reagent [*Bioconjugate Drug*, Hirokawa Shoten (1993)]. The PEG-modifying reagent includes a modifying agent of ε-amino group of lysine (Japanese Published Unexamined Patent Application No. 178926/86), a modifying agent of a carboxyl group of aspartic acid and glutamic acid (Japanese Published Unexamined Patent Application No. 23587/81), a modifying agent of a guanidino group of arginine (Japanese Published Unexamined Patent Application No. 117920/90) and the like.

The immunostimulator includes a natural product known as immunoadjuvant. Specific examples include an agent for stimulating immunity, for example, β(1→3)glucan (such as lentinan and schizophyllan), α-galactosylceramide and the like.

Examples of the protein include cytokine or growth factor which stimulates immunocompetent cells such as NK cell, macrophage and neutrophil; toxic protein; and the like.

Examples of the cytokine or the growth factor include interferon (hereinafter referred to as "INF")-α, INF-β, INF-γ, interleukin (hereinafter referred to as "IL")-2, IL-12, IL-15, IL-18, IL-21, IL-23, granulocyte-colony stimulating factor (G-CSF), granulocyte macrophage-colony stimulating factor (GM-CSF), macrophage-colony stimulating factor (M-CSF) and the like. The toxic protein includes ricin, diphtheria toxin, ONTAK and the like, and also includes a toxic protein wherein mutation is introduced into a protein in order to control the toxicity.

The therapeutic antibody includes an antibody against an antigen in which apoptosis is induced by binding of the antibody, an antibody against an antigen participating in formation of morbid part of tumor, an antibody which regulates immunological function and an antibody relating to angiogenesis in the morbid part.

The antigen in which apoptosis is induced by binding of the antibody includes cluster of differentiation (hereinafter "CD") 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, Epidermal Growth Factor Receptor (EGFR) and the like.

The antigen for the antibody which regulates immunological function includes CD40, CD40 ligand, B7 family molecule (CD80, CD86, CD274, B7-DC, B7-H2, B7-H3, B7-H4, etc.), ligand of B7 family molecule (CD28, CTLA-4, ICOS, PD-1, BTLA, etc.), OX-40, OX-40 ligand, CD137, tumor necrosis factor (TNF) receptor family molecule (DR4, DR5, TNFR1, TNFR2, etc.), TNF-related apoptosis-inducing ligand receptor (TRAIL) family molecule, receptor family of TRAIL family molecule (TRAIL-R1, TRAIL-R2, TRAIL-R3, TRAIL-R4, etc.), receptor activator of nuclear factor kappa B ligand (RANK), RANK ligand, CD25, folic acid receptor 4, cytokine [IL-1α, IL-1β, IL-4, IL-5, IL-6, IL-10, IL-13, transforming growth factor (TGF) β, TNFα, etc.], receptors of these cytokines, chemokine (SLC, ELC, 1-309, TARC, MDC, CTACK, etc.) and receptors of these chemokines.

The antigen for the antibody which inhibits angiogenesis in the morbid part includes vascular endothelial growth factor (VEGF), angiopoietin, fibroblast growth factor (FGF), EGF, platelet-derived growth factor (PDGF), insulin-like growth factor (IGF), erythropoietin (EPO), TGFβ, IL-8, ephilin, SDF-1 and the like.

A fusion body with a protein such as therapeutic antibody can be produced by linking a cDNA encoding a monoclonal antibody to a cDNA encoding the protein, constructing a DNA encoding the fusion antibody, inserting the DNA into an expression vector for prokaryote or eukaryote, and then introducing the expression vector into a prokaryote or eukaryote to express the fusion antibody.

When the above antibody derivative is used in a detection method, a determination method, used as a detection reagent, a determination reagent or a diagnostic reagent, examples of the agent for binding to the monoclonal antibody which binds to the extracellular region of CD40 includes a method in which a specified label is used by labeling the antibody of the present invention. The label includes a label which is used in the general immunological detection or measuring method, and examples include enzymes such as alkaline phosphatase, peroxidase and luciferase, luminescent materials such as acridinium ester and lophine, fluorescent materials such as fluorescein isothiocyanate (FITC) and tetramethyl rhodamine isothiocyanate (RITC), and the like.

Further, the present invention relates to a pharmaceutical composition and a therapeutic agent comprising a monoclonal antibody which binds to an extracellular region of CD40, as an active ingredient. The disease is not limited so long as it is a disease for which an anti-CD40 antibody having an agonist activity is therapeutically effective. Examples of the diseases include infections (caused by, for example, hepatitis B virus, hepatitis C virus, hepatitis A virus, influenza virus, *Listeria monocytogenes*, tubercle *bacillus*, malaria *plasmodium* or *Toxoplasma gondii*) and malignant tumors, since the anti-CD40 antibody having an agonist activity induces cell-mediated immunity and humoral-mediated immunity as described above. In the case where cancer cells themselves in a malignant tumor express CD40, the malignant tumor can also be treated through the induction of cellular apoptosis by the anti-CD40 antibody having an agonist activity. Examples of malignant tumors include malignant lymphoma, malignant melanoma, lung cancer, bladder cancer, pancreatic cancer, pharyngeal cancer, mesothelioma, breast cancer, gastric cancer, esophageal cancer, colorectal cancer, hepatocellular carcinoma, gastric cell carcinoma, prostate cancer, uterine cancer and ovarian cancer.

The therapeutic agent of the present invention comprises the above monoclonal antibody as an active ingredient.

The therapeutic agent comprising the antibody is preferably supplied as a pharmaceutical preparation produced by an appropriate method well known in the technical field of pharmaceutics, by mixing it with one or more pharmaceutically acceptable carriers.

It is preferred to select a route of administration which is most effective in treatment. Examples include oral administration and parenteral administration, such as buccal, tracheal, rectal, subcutaneous, intramuscular or intravenous administration. In the case of an antibody or peptide formulation, intravenous administration is preferred. The dosage form includes sprays, capsules, tablets, granules, syrups, emulsions, suppositories, injections, ointments, tapes and the like.

Although the dose or the frequency of administration varies depending on the objective therapeutic effect, administration method, treating period, age, body weight and the like, it is usually 10 µg/kg to 10 mg/kg per day and per adult.

Further, the present invention relates to a method for immunologically detecting or measuring CD40, a reagent for immunologically detecting or measuring CD40, a method for immunologically detecting or measuring a cell expressing CD40, and a diagnostic agent for diagnosing a disease relating to CD40 positive cells, comprising a monoclonal antibody which binds to the extracellular region of CD40 as an active ingredient.

In the present invention, examples of the method for detecting or measuring CD40 include any known method. Examples include method of immunological detection or immunological measurement and the like.

The method of immunological detection or immunological measurement is a method in which an antibody amount or an antigen amount is detected or determined using a labeled antigen or antibody. Examples of the immunological detection or immunological measurement are radioactive substance-labeled immunoantibody method (RIA), enzyme immunoassay (EIA or ELISA), fluorescent immunoassay (FIA), luminescent immunoassay, Western blotting method, physicochemical means and the like.

By detecting or measuring the cell expressing CD40 using the monoclonal antibody of the present invention, the disease relating to CD40 can be diagnosed.

For the detection of the cell expressing the polypeptide, known immunological detection methods can be used, and an immunoprecipitation method, a fluorescent cell staining method, an immune tissue staining method and the like are preferably used. Also, an immunofluorescent staining method using FMAT 8100 HTS system (Applied Biosystem) and the like can be used.

The living body sample to be used for the detection or measurement of CD40 in the present invention is not particularly limited, so long as it has a possibility of containing CD40, such as tissue cells, blood, blood plasma, serum, pancreatic juice, urine, fecal matter, tissue fluid or culture medium.

The diagnostic reagent comprising the antibody of the present invention may further contain a reagent for carrying out an antigen-antibody reaction or a reagent for detection of the reaction depending on the desired diagnostic method. The reagent for carrying out the antigen-antibody reaction includes a buffer, a salt, and the like. The reagent for detection includes a reagent used for common immunological detection or immunoassay such as a labeled secondary antibody for recognizing the antibody and a substrate corresponding to the labeling.

A process for producing the antibody of the present invention, a method for treating the disease and a method for diagnosing the disease are specifically described below.

1. Preparation of Monoclonal Antibody
(1) Preparation of Antigen

CD40 as an antigen or a cell expressing CD40 can be obtained by introducing an expression vector comprising cDNA encoding a full length or partial length of CD40 into *Escherichia coli*, yeast, an insect cell, an animal cell or the like. Also, CD40 can be obtained by purifying from various human tumor culturing cells, human tissue and the like which express a large amount of CD40. Furthermore, the tumor culturing cell, the tissue or the like can be used as an antigen. In addition, a synthetic peptide having a partial sequence of CD40 can be prepared using a chemical synthetic method such as Fmoc method and tBoc method and used as an antigen.

CD40 used in the present invention can be produced, for example, using the following method to express a DNA encoding CD40 in a host cell.

Firstly, a recombinant vector is prepared by introducing a full length cDNA into downstream of a promoter of an appropriate expression vector. At this time, if necessary, a DNA fragment having an appropriate length containing a region encoding the polypeptide based on the full length cDNA, and the DNA fragment may be used instead of the above full length cDNA. Next, a transformant producing the polypeptide can be obtained by introducing the recombinant vector into a host cell suitable for the expression vector.

The expression vector includes vectors which can replicate autonomously in the host cell to be used or vectors which can be integrated into a chromosome comprising an appropriate promoter at such a position that the DNA encoding the portion encoding the polypeptide can be transcribed.

The host cell may be any one, so long as it can express the gene of interest, and includes *Escherichia coli*, yeast, an insect cell, an animal cell and the like.

When a prokaryote such as *Escherichia coli* is used as the host cell, it is preferred that the recombinant vector is autonomously replicable in the prokaryote and contains a promoter, a ribosome binding sequence, the DNA encoding CD40 and a transcription termination sequence. The recombinant vector is not necessary to have a transcription termination sequence, but a transcription termination sequence is preferably set just below the structural gene. Furthermore, the recombinant vector may further comprise a gene regulating the promoter.

Also, the above recombinant vector is preferably a plasmid in which the space between Shine-Dalgarno sequence (also referred to as SD sequence), which is the ribosome binding sequence, and the initiation codon is adjusted to an appropriate distance (for example, 6 to 18 nucleotides).

Furthermore, the nucleotide sequence of the DNA encoding CD40 can be substituted with another base so as to be a suitable codon for expressing in a host cell, thereby improve the productivity of the objective CD40.

The expression vector includes, for example, pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agricultural Biological Chemistry*, 48, 669 (1984)], pLSA1 [*Agric. Biol. Chem.*, 53, 277 (1989)], pGEL1 [*Proc. Natl. Acad. Sci. USA*, 82, 4306 (1985)], BLUESCRIPT® II SK(-) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. No. 4,686,191, U.S. Pat. No. 4,939,094, U.S. Pat. No. 5,160,735), pSupex, pUB110, pTP5, pC194, pEG400 [*J. Bacteriol.*, 172, 2392 (1990)], pGEX (manufactured by Pharmacia), pET system (manufactured by Novagen), pME18SFL3 and the like.

Any promoter can be used, so long as it can function in the host cell to be used. Examples include promoters derived from *Escherichia coli*, phage and the like, such as trp promoter (Ptrp), lac promoter, PL promoter, PR promoter and T7 promoter. Also, artificially designed and modified promoters, such as a promoter in which two Ptrp are linked in tandem, tac promoter, lacT7 promoter and letI promoter, can be used.

Examples of the host cell includes *Escherichia coli* XL1-BLUE®, *Escherichia coli* XL2-BLUE®, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* DH5α and the like.

Any introduction method of the recombinant vector can be used, so long as it is a method for introducing DNA into the above-described host cell, and examples include a method using a calcium ion described in *Proc. Natl. Acad. Sci. USA*, 69, 2110 (1972), methods described in *Gene*, 17, 107 (1982) and *Molecular & General Genetics*, 168, 111 (1979) and the like.

When an animal cell is used as the host cell, an expression vector includes, for example, pcDNAI, pcDM8 (available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840, (1987)], pcDNAI/Amp (manufactured by Invitrogen), pREP4 (manufactured by Invitrogen), pAGE103 [*J. Biochemistry*, 101, 1307 (1987)], pAGE210, pME18SFL3, pKANTEX93 (WO 97/10354) and the like.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRα promoter and the like. Also, the enhancer of the IE gene of human CMV can be used together with the promoter.

The host cell includes human leukemia Namalwa cell, monkey COS cell, Chinese hamster ovary (CHO) cell (*Journal of Experimental Medicine*, 108, 945 (1958); *Proc. Natl. Acad. Sci. USA*, 60, 1275 (1968); *Genetics*, 55, 513 (1968); *Chromosoma*, 41, 129 (1973), *Methods in Cell Science*, 18, 115 (1996); *Radiation Research*, 148, 260 (1997); *Proc. Natl. Acad. Sci. USA*, 77, 4216 (1980); *Proc. Natl. Acad. Sci. USA*, 60, 1275 (1968); *Cell*, 6, 121 (1975); *Molecular Cell Genetics*, Appendix I, II (pp. 883-900)), CHO/DG44, CHO-K1 (ATCC CCL-61), DukXB11 (ATCC CCL-9096), Pro-5 (ATCC CCL-1781), CHO-S (Life Technologies, Cat #11619), Pro-3, rat myeloma cell YB2/3HL.P2.G11.16AG.20 (referred to as YB2/0), mouse myeloma cell NS0, mouse myeloma cell SP2/0-Ag14, syrian hamster cell BHK or, HBT5637 (Japanese Published Unexamined Patent Application No. 299/88) and the like.

Any introduction method of the recombinant vector can be used, so long as it is a method for introducing DNA into an animal cell, and examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the like.

CD40 can be produced by culturing the transformant derived from a microorganism, an animal cell or the like having a recombinant vector comprising DNA encoding CD40 obtained by the procedure described above in a medium to form and accumulate CD40 in the culture, and recovering it from the culture. The method for culturing the transformant in the medium is carried out according to the usual method used in culturing of hosts.

When the vector is expressed in a cell derived from a eukaryote, CD40 to which sugars or sugar chains is bound can be obtained.

When a microorganism transformed with a recombinant vector containing an inducible promoter as a promoter is cultured, an inducer can be added to the medium, if necessary. For example, isopropyl-β-D-thiogalactopyranoside or the like can be added to the medium when a microorganism transformed with a recombinant vector using lac promoter is cultured; or indoleacrylic acid or the like can be added thereto when a microorganism transformed with a recombinant vector using trp promoter is cultured.

When a transformant obtained using an animal cell as the host cell is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)] and 199 medium [*Proceeding of the Society for the Biological Medicine*, 73, 1 (1950)], Iscove's Modified Dulbecco's medium (IMDM), the media to which fetal calf serum, etc. is added, and the like. The culturing is carried out generally at a pH of 6 to 8 and 30 to 40° C. for 1 to 7 days in the presence of 5% $CO_2$. If necessary, an antibiotic such as kanamycin or penicillin can be added to the medium during the culturing.

Regarding the expression method of gene encoding CD40, in addition to direct expression, secretory production, fusion protein expression and the like can be carried out according to the method described in *Molecular Cloning, A Laboratory Manual*, Second Edition, Cold Spring Harbor Laboratory Press (1989).

The process for producing CD40 includes a method of intracellular expression in a host cell, a method of extracellular secretion from a host cell, a method of producing on a host cell membrane outer envelope, and the like. The appropriate method can be selected by changing the host cell used and the structure of the polypeptide produced.

When CD40 is produced in a host cell or on a host cell membrane outer envelope, CD40 can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Unexamined Patent Application No. 336963/93 and WO 94/23021, and the like.

Also, the production amount can be increased in accordance with the method described in Japanese Published Unexamined Patent Application No. 227075/90 utilizing a gene amplification system using such as a dihydrofolate reductase gene.

CD40 can be isolated and purified from the above culture, for example, as follows.

When CD40 is intracellularly expressed in a dissolved state, the cells after culturing are recovered by centrifugation, suspended in an aqueous buffer and then disrupted using ultrasonicator, French press, Manton Gaulin homogenizer, dynomill or the like to obtain a cell-free extract. The cell-free extract is centrifuged to obtain a supernatant, and a purified preparation can be obtained by subjecting the supernatant to a general enzyme isolation and purification techniques such as solvent extraction; salting out with ammonium sulfate etc.; desalting; precipitation with an organic solvent; anion exchange chromatography using a resin such as diethylaminoethyl (DEAE)-sepharose, DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

When CD40 is expressed intracellularly by forming an inclusion body, the cells are recovered, disrupted and centrifuged in the same manner, and the inclusion body of CD40 are recovered as a precipitation fraction. The recovered inclusion body of the protein is solubilized with a protein denaturing agent. The protein is made into a normal three-dimensional structure by diluting or dialyzing the solubilized solution, and then a purified product of CD40 is obtained by the same isolation purification method as above.

When CD40 or the derivative such as a glycosylated product is secreted extracellularly, CD40 or the derivative such as a glycosylated product can be recovered from the culture supernatant. That is, the culture is treated by a method such as centrifugation in the same manner as above to obtain a culture supernatant from which solids are removed, a purified product of CD40 can be obtained from the culture supernatant by the same isolation purification method as above.

Also, CD40 used in the present invention can be produced by a chemical synthesis method, such as Fmoc method or tBoc method. Also, it can be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(2) Immunization of Animal and Preparation of Antibody-Producing Cell for Fusion A mouse, rat or hamster 3 to 20 weeks old is immunized with the antigen prepared in the above (1), and antibody-producing cells are collected from the spleen, lymph node or peripheral blood of the animal. Also, when the increase of a sufficient titer in the above animal is not recognized due to low immunogenecity, a CD40 knockout mouse may by used as an animal to be immunized.

The immunization is carried out by administering the antigen to the animal through subcutaneous, intravenous or intraperitoneal injection together with an appropriate adjuvant (for example, complete Freund's adjuvant, combination of aluminum hydroxide gel with pertussis vaccine, or the like). When the antigen is a partial peptide, a conjugate is produced with the partial peptide and a carrier protein such as BSA (bovine serum albumin), KLH (keyhole limpet hemocyanin) or the like, which is used as the antigen.

The administration of the antigen is carried out 5 to 10 times every one week or every two weeks after the first administration. On the 3rd to 7th day after each administration, a blood sample is collected from the fundus of the eye, the reactivity of the serum with the antigen is tested, for example, by enzyme immunoassay [*Antibodies—A Laboratory Manual* (Cold Spring Harbor Laboratory (1988)] or the like. A mouse, rat or hamster showing a sufficient antibody titer in their sera against the antigen used for the immunization is used as the supply source of an antibody-producing cell for fusion.

In fusion of the antibody-producing cells and myeloma cells, on the 3rd to 7th days after the final administration of the antigen, tissue containing the antibody-producing cells such as the spleen from the immunized mouse, rat or hamster is excised to collect the antibody-producing cell. When the spleen cells are used, the spleen is cut out and loosened followed by centrifuged. Then, antibody-producing cells for fusion are obtained by removing erythrocytes.

(3) Preparation of Myeloma Cell

An established cell line obtained from mouse is used as myeloma cells. Examples include 8-azaguanine-resistant mouse (derived from BALB/c mouse) myeloma cell line P3-X63Ag8-U1 (P3-U1) [*Current Topics in Microbiology and Immunology*, 18, 1-7 (1978)], P3-NS1/1-Ag41 (NS-1) [*European J Immunology*, 6, 511-519 (1976)], SP2/0-Ag14 (SP-2) [*Nature*, 276, 269-270 (1978)], P3-X63-Ag8653 (653) [*J Immunology*, 123, 1548-1550 (1979)], P3-X63-Ag8 (X63) [*Nature*, 256, 495-497 (1975)] and the like.

These cell lines are subcultured in a normal medium [a medium in which glutamine, 2-mercaptoethanol, gentamicin, FBS and 8-azaguanine are added to RPMI-1640 medium] and they are subcultured in the normal medium 3 or 4 days before cell fusion to ensure the cell number of $2 \times 10^7$ or more on the day for fusion.

(4) Cell Fusion and Preparation of Hybridoma for Producing Monoclonal Antibody

The antibody-producing cells for fusion obtained in the above (2) and myeloma cells obtained in the above (3) were sufficiently washed with a Minimum Essentional Medium (MEM) medium or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells: the myeloma cells=5 to 10:1, followed by centrifugation. Then, the supernatant is discarded. The precipitated cell group is sufficiently loosened. After loosening the precipitated cell, the mixture of polyethylene glycol-1000 (PEG-1000), MEM medium and dimethylsulfoxide is added to the cell under stirring at 37° C. In addition, 1 to 2 mL of MEM medium is added several times every one or two minutes, and MEM medium is added to give a total amount of 50 mL. After centrifugation, the supernatant is discarded. After the precipitated cell group is gently loosened, the cells are gently suspended in HAT medium [a medium in which hypoxanthine, thymidine and aminopterinis added to the normal medium]. The suspension is cultured in a 5% $CO_2$ incubator for 7 to 14 days at 37° C.

After the culturing, a portion of the culture supernatant is sampled and a hybridoma which is reactive to an antigen containing CD40 and is not reactive to an antigen which does not contain CD40 is selected by a hybridoma selection method such as a binding assay as described below. Then, cloning is carried out twice by a limiting dilution method [firstly, HT medium (HAT medium from which aminopterin is removed) is used, and secondly, the normal medium is used], and a hybridoma which shows a stably high antibody titer is selected as the monoclonal antibody-producing hybridoma.

(5) Preparation of Purified Monoclonal Antibody

The hybridoma cells producing a monoclonal antibody obtained by the above (4) are administered by intraperitoneal injection into 8- to 10-week-old mice or nude mice treated with pristane (0.5 mL of 2,6,10,14-tetramethylpentadecane (pristane) is intraperitoneally administered, followed by feeding for 2 weeks). The hybridoma develops ascites tumor in 10 to 21 days. The ascitic fluid is collected from the mice, centrifuged to remove solids, subjected to salting out with 40 to 50% saturated ammonium sulfate and then precipitated by caprylic acid, passed through a DEAE-Sepharose column, a protein A column or a gel filtration column to collect an IgG or IgM fraction as a purified monoclonal antibody.

Furthermore, a monoclonal antibody-producing hybridoma obtained in the above (4) is cultured in such as RPMI1640 medium including 10% FBS and the supernatant is removed by the centrifugation. The precipitated cells are suspended in Hybridoma SFM medium and cultured in 3 to 7 days. The obtained cell suspension is centrifuged and the resulting supernatant is passed through a protein A column or a protein G column to collect an IgG fraction and thereby obtain the purified monoclonal antibody. In addition, 5% of DIGO GF21 can be contained in Hybridoma SFM medium.

The subclass of the antibody can be determined using a subclass typing kit by enzyme immunoassay. The amount of the protein can be determined by the Lowry method or from the absorbance at 280 nm.

(6) Selection of Monoclonal Antibody

Selection of monoclonal antibody is carried out by the following binding assay using enzyme immunoassay method.

As the antigen, a gene-introduced cell or a recombinant protein obtained by introducing an expression vector comprising a cDNA encoding CD40 obtained in the above (1) into *Escherichia coli*, yeast, an insect cell, an animal cell or the like, or a purified polypeptide or partial peptide obtained from a human tissue is used. When the antigen is a partial peptide, a conjugate is prepared with BSA, KLH or the like and is used.

After making these antigens into a solid layer by dispensing in a 96-well plate, a serum of an animal to be immunized, a culture supernatant of a monoclonal antibody-producing hybridoma or a purified antibody is dispensed therein as the primary antibody and allowed to react. After thoroughly washing with PBS or PBS-Tween, an anti-immunoglobulin antibody labeled with biotin, an enzyme, a chemiluminescent material, a radiation compound or the like is dispensed therein as the secondary antibody and allowed to react. After thoroughly washing with PBS-Tween, the reaction depending on the label of the secondary antibody is carried out to select an monoclonal antibody which specifically react to the antigen.

The antibody which competes with the anti-CD40 monoclonal antibody of the present invention for its binding to the extracellular region of CD40 can be prepared by adding an antibody to be tested to the above-mentioned binding assay system and carrying out reaction. That is, a monoclonal antibody which competes with the thus obtained monoclonal antibody for its binding to the extracellular region of CD40 can be prepared by carrying out a screening of an antibody by which the binding of the monoclonal antibody is inhibited when the antibody to be tested is added.

Furthermore, an antibody which binds to an epitope which is the same as the epitope recognized by the monoclonal antibody of the present invention which recognizes the extracellular region of CD40 can be obtained by identifying the epitope of the antibody obtained in the above binding assay, and preparing a partial synthetic peptide, a synthetic peptide mimicking the three-dimensional structure of the epitope or the like, followed by immunization.

In the present invention, an agonist activity can be measured by a variety of assays. For example, as shown in Examples, a method for measuring the promotion of CD95 expression by an anti-CD40 antibody using Ramos cells may be exemplified.

2. Preparation of Recombinant Antibody

As production examples of recombinant antibodies, processes for producing a human chimeric antibody and a human CDR-grafted antibody are shown below.

(1) Construction of Vector for Expression of Recombinant Antibody

A vector for expression of recombinant antibody is an expression vector for animal cell into which DNAs encoding CH and CL of a human antibody have been inserted, and is constructed by cloning each of DNAs encoding CH and CL of a human antibody into an expression vector for animal cell.

The C region of a human antibody may be CH and CL of any human antibody. Examples include CH belonging to γ1 subclass, CL belonging to κ class, and the like. As the DNAs encoding CH and CL of a human antibody, a chromosomal DNA comprising an exon and an intron or cDNA can be used. As the expression vector for animal cell, any expression vector can be used, so long as a gene encoding the C region of a human antibody can be inserted thereinto and expressed therein. Examples include pAGE107 [*Cytotechnol.*, 3, 133 (1990)], pAGE103 [*J. Biochem.*, 101, 1307 (1987)], pHSG274 [*Gene*, 27, 223 (1984)], pKCR [*Proc. Natl. Acad. Sci. USA*, 78, 1527 (1981)], pSG1bd2-4 [*Cytotechnol.*, 4, 173 (1990)], pSE1UK1Sed1-3 [*Cytotechnol.*, 13, 79 (1993)] and the like. Examples of a promoter and enhancer used for an expression vector for animal cell include an SV40 early promoter [*J. Biochem.*, 101, 1307 (1987)], a Moloney mouse leukemia virus LTR [Biochem. *Biophys. Res. Commun.*, 149, 960 (1987)], an immunoglobulin H chain promoter [*Cell*, 41, 479 (1985)] and enhancer [*Cell*, 33, 717 (1983)] and the like.

In respect of easiness of construction of a vector for expression of recombinant antibody, easiness of introduction into animal cells, and balance between the expression amounts of antibody H and L chains in animal cells, a type in which both genes exist on the same vector (tandem type) is used as the vector for expression of recombinant antibody [*J. Immunol. Methods*, 167, 271 (1994)]. However, a type in which a gene encoding an antibody H chain and a gene encoding an antibody L chain exist on separate vectors can be used. Examples of the tandem type of the vector for expression of recombinant antibody include pKANTEX93 (WO 97/10354), pEE18 [*Hybridoma*, 17, 559 (1998)], and the like.

(2) Obtaining of cDNA Encoding V Region of Antibody Derived from Non-Human Animal and Analysis of Amino Acid Sequence cDNAs encoding VH and VL of an antibody derived from a non-human animal are obtained as follows.

mRNA is extracted from hybridoma cells producing an antibody derived from a non-human animal to synthesize cDNA. The synthesized cDNA is cloned into a vector such as a phage or a plasmid, to prepare a cDNA library. Each of a recombinant phage or recombinant plasmid comprising cDNA encoding VH or VL is isolated from the library using DNA encoding a part of the C region or V region of an antibody derived from a non-human animal as the probe. The full length of the nucleotide sequences of VH and VL of the antibody derived from a non-human animal of interest on the recombinant phage or recombinant plasmid are determined, and the full length of the amino acid sequences of VH and VL are deduced from the nucleotide sequences.

The non-human animal may be any animal such as mouse, rat, hamster or rabbit, so long as a hybridoma cell can be produced therefrom.

Examples of the method for preparing total RNA from a hybridoma cell include a guanidine thiocyanate-cesium trifluoroacetate method [*Methods in Enzymol.*, 154, 3 (1987)]; a kit such as RNA easy kit (manufactured by Qiagen); and the like.

Examples of the method for preparing mRNA from total RNA include an oligo (dT) immobilized cellulose column method [*Molecular Cloning, A Laboratory Manual*, Second Edition, Cold Spring Harbor Laboratory Press (1989)]; a kit such as Oligo-dT30 <Super> mRNA Purification Kit (manufactured by Takara Bio); and the like. Furthermore, mRNA can be prepared from a hybridoma cell using a kit such as Fast Track mRNA Isolation Kit (manufactured by Invitrogen), Quick Prep mRNA Purification Kit (manufactured by Pharmacia) and the like.

Examples of the method for synthesizing cDNA and preparing a cDNA library include known methods [*Molecular Cloning, A Laboratory Manual*, Cold Spring Harbor Lab. Press (1989); *Current Protocols in Molecular Biology*, Supplement 1, John Wiley & Sons (1987-1997)]; a kit such as Super Script™ Plasmid System for cDNA Synthesis and Plasmid Cloning (manufactured by Invitrogen), ZAP-cDNA Kit (manufactured by Stratagene); and the like.

The vector into which the synthesized cDNA using mRNA extracted from a hybridoma cell as the template is inserted for preparing a cDNA library may be any vector, so long as the cDNA can be inserted. Examples include ZAP Express [*Strategies*, 5, 58 (1992)], pBLUESCRIPT® II SK(+) [*Nucleic Acids Research*, 17, 9494 (1989)], λzapII (manufactured by Stratagene), λgt10 and λgt11 [*DNA Cloning: A Practical Approach*, I, 49 (1985)], Lambda BlueMid (manufactured by Clontech), λExCell and pT7T3-18U (manufactured by Pharmacia), pcD2 [*Mol. Cell. Biol.*, 3, 280 (1983)], pUC18 [*Gene*, 33, 103 (1985)], and the like.

Any *Escherichia coli* for introducing the cDNA library constructed by a phage or plasmid vector may be used, so long as the cDNA library can be introduced, expressed and maintained. Examples include XL1-BLUE® MRF' [*Strategies*, 5, 81 (1992)], C600 [*Genetics*, 39, 440 (1954)], Y1088 and Y1090 [*Science*, 222: 778 (1983)], NM522 [*J. Mol. Biol.*, 166, 1 (1983)], K802 [*J. Mol. Biol.*, 16, 118 (1966)], JM105 [*Gene*, 38, 275 (1985)], and the like.

A colony hybridization or plaque hybridization method using an isotope- or fluorescence-labeled probe may be used for selecting cDNA clones encoding VH and VL of an antibody derived from a non-human animal from the cDNA library [*Molecular Cloning, A Laboratory Manual*, Second Edition, Cold Spring Harbor Laboratory Press (1989)].

Also, the cDNAs encoding VH and VL can be prepared through polymerase chain reaction (hereinafter referred to as "PCR"; *Molecular Cloning, A Laboratory Manual*, Second Edition, Cold Spring Harbor Laboratory Press (1989); *Current Protocols in Molecular Biology*, Supplement 1, John Wiley & Sons (1987-1997)) by preparing primers and using cDNA prepared from mRNA or a cDNA library as the template.

The nucleotide sequence of the cDNA can be determined by digesting the cDNA selected by the above method with appropriate restriction enzymes and the like, cloning the fragments into a plasmid such as pBLUESCRIPT® SK(−) (manufactured by Stratagene), carrying out the reaction by a usually used nucleotide analyzing method such as the dideoxy method of Sanger, F. et al. [*Proc. Natl. Acad. Sci. USA*, 74, 5463 (1977)], and then analyzing the sequence using an automatic nucleotide sequence analyzer such as A.L.F. DNA sequencer (manufactured by Pharmacia).

Whether the obtained cDNAs encode the full amino acid sequences of VH and VL of the antibody containing a secretory signal sequence can be confirmed by estimating the full length of the amino acid sequences of VH and VL from the determined nucleotide sequence and comparing them with the full length of the amino acid sequences of VH and VL of known antibodies [*Sequences of Proteins of Immunological Interest*, US Dept. Health and Human Services (1991)]. The length of the secretory signal sequence and N-terminal amino acid sequence can be deduced by comparing the full length of the amino acid sequences of VH and VL of the antibody comprising a secretory signal sequence with full length of the amino acid sequences of VH and VL of known antibodies [*Sequences of Proteins of Immunological Interest*, US Dept. Health and Human Services (1991)], and the subgroup to which they belong can also be known. Furthermore, the amino acid sequence of each of CDRs of VH and VL can be found by comparing the obtained amino acid sequences with amino acid sequences of VH and VL of known antibodies [*Sequences of Proteins of Immunological Interest*, US Dept. Health and Human Services (1991)].

Moreover, the novelty of the sequence can be examined by carrying out a homology search with sequences in any database, for example, SWISS-PROT, PIR-Protein or the like using the obtained full length of the amino acid sequences of VH and VL, for example, according to the BLAST method [*J. Mol. Biol.*, 215, 403 (1990)] or the like.

(3) Construction of Vector for Expression of Human Chimeric Antibody cDNAs encoding VH and VL of antibody of non-human animal are cloned in the upstream of genes encoding CH or CL of human antibody of vector for expression of recombinant antibody obtained in the above (1) to thereby construct a vector for expression of human chimeric antibody.

For example, each cDNA encoding VH and VL of antibody of non-human animal is ligated to synthetic DNA comprising a nucleotide sequence of 3'-terminal of VH or VL of antibody of non-human animal and a nucleotide sequence of 5'-terminal of CH or CL of human antibody and having recognition sequence of an appropriate restriction enzyme at both ends, and cloned so that each of them is expressed in an appropriate form in the upstream of gene encoding CH or CL of human antibody of the vector for expression of human CDR-grafted antibody obtained in the above (1) to construct a vector for expression of human chimeric antibody.

In addition, cDNA encoding VH or VL of the antibody derived from a non-human animal is amplified by PCR using a synthetic DNA having a recognition sequence of an appropriate restriction enzyme at both terminals and each of them is cloned to the vector for expression of recombinant antibody obtained in the above (1).

(4) Construction of cDNA Encoding V Region of Human CDR-Grafted Antibody cDNAs encoding VH or VL of a human CDR-grafted antibody can be obtained as follows. First, amino acid sequences of FR in VH or VL of a human antibody to which amino acid sequences of CDRs in VH or VL of an antibody derived from a non-human animal are transplanted are selected. As an amino acid sequence of FR to be selected, any amino acid sequences can be used, so long as they are from human. Examples include amino acid sequences of FRs in VH or VL of human antibodies registered in database such as Protein Data Bank or the like, and amino acid sequences common to subgroups of FRs in VH or VL of human antibodies [*Sequences of Proteins of Immunological Interest*, US Dept. Health and Human Services (1991)], and the like. In order to inhibit the decrease in the binding activity of the antibody, amino acid sequences of FR having high homology (at least 60% or more) with the amino acid sequence of FR in VH or VL of the original antibody is selected.

Then, amino acid sequences of CDRs of VH or VL of the original antibody are grafted to the selected amino acid sequence of FR in VH or VL of the human antibody, respectively, to design each amino acid sequence of VH or VL of a human CDR-grafted antibody. The designed amino acid sequences are converted to DNA sequences by considering the frequency of codon usage found in nucleotide sequences of genes of antibodies [*Sequence of Proteins of Immunological Interest*, US Dept. Health and Human Services (1991)], and the DNA sequence encoding the amino acid sequence of VH or VL of a human CDR-grafted antibody is respectively designed.

Based on the designed nucleotide sequences, several synthetic DNAs having a length of about 100 nucleotides are synthesized, and PCR is carried out using them. In this case, it is preferred in each of the H chain and the L chain that 6 synthetic DNAs are designed in view of the reaction efficiency of PCR and the lengths of DNAs which can be synthesized.

Furthermore, the cDNA encoding VH or VL of a human CDR-grafted antibody can be easily cloned into the vector for expression of human CDR-grafted antibody constructed in the above (1) by introducing the recognition sequence of an appropriate restriction enzyme to the 5' terminal of the synthetic DNAs existing on the both ends.

Alternatively, based on the desired nucleotide sequence, the cloning of cDNA can be carried our using each of the H chain synthesized as one DNA and the full-length L chain of synthetic DNA.

After the PCR, an amplified product is cloned into a plasmid such as pBluescript SK (−) (manufactured by Stratagene) or the like, and the nucleotide sequence is determined according to a method similar to the method described in the above (2) to obtain a plasmid having a DNA sequence encoding the amino acid sequence of VH or VL of a desired human CDR-grafted antibody.

(5) Modification of Amino Acid Sequence of V Region of Human CDR-Grafted Antibody It is known that when a human CDR-grafted antibody is produced by simply grafting only CDRs in VH and VL of an antibody derived from a non-human animal into FRs of VH and VL of a human antibody, its antigen binding activity is lower than that of the original antibody derived from a non-human animal [BIO/TECHNOLOGY, 9, 266 (1991)]. In human CDR-grafted antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original non-human antibody to thereby increase the antigen binding activity which has been decreased.

In order to identify the amino acid residues relating to the antigen binding activity in FR, the three-dimensional structure of an antibody is constructed and analyzed by X-ray crystallography [*J Mol. Biol.*, 112, 535 (1977)], computer-modeling [*Protein Engineering*, 7, 1501 (1994)] or the like. In addition, the modified human CDR-grafted antibody having a required antigen binding activity can be obtained through various attempts that several modified antibodies of each antibody are produced and the correlation between each of the modified antibodies and its antibody binding activity is examined and through trial and error process.

The modification of the amino acid sequence of FR in VH and VL of a human antibody can be accomplished using various synthetic DNA for modification according to PCR as described in the above (4). With regard to the amplified product obtained by the PCR, the nucleotide sequence is determined according to the method as described in the above (2) so that whether the objective modification has been carried out is confirmed.

(6) Construction of Vector for Expression of Human CDR-Grafted Antibody

A vector for expression of human CDR-grafted antibody can be constructed by cloning each cDNA encoding VH or VL of a constructed recombinant antibody into upstream of each gene encoding CH or CL of the human antibody in the vector for expression of human CDR-grafted antibody obtained in the above (1).

For example, when recognizing sequences of an appropriate restriction enzymes are introduced to the 5'-terminal of synthetic DNAs positioned at both ends among synthetic DNAs used in the construction of VH or VL of the human CDR-grafted antibody obtained in the above (4) and (5), cloning can be carried out so that they are expressed in an appropriate form in the upstream of each gene encoding CH or CL of the human antibody in the vector for expression of human CDR-grafted antibody obtained in the above (1).

(7) Transient Expression of Recombinant Antibody

In order to efficiently evaluate the antigen binding activity of various human CDR-grafted antibodies produced, the recombinant antibodies can be expressed transiently using the vector for expression of human CDR-grafted antibody obtained in the above (3) and (6) or the modified expression vector thereof.

Any cell can be used as a host cell, so long as the host cell can express a recombinant antibody. Generally, COS-7 cell (ATCC CRL1651) is used [*Methods in Nucleic Acids Res.*, CRC Press, 283 (1991)].

Examples of the method for introducing the expression vector into COS-7 cell include a DEAE-dextran method [*Methods in Nucleic Acids Res.*, CRC Press, 283 (1991)], a lipofection method [*Proc. Natl. Acad. Sci. USA*, 84, 7413 (1987)], and the like.

After introduction of the expression vector, the expression amount and antigen binding activity of the recombinant antibody in the culture supernatant can be determined by the enzyme-linked immunosorbent assay [*Monoclonal Antibodies—Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

(8) Obtaining a Transformant Stably Expressing a Recombinant Antibody and Preparation of the Recombinant Antibody A transformant which stably expresses a recombinant antibody can be obtained by introducing the vector for expression of recombinant antibody obtained in the above (3) and (6) into an appropriate host cell.

Examples of the method for introducing the expression vector into a host cell include electroporation [Japanese Published Unexamined Patent Application No. 257891/90, *Cytotechnology*, 3, 133 (1990)] and the like.

As the host cell into which a vector for expression of recombinant is introduced, any cell can be used, so long as it is a host cell which can produce the recombinant antibody. Examples include CHO-K1 (ATCC CCL-61), DUkXB11 (ATCC CCL-9096), Pro-5 (ATCC CCL-1781), CHO-S (Life Technologies, Cat #11619), rat myeloma cell YB2/3HL.P2.G11.16Ag.20 (hereinafter, also referred to as YB2/0), mouse myeloma cell NSO, mouse myeloma cell SP2/0-Ag14 (ATCC CRL1581), mouse P3×63-AG8.653 cell (ATCC CRL1580), CHO cell in which a dihydrofolate reductase gene (hereinafter referred to as "dhfr") is defective [*Proc. Natl. Acad. Sci. U.S.A.*, 77, 4216 (1980)], lection resistance-acquired Lec13 [*Somatic Cell and Molecular genetics*, 12, 55 (1986)], CHO cell in which α-1,6-fucosyltransaferse gene is defected (WO 05/35586), rat YB2/3HL.P2.G11.16Ag.20 cell (ATCC CRL1662), and the like.

After introduction of the expression vector, transformants which express a recombinant antibody stably are selected by culturing in a medium for animal cell culture containing an agent such as G418 sulfate (hereinafter referred to as "G418") or the like (Japanese Published Unexamined Patent Application No. 257891/90).

Examples of the medium for animal cell culture include RPMI1640 medium (manufactured by Invitrogen), GIT medium (manufactured by Nissui Pharmaceutical), EX-CELL301 medium (manufactured by JRH), IMDM medium (manufactured by Invitrogen), Hybridoma-SFM medium (manufactured by Invitrogen), media obtained by adding various additives such as FBS to these media, and the like. The recombinant antibody can be produced and accumulated in a culture supernatant by culturing the selected transformants in a medium. The expression amount and antigen binding activity of the recombinant antibody in the culture supernatant can be measured by ELISA or the like. Also, in the transformant, the expression amount of the recombinant antibody can be increased by using DHFR amplification system or the like according to the method disclosed in Japanese Published Unexamined Patent Application No. 257891/90.

3. Purification of Monoclonal Antibody

The recombinant antibody can be purified from the culture supernatant of the transformant by using a protein A column [*Monoclonal Antibodies—Principles and practice*, Third edition, Academic Press (1996), *Antibodies—A Laboratory Manual*, Cold Spring Harbor Laboratory (1988)]. Any other conventional methods for protein purification can be used.

The molecular weight of the H chain or the L chain of the purified recombinant antibody or the antibody molecule as a whole is determined by polyacrylamide gel electrophoresis [*Nature*, 227, 680 (1970)], Western blotting [*Monoclonal Antibodies—Principles and practice*, Third edition, Academic Press (1996), *Antibodies—A Laboratory Manual*, Cold Spring Harbor Laboratory (1988)], and the like.

4. Activity Evaluation of the Purified Antibody

The activity of the purified antibody of the present invention can be evaluated in the following manner.

The binding activity to a CD40-expressing cell is evaluated by the binding assay described in the above 1-(6) or a surface plasmon resonance method using such as BIAcore system. Furthermore, it can be measured by fluorescent antibody technique [*Cancer Immunol. Immunother*, 36, 373 (1993)] or the like.

In addition, CDC activity or ADCC activity against an antigen positive cell line is evaluated by a known method [*Cancer Immunol. Immunother*, 36, 373 (1993)].

In the present invention, an agonist activity can be measured by a variety of assays. For example, as illustrated in Examples which will follow, a method may be exemplified which measures the promotion of CD95 expression by an anti-CD40 antibody using Ramos cells.

4. Method of Controlling Effector Activity of Antibody

As a method of controlling an effector activity of the monoclonal antibody of the present invention, there are known a method of controlling an amount of fucose (hereinafter, referred to also as "core fucose") which is bound in α-1,6 linkage to N-acetylglucosamine (GlcNAc) present in a reducing end of a complex type N-linked sugar chain which is bound to asparagine (Asn) at position 297 of an Fc region of an antibody (WO2005/035586, WO2002/31140, and WO00/61739), a method of controlling an effector activity of a monoclonal antibody by modifying amino acid group(s) of an Fc region of the antibody, and the like.

The "effector activity" means an antibody-dependent activity that occurs through an Fc region of an antibody. As the effector activity, there are known antibody-dependent cellular cytotoxicity (ADCC activity), complement-dependent cytotoxicity (CDC activity), antibody-dependent phagocytosis (ADP activity) by phagocytic cells such as macrophages or dendritic cells, and the like.

By controlling a content of core fucose of a complex type N-linked sugar chain of Fc of an antibody, an effector activity of the antibody can be increased or decreased. According to a method of lowering a content of fucose which is bound to a complex type N-linked sugar chain bound to Fc of the antibody, an antibody to which fucose is not bound can be obtained by the expression of an antibody using a CHO cell which is deficient in a gene encoding α-1,6-fucosyltransferase. The antibody to which fucose is not bound has a high ADCC activity. On the other hand, according to a method of increasing a content of fucose which is bound to a complex type N-linked sugar chain bound to Fc of an antibody, an antibody to which fucose is bound can be obtained by the expression of an antibody using a host cell into which a gene encoding α-1,6-fucosyltransferase is introduced. The antibody to which fucose is bound has a lower ADCC activity than the antibody to which fucose is not bound.

Further, by modifying amino acid residue(s) of an Fc region of an antibody, an ADCC activity or CDC activity can be increased or decreased. Because it is known that an ADCC or CDC activity is variable according to a subclass of an antibody, it is considered that the ADCC or CDC activity can be decreased by the mutation of an antibody subclass. For example, generally among human IgG subclasses, IgG4 is known as a subclass having low ADCC and CDC activities, IgG2 has a CDC activity but with a low ADCC activity, and IgG1 has been reported to have both high ADCC and CDC activities (Charles A. Janeway et al., Immunobiology, 1997, Current Biology Ltd/Garland Publishing Inc.). Taking advantage of these characteristics, an antibody with less cellular cytotoxicity can be obtained by selecting a particular subclass. Further, an antibody having a desired activity can be prepared by a combination of a particular subclass of an antibody with point mutations. Furthermore, an antibody having a desired activity can be prepared by combining an antibody comprising a specific subclass and a point mutation.

Other than the above substitutions, such as (i) the substitution of V234A and G237A (figures are based on the EU index as in Kabat et al.) into IgG2 subclass (Michael, S., et al., *J. Immunol.*, 1997, 159; 3613) and (ii) substitution of D270, K322, P329, or P331 with A or substitution of P331 with S or G (Esohe E. Idusogie et al. *J. Biol. Chem.* 1994, 269:3469-3474, Yuanyuan Xu et al. *J. Biol. Chem.* 1994, 269: 3469-3474; Brekke, O. H. et al. *Eur. J. Immunol.* 1994, 24: 2542; Morgan, A., et al., Immunology 1995, 86: 319; Lund, J., et al., *J. Immunol.*, 1996, 157: 4963; and Tao, M. H., et al., *J. Exp. Med.* 1993, 178: 661), the following examples can be cited.

Glu233-Ser239, Gly316-Lys338, Lys274-Arg301, Tyr407-Arg416, Asn297, Glu318, Leu234-Ser239, Asp265-Glu269, Asn297-Thr299, and Ala327-Ile332 are thought to be involved in the binding between IgG and FcR (Duncan, A. R., Woof, J. M., Partridge, L. J., Burton, D. R., and Winter, G (1988) *Nature* 332, 563-564; Gessner, J. E., Heiken, H., Tamm, A., and Schmidt, R. E. (1998) *Ann. Hematol.* 76, 231-248; Gavin, A., Hulett, M., and Hogarth, P. M. (1998) in *The Immunoglobulin Receptors and Their Physiological and Pathological Roles in Immunity* (van de Winkel, J. G. J., and Hogarth, P. M., eds), pp. 11-35; Kluwer Academic Publishers Group, Dordrecht, The Netherlands, Sautes, C. (1997) in *Cell-mediated Effects of Immunoglobulins* (Fridman, W. H., and Sautes, C., eds), pp. 29-66; R. G Landes Co., Austin, Tex., Da'ron, M. (1997) *Annu. Rev. Immunol.* 15, 203-234; Canfield, S. M., and Morrison, S. L. (1991) *J. Exp. Med.* 173, 1483-1491; Chappel, M. S., Isenman, D. E., Everett, M., Xu, Y.-Y., Dorrington, K. J., and Klein, M. H. (1991) *Proc. Natl. Acad. Sci. U.S.A.* 88, 9036-9040; Woof, J. M., Partridge, L. J., Jefferis, R., and Burton, D. R. (1986) *Mol. Immunol.* 23, 319-330; and Wines, B. D., Powell, M. S., Parren, P. W. H. I., Barnes, N., and Hogarth, P. M. (2000) *J. Immunol.* 164, 5313-5318). By introducing mutation into such regions, ADCC activity can be reduced. Specifically, FcR-binding ability can be reduced by substituting L235 with E and A, respectively.

Alternatively, an antibody in which the effector activity of the antibody is controlled can be obtained by using a combination of the above-mentioned point mutations in one antibody.

Since an anti-CD40 antibody having an agonist activity has an ability to activate immune and therefore can be used in a therapeutic agent for a variety of diseases, it is considered to be preferable of the antibody has no or decreased ADCC and CDC activity leading to cell death of CD40-expressing cells due to the activation. If CD40-expressing cells are damaged by an ADCC activity or CDC activity, it is considered that there are a possibility of an immune suppression state contrary to expected immune activation, and a possibility of causing a worsening of the disease (Charles A. Janeway et al., *Immunology*, 1997, Current Biology Ltd./Garland Publishing Inc.). By using this feature to select an antibody comprising a specific subclass, an antibody having a reduced cytotoxicity can be prepared.

5. Method for Treating the Diseases Using the Anti-Cd40 Antibody of the Present Invention The monoclonal antibody of the present invention can be used for treating malignant tumor or infection.

The therapeutic agent comprising the monoclonal antibody of the present invention may be only the antibody as an active ingredient, and is preferably supplied as a pharmaceutical preparation produced by an appropriate method well known in the technical field of pharmaceutics, by mixing it with one or more pharmaceutically acceptable carriers.

It is preferred to select a route of administration which is most effective in treatment. Examples include oral administration and parenteral administration, such as buccal, tracheal, rectal, subcutaneous, intramuscular or intravenous administration. In the case of an antibody or peptide formulation, intravenous administration is preferred. The dosage form includes sprays, capsules, tablets, granules, syrups, emulsions, suppositories, injections, ointments, tapes and the like.

The pharmaceutical preparation suitable for oral administration includes emulsions, syrups, capsules, tablets, powders, granules and the like.

Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like.

Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like.

Injections can be prepared using a carrier such as a salt solution, a glucose solution or a mixture of both thereof.

Suppositories can be prepared using a carrier such as cacao butter, hydrogenated fat or carboxylic acid.

Sprays can be prepared using the antibody or antibody fragment as such or using it together with a carrier which does not stimulate the buccal or airway mucous membrane of the patient and can facilitate absorption of the compound by dispersing it as fine particles. The carrier includes lactose, glycerol and the like. Depending on the properties of the antibody and the carrier, it is possible to produce pharmaceutical preparations such as aerosols and dry powders.

In addition, the components exemplified as additives for oral preparations can also be added to the parenteral preparations.

5. Method for Diagnosing the Disease Using the Anti-Cd40 Antibody of the Present Monoclonal Antibody A disease relating to CD40 can be diagnosed by detecting or measuring CD40 or CD40 expressing cell using the monoclonal antibody of the present invention.

A diagnosis of cancer, one of the diseases relating to CD40, can be carried out by, for example, the detection or measurement of CD40 as follows.

The diagnosis can be done by detecting CD40 which expresses in cancer cells in a patient's body using an immunological method such as a flow cytometry.

An immunological method is a method in which an antibody amount or an antigen amount is detected or determined using a labeled antigen or antibody. Examples of the immunological method include radioactive substance-labeled immunoantibody method, enzyme immunoassay, fluorescent immunoassay, luminescent immunoassay, Western blotting method, physicochemical means and the like.

As a method for detection or determination of the amount of CD40 in the present invention, any known method may be included. For example, an immunological detection method or immunoassay may be exemplified.

Examples of the radioactive substance-labeled immunoantibody method include a method, in which the antibody of the present invention is allowed to react with an antigen or a cell expressing an antigen, then anti-immunoglobulin antibody subjected to radioactive labeling or a binding fragment thereof is allowed to react therewith, followed by determination using a scintillation counter or the like.

Examples of the enzyme immunoassay include a method, in which the antibody of the present invention is allowed to react with an antigen or a cell expressing an antigen, then an anti-immunoglobulin antibody or an binding fragment thereof subjected to antibody labeling is allowed to react therewith and the colored pigment is measured by a spectrophotometer, and, for example, sandwich ELISA may be used. As a label used in the enzyme immunoassay, any known enzyme label [*Enzyme Immunoassay*, published by Igaku Shoin (1987)] can be used as described already. Examples include alkaline phosphatase labeling, peroxidase labeling, luciferase labeling, biotin labeling and the like.

Sandwich ELISA is a method in which an antibody is bound to a solid phase, antigen to be detected or measured is trapped and another antibody is allowed to react with the trapped antigen. In the ELISA, 2 kinds of antibody which recognizes the antigen to be detected or measured or the antibody fragment thereof in which antigen recognizing site is different are prepared and one antibody or antibody fragments is previously adsorbed on a plate (such as a 96-well plate) and another antibody or antibody fragment is labeled with a fluorescent substance such as FITC, an enzyme such as peroxidase, or biotin. The plate to which the above antibody is adsorbed is allowed to react with the cell separated from living body or disrupted cell suspension thereof, tissue or disintegrated solution thereof, cultured cells, serum, pleural effusion, ascites, eye solution or the like, then allowed to react with labeled monoclonal antibody or antibody fragment and a detection reaction corresponding to the labeled substance is carried out. When an antigen concentration in the sample to be tested is measured by the method, antigen concentration in the sample to be tested can be calculated from a calibration curve prepared by a stepwise dilution of antigen of known concentration. As antibody used for sandwich ELISA, any of polyclonal antibody and monoclonal antibody may be used or antibody fragments such as Fab, Fab' and F(ab)$_2$ may be used. As a combination of 2 kinds of antibodies used in sandwich ELISA, a combination of monoclonal antibodies or antibody fragments recognizing different epitopes may be used or a combination of polyclonal antibody with monoclonal antibody or antibody fragments may be used.

A fluorescent immunoassay includes a method described in the literatures [*Monoclonal Antibodies—Principles and practice*, Third Edition, Academic Press (1996); *Manual for Monoclonal Antibody Experiments*, Kodansha Scientific (1987)] and the like. As a label for the fluorescent immunoassay, any of known fluorescent labels (*Fluorescent Immunoassay*, Soft Science, (1983)) may be used as described already. Examples include FITC, RITC and the like.

The luminescent immunoassay can be carried out using the methods described in the literature [*Bioluminescence and Chemical Luminescence*, Rinsho Kensa, 42, Hirokawa Shoten (1998)] and the like. As a label used for luminescent immunoassay, any of known luminescent labels can be included. Examples include acridinium ester, lophine or the like may be used.

Western blotting is a method in which an antigen or a cell expressing an antigen is fractionated by SDS-polyacrylamide gel electrophoresis [*Antibodies—A Laboratory Manual* (Cold Spring Harbor Laboratory, 1988)], the gel is blotted onto PVDF membrane or nitrocellulose membrane, the membrane is allowed to react with antigen-recognizing antibody or antibody fragment, further allowed to react with an anti-mouse IgG antibody or antibody fragment which is labeled with a fluorescent substance such as FITC, an enzyme label such as peroxidase, a biotin labeling, or the like, and the label is visualized to confirm the reaction. An example of Western blotting is described below.

Cells or tissues in which CD40 is expressed are dissolved in a solution and, under reducing conditions, 0.1 to 30 µg as a protein amount per lane is electrophoresed by an SDS-PAGE method. The electrophoresed protein is transferred to a PVDF membrane and allowed to react with PBS containing 1 to 10% of BSA (hereinafter referred to as "BSA-PBS") at room temperature for 30 minutes for blocking. Here, the monoclonal antibody of the present invention is allowed to react therewith, washed with PBS containing 0.05 to 0.1% Tween 20 (hereinafter referred to as "Tween-PBS") and allowed to react with goat anti-mouse IgG labeled with peroxidase at room temperature for 2 hours. It is washed with Tween-PBS and a band to which the monoclonal antibody is bound is detected using ECL™ Western Blotting Detection Reagents (manufactured by Amersham) or the like to thereby detect CD40. As an antibody used for the detection in Western blotting, an antibody which can be bound to a polypeptide having no three-dimensional structure of a natural type is used.

The physicochemical method is specifically carried out using the antibody or antibody fragment of the present invention by reacting CD40 as the antigen with the antibody of the present invention to form an aggregate, and detecting this aggregate. Other examples of the physicochemical methods include a capillary method, a one-dimensional immunodiffusion method, an immunoturbidimetry and a latex immunoturbidimetry [*Handbook of Clinical Test Methods*, Kanehara Shuppan, 499 (1988)].

For example, in a latex immunodiffusion method, a carrier such as polystyrene latex having a particle size of about of 0.1 to 1 µm sensitized with antibody or antigen may be used and when an antigen-antibody reaction is carried out using the corresponding antigen or antibody, scattered light in the reaction solution increases while transmitted light decreases. When such a change is detected as absorbance or integral sphere turbidity, it is now possible to measure antigen concentration, etc. in the sample to be tested.

For the detection of the cell expressing CD40, known immunological detection methods can be used, and an immunoprecipitation method, a fluorescent cell staining method, an immune tissue staining method and the like are preferably used.

The above-described antibody or antibody fragment of the present invention is solid-phased on a 96-well plate for ELISA and then blocked with BSA-PBS. When the antibody is in a non-purified state such as a culture supernatant of hybridoma cell, anti-mouse immunoglobulin or rat immunoglobulin or protein A or G or the like is previously adsorbed on a 96-well plate for ELISA and blocked with BSA-PBS and a culture supernatant of hybridoma cell is dispensed thereto for binding. After BSA-PBS is discarded and the residue is sufficiently washed with PBS, reaction is carried out with a dissolved solution of cells or tissues expressing CD40. An immune precipitate is extracted from the well-washed plate with a sample buffer for SDS-PAGE and detected by the above-described Western blotting.

An immune cell staining method and an immune tissue staining method are immunofluorescent staining methods (a flow cytometry) where cells or tissues in which antigen is expressed are treated, if necessary, with a surfactant or methanol to make an antibody easily permeate to the cells or tissues, then the antibody of the present invention is allowed to react therewith, then further allowed to react with an anti-immunoglobulin antibody or binding fragment thereof subjected to fluorescent labeling such as FITC, enzyme label such as peroxidase or biotin labeling and the label is visualized and observed under a microscope or cells are allowed to react with a fluorescence-labeled antibody and analyzed by a flow cytometer. That can be carried out by the methods described, for example, in the literatures [*Monoclonal Antibodies—Principles and practice*, Third Edition, Academic Press (1996), *Manual for Experiments of Monoclonal Antibodies*, Kodansha Scientific (1987)]. Particularly, since the antibody or antibody fragment of the present invention binds to three-dimensional structure of an extracellular region of CD40, it can be preferably used for detection of a cell expressing the polypeptide maintaining a natural type three-dimensional structure by a flow cytometry.

In addition, by using FMAT8100HTS system (manufactured by Applied Biosystems) which utilizes the principle of fluorescent antibody staining, the antigen quantity or antibody quantity can be measured without separating the formed antibody-antigen complex and the free antibody or antigen which is not concerned in the formation of the antibody-antigen complex.

Specific examples are described below (the signal region is estimated by SignalPver.3. In addition, the CDR region is decided in accordance with the rule by Kabat et al.).

1. IgG2-AAS (341) Antibody

```
(1) DNA sequence of heavy chain
                                              (SEQ ID NO: 1)
ATGTCTGTCT CCTTCCTCAT CTTCCTGCCC GTGCTGGGCC

TCCCATGGGG TGTCCTGTCA CAGGTCCAAC TGCAGCAGTC

AGGTCCAGGA CTGGTGAAGC CCTCGCAGAC CCTCTCACTC

ACCTGTGCCA TCTCCGGGGA CAGTGTCTCT AGCAACAGTG

CTACTTGGAA CTGGATCAGG CAGTCCCCAT CGAGAGACCT

TGAGTGGCTG GGAAGGACAT ACTACAGGTC CAAGTGGTAT

CGTGATTATG TAGGATCTGT GAAAAGTCGA ATAATCATCA

ACCCAGACAC ATCCAACAAC CAGTTCTCCC TGCAGCTGAA

CTCTGTGACT CCCGAGGACA CGGCTATATA TTACTGTACA

AGAGCACAGT GGCTGGGAGG GGATTACCCC TACTACTACA

GTATGGACGT CTGGGGCCAA GGGACCACGG TCACCGTCTC

CTCAGCTAGC ACCAAGGGCC CATCGGTCTT CCCCCTGGCG

CCCTGCTCCA GGAGCACCTC CGAGAGCACA GCGGCCCTGG

GCTGCCTGGT CAAGGACTAC TTCCCCGAAC CGGTGACGGT

GTCGTGGAAC TCAGGCGCTC TGACCAGCGG CGTGCACACC

TTCCCAGCTG TCCTACAGTC CTCAGGACTC TACTCCCTCA

GCAGCGTGGT GACCGTGCCC TCCAGCAACT TCGGCACCCA

GACCTACACC TGCAACGTAG ATCACAAGCC CAGCAACACC

AAGGTGGACA AGACAGTTGA GCGCAAATGT TGTGTCGAGT

GCCCACCGTG CCCAGCACCA CCTGCAGCAG CACCGTCAGT

CTTCCTCTTC CCCCCAAAAC CCAAGGACAC CCTCATGATC

TCCCGGACCC CTGAGGTCAC GTGCGTGGTG GTGGACGTGA

GCCACGAAGA CCCCGAGGTC CAGTTCAACT GGTACGTGGA

CGGCGTGGAG GTGCATAATG CCAAGACAAA GCCACGGGAG

GAGCAGTTCA ACAGCACGTT CCGTGTGGTC AGCGTCCTCA

CCGTTGTGCA CCAGGACTGG CTGAACGGCA AGGAGTACAA

GTGCAAGGTC TCCAACAAAG GCCTCCCAGC CTCCATCGAG

AAAACCATCT CCAAAACCAA AGGGCAGCCC CGAGAACCAC

AGGTGTACAC CCTGCCCCCA TCCCGGGAGG AGATGACCAA

GAACCAGGTC AGCCTGACCT GCCTGGTCAA AGGCTTCTAC

CCCAGCGACA TCGCCGTGGA GTGGGAGAGC AATGGGCAGC

CGGAGAACAA CTACAAGACC ACACCTCCCA TGCTGGACTC

CGACGGCTCC TTCTTCCTCT ACAGCAAGCT CACCGTGGAC

AAGAGCAGGT GGCAGCAGGG GAACGTCTTC TCATGCTCCG

TGATGCATGA GGCTCTGCAC AACCACTACA CGCAGAAGAG

CCTCTCCCTG TCTCCGGGTA AA
```

(i) Signal: A at position 1 to A at position 60
(ii) Variable region: C at position 61 to A at position 444
    CDR1: A at position 151 to C at position 171
    CDR2: A at position 214 to T at position 267
    CDR3: G at position 364 to C at position 411
(iii) Constant region: G at position 445 to A at position 1422
    position 234 which is indicated by the EU index as in Kabat et al.: G at position 784 to A at position 786
    position 237 which is indicated by the EU index as in Kabat et al.: G at position 790 to A at position 792
    position 331 which is indicated by the EU index as in Kabat et al.: T at position 1072 to C at position 1074

```
(2) Amino acid sequence of heavy chain
                                              (SEQ ID NO: 2)
MSVSFLIFLP VLGLPWGVLS QVQLQQSGPG LVKPSQTLSL

TCAISGDSVS SNSATWNWIR QSPSRDLEWL GRTYYRSKWY

RDYVGSVKSR IIINPDTSNN QFSLQLNSVT PEDTAIYYCT

RAQWLGGDYP YYYSMDVWGQ GTTVTVSSAS TKGPSVFPLA

PCSRSTSEST AALGCLVKDY FPEPVTVSWN SGALTSGVHT

FPAVLQSSGL YSLSSVVTVP SSNFGTQTYT CNVDHKPSNT

KVDKTVERKC CVECPPCPAP PAAAPSVFLF PPKPKDTLMI

SRTPEVTCVV VDVSHEDPEV QFNWYVDGVE VHNAKTKPRE

EQFNSTFRVV SVLTVVHQDW LNGKEYKCKV SNKGLPASIE

KTISKTKGQP REPQVYTLPP SREEMTKNQV SLTCLVKGFY

PSDIAVEWES NGQPENNYKT TPPMLDSDGS FFLYSKLTVD

KSRWQQGNVF SCSVMHEALH NHYTQKSLSL SPGK*
```

(i) Signal: M at position 1 to S at position 20
(ii) Variable region: Q at position 21 to S at position 148
    CDR1: S at position 51 to N at position 57
    CDR2: R at position 72 to S at position 89
    CDR3: A at position 122 to V at position 137
(iii) Constant region: A at position 149 to A at position 474
    position 234 which is indicated by the EU index as in Kabat et al.: A at position 262
    position 237 which is indicated by the EU index as in Kabat et al.: A at position 264 position 331 which is indicated by the EU index as in Kabat et al.: S at position 358

```
(3) DNA sequence of light chain
                                        (SEQ ID NO: 11)
ATGGAAGCCC CAGCTCAGCT TCTCTTCCTC CTGCTACTCT

GGCTCCCAGA TACCACCGGA GAAATTGTGT TGACACAGTC

TCCAGCCACC CTGTCTTTGT CTCCAGGGGA AAGAGCCACC

CTCTCCTGCA GGGCCAGTCA GAGTGTTAGC AGCTACTTAG

CCTGGTACCA ACAGAAACCT GGCCAGGCTC CCAGGCTCCT

CATCTATGAT GCATCCAACA GGGCCACTGG CATCCCAGCC

AGGTTCAGTG GCAGTGGGTC TGGGACAGAC TTCACTCTCA

CCATCAGCAG CCTAGAGCCT GAAGATTTTG CAGTTTATTA

CTGTCAGCAG CGTAGCAACA CTTTCGGCCC TGGGACCAAA

GTGGATATCA AACGTACGGT GGCTGCACCA TCTGTCTTCA

TCTTCCCGCC ATCTGATGAG CAGTTGAAAT CTGGAACTGC

CTCTGTTGTG TGCCTGCTGA ATAACTTCTA TCCCAGAGAG

GCCAAAGTAC AGTGGAAGGT GGATAACGCC CTCCAATCGG

GTAACTCCCA GGAGAGTGTC ACAGAGCAGG ACAGCAAGGA

CAGCACCTAC AGCCTCAGCA GCACCCTGAC GCTGAGCAAA

GCAGACTACG AGAAACACAA AGTCTACGCC TGCGAAGTCA

CCCATCAGGG CCTGAGCTCG CCCGTCACAA AGAGCTTCAA

CAGGGGAGAG TGT
```

(i) Signal: A at position 1 to A at position 60
(ii) Variable region: G at position 61 to A at position 372
   CDR1: A at position 130 to C at position 162
   CDR2: A at position 208 to T at position 228
   CDR3: C at position 325 to T at position 342
(iii) Constant region: C at position 373 to T at position 693

```
(4) Amino acid sequence of light chain
                                        (SEQ ID NO: 12)
MEAPAQLLFL LLLWLPDTTG EIVLTQSPAT LSLSPGERAT

LSCRASQSVS SYLAWYQQKP GQAPRLLIYD ASNRATGIPA

RFSGSGSGTD FTLTISSLEP EDFAVYYCQQ RSNTFGPGTK

VDIKRTVAAP SVFIFPPSDE QLKSGTASVV CLLNNFYPRE

AKVQWKVDNA LQSGNSQESV TEQDSKDSTY SLSSTLTLSK

ADYEKHKVYA CEVTHQGLSS PVTKSFNRGE C*
```

(i) Signal: M at position 1 to G at position 20
(ii) Variable region: E at position 21 to K at position 124
   CDR1: R at position 44 to A at position 54
   CDR2: D at position 70 to T at position 76
   CDR3: Q at position 109 to T at position 114
(iii) Constant region: R at position 125 to C at position 231

2. IgG2-AAS (21.4.1) Antibody

```
(1) DNA sequence of heavy chain
                                        (SEQ ID NO: 21)
ATGGACTGGA CCTGGAGGAT CCTCTTCTTG GTGGCAGCAG

CCACAGGAGC CCACTCCCAG GTGCAGCTGG TGCAGTCTGG

GGCTGAGGTG AAGAAGCCTG GGGCCTCAGT GAAGGTCTCC

TGCAAGGCTT CTGGATACAC CTTCACCGGC TACTATATGC

ACTGGGTGCG ACAGGCCCCT GGACAAGGGC TTGAgtGGAT

GGGATGGATC AACCCTGACA GTGGTGGCAC AAACTATGCA

CAGAAGTTTC AGGGCAGGGT CACCATGACC AGGGACACGT

CCATCAGCAC AGCCTACATG GAGCTGAACA GGCTGAGATC

TGACGACACG GCCGTGTATT ACTGTGCGAG AGATCAGCCC

CTAGGATATT GTACTAATGG TGTATGCTCC TACTTTGACT

ACTGGGGCCA GGGAACCCTG GTCACCGTCT CCTCAGCTAG

CACCAAGGGC CCATCGGTCT TCCCCCTGGC GCCCTGCTCC

AGGAGCACCT CCGAGAGCAC AGCGGCCCTG GGCTGCCTGG

TCAAGGACTA CTTCCCCGAA CCGGTGACGG TGTCGTGGAA

CTCAGGCGCT CTGACCAGCG GCGTGCACAC CTTCCCAGCT

GTCCTACAGT CCTCAGGACT CTACTCCCTC AGCAGCGTGG

TGACCGTGCC CTCCAGCAAC TTCGGCACCC AGACCTACAC

CTGCAACGTA GATCACAAGC CCAGCAACAC CAAGGTGGAC

AAGACAGTTG AGCGCAAATG TTGTGTCGAG TGCCCACCGT

GCCCAGCACC ACCTGCAGCA GCACCGTCAG TCTTCCTCTT

CCCCCCAAAA CCCAAGGACA CCCTCATGAT CTCCCGGACC

CCTGAGGTCA CGTGCGTGGT GGTGGACGTG AGCCACGAAG

ACCCCGAGGT CCAGTTCAAC TGGTACGTGG ACGGCGTGGA

GGTGCATAAT GCCAAGACAA AGCCACGGGA GGAGCAGTTC

AACAGCACGT TCCGTGTGGT CAGCGTCCTC ACCGTTGTGC

ACCAGGACTG GCTGAACGGC AAGGAGTACA AGTGCAAGGT

CTCCAACAAA GGCCTCCCAG CCTCCATCGA GAAAACCATC

TCCAAAACCA AAGGGCAGCC CCGAGAACCA CAGGTGTACA

CCCTGCCCCC ATCCCGGGAG GAGATGACCA AGAACCAGGT

CAGCCTGACC TGCCTGGTCA AAGGCTTCTA CCCCAGCGAC

ATCGCCGTGG AGTGGGAGAG CAATGGGCAG CCGGAGAACA

ACTACAAGAC CACACCTCCC ATGCTGGACT CCGACGGCTC

CTTCTTCCTC TACAGCAAGC TCACCGTGGA CAAGAGCAGG

TGGCAGCAGG GGAACGTCTT CTCATGCTCC GTGATGCATG

AGGCTCTGCA CAACCACTAC ACGCAGAAGA GCCTCTCCCT

GTCTCCGGGT AAA
```

(i) Signal: A at position 1 to C at position 57
(ii) Variable region: C at position 58 to A at position 435
(iii) Constant region: G at position 436 to A at position 1413
   position 234 which is indicated by the EU index as in Kabat et al.: G at position 775 to A at position 777
   position 237 which is indicated by the EU index as in Kabat et al.: G at position 781 to A at position 783 position 331 which is indicated by the EU index as in Kabat et al.: T at position 1063 to C at position 1065

```
(2) Amino acid sequence of heavy chain
                                         (SEQ ID NO: 22)
MDWTWRILFL VAAATGAHSQ VQLVQSGAEV KKPGASVKVS

CKASGYTFTG YYMHWVRQAP GQGLEWMGWI NPDSGGTNYA

QKFQGRVTMT RDTSISTAYM ELNRLRSDDT AVYYCARDQP

LGYCTNGVCS YFDYWGQGTL VTVSSASTKG PSVFPLAPCS

RSTSESTAAL GCLVKDYFPE PVTVSWNSGA LTSGVHTFPA

VLQSSGLYSL SSVVTVPSSN FGTQTYTCNV DHKPSNTKVD

KTVERKCCVE CPPCPAPPAA APSVFLFPPK PKDTLMISRT

PEVTCVVVDV SHEDPEVQFN WYVDGVEVHN AKTKPREEQF

NSTFRVVSVL TVVHQDWLNG KEYKCKVSNK GLPASIEKTI

SKTKGQPREP QVYTLPPSRE EMTKNQVSLT CLVKGFYPSD

IAVEWESNGQ PENNYKTTPP MLDSDGSFFL YSKLTVDKSR

WQQGNVFSCS VMHEALHNHY TQKSLSLSPG K*
```

(i) Signal: M at position 1 to S at position 19
(ii) Variable region: Q at position 20 to S at position 145
(iii) Constant region: A at position 146 to K at position 471
   position 234 which is indicated by the EU index as in Kabat et al.: A at position 259
   position 237 which is indicated by the EU index as in Kabat et al.: A at position 261
   position 331 which is indicated by the EU index as in Kabat et al.: S at position 355

```
(3) DNA sequence of light chain
                                         (SEQ ID NO: 25)
ATGAGGCTCC CTGCTCAGCT CCTGGGGCTC CTGCTGCTCT

GGTTCCCAGG TTCCAGATGC GACATCCAGA TGACCCAGTC

TCCATCTTCC GTGTCTGCAT CTGTAGGAGA CAGAGTCACC

ATCACTTGTC GGGCGAGTCA GGGTATTTAC AGCTGGTTAG

CCTGGTATCA GCAGAAACCA GGGAAAGCCC CTAACCTCCT

GATCTATACT GCATCCACTT TACAAAGTGG GGTCCCATCA

AGGTTCAGCG GCAGTGGATC TGGGACAGAT TTCACTCTCA

CCATCAGCAG CCTGCAACCT GAAGATTTTG CAACTTACTA

TTGTCAACAG GCTAACATTT TCCCGCTCAC TTTCGGCGGA

GGGACCAAGG TGGAGATCAA ACGTACGGTG GCTGCACCAT

CTGTCTTCAT CTTCCCGCCA TCTGATGAGC AGTTGAAATC

TGGAACTGCC TCTGTTGTGT GCCTGCTGAA TAACTTCTAT

CCCAGAGAGG CCAAAGTACA GTGGAAGGTG GATAACGCCC

TCCAATCGGG TAACTCCCAG GAGAGTGTCA CAGAGCAGGA

CAGCAAGGAC AGCACCTACA GCCTCAGCAG CACCCTGACG

CTGAGCAAAG CAGACTACGA GAAACACAAA GTCTACGCCT

GCGAAGTCAC CCATCAGGGC CTGAGCTCGC CGTCACAAA

GAGCTTCAAC AGGGGAGAGT GT
```

(i) Signal: A at position 1 to C at position 60
(ii) Variable region: G at position 61 to T at position 384
(iii) Constant region: A at position 385 to T at position 702

```
(4) Amino acid sequence of light chain
                                         (SEQ ID NO: 26)
MRLPAQLLGL LLLWFPGSRC DIQMTQSPSS VSASVGDRVT

ITCRASQGIY SWLAWYQQKP GKAPNLLIYT ASTLQSGVPS

RFSGSGSGTD FTLTISSLQP EDFATYYCQQ ANIFPLTFGG

GTKVEIKRTV AAPSVFIFPP SDEQLKSGTA SVVCLLNNFY

PREAKVQWKV DNALQSGNSQ ESVTEQDSKD STYSLSSTLT

LSKADYEKHK VYACEVTHQG LSSPVTKSFN RGEC*
```

(i) Signal: M at position 1 to C at position 20
(ii) Variable region: D at position 21 to R at position 128
(iii) Constant region: T at position 129 to C at position 234

The present invention is described below by Examples; however, the present invention is not limited to the following Examples.

Example 1

Construction of Expression Vector

Among anti-CD40 antibodies described in WO02/088186, a DNA fragment comprising a DNA (SEQ ID NO:3) of a heavy chain variable region of an antibody (hereinafter, referred to as "antibody 341-1-19") produced by a hybridoma KM341-1-19 (Accession No. BP-7759), and a DNA fragment comprising a DNA (SEQ ID NO:13) of a light chain variable region of the antibody each was constructed.

Similarly, among anti-CD40 antibodies described in WO03/040170, a DNA fragment comprising a DNA (SEQ ID NO:23) of a heavy chain variable region of 21.4.1 (hereinafter, referred to as "antibody 21.4.1"), and a DNA fragment comprising a DNA (SEQ ID NO:27) of a light chain variable region of the antibody each was constructed.

A DNA fragment was constructed so as to contain a DNA (hereinafter, referred to as "IgG2-AAS/DNA") with addition of a stop codon TGA to a DNA (SEQ ID NO:29) encoding IgG2 in which valine at position 234, glycine at position 237 and proline at position 331 were substituted with alanine, alanine and serine, respectively, (numbering is based on the EU index of Kabat et al). Then, the resulting DNA fragment was introduced into N5KG2-Val Lark vector (IDEC Pharmaceuticals, hereinafter referred to as "N5KG2 vector") having an IgG2 constant region. That is, a DNA fragment comprising IgG2-AAS/DNA was cleaved from the above DNA fragment using NheI and BamHI, and was substituted with a DNA encoding an IgG2 constant region of N5KG2 vector. The resulting expression vector was designated as N5KG2/V234A/G237A/P331S vector. Further, N5KG2-Val Lark vector comprising a DNA (hereinafter, referred to as IgG2-S/DNA) in which a stop codon TGA was added to a DNA (SEQ ID NO:31) encoding IgG2 in which proline at position 331 was substituted with serine (numbering is based on the EU index of Kabat et al.) was constructed according to the method described in WO05/063981. That is, a DNA fragment comprising IgG2-S/DNA was constructed, and a DNA fragment comprising IgG2-S/DNA was cleaved therefrom using NheI and BamHI, followed by substitution with a DNA encoding an IgG2 constant region of N5KG2 vector. The resulting expression vector was designated as an N5KG2/P331S vector.

These N5KG2/V234A/G237A/P331S vector and N5KG2/P331S vector were digested with BglII and BsiWI, respectively, and then the DNA fragment comprising a DNA of a light chain variable region of antibody 341-1-19 was inserted thereinto. Next, the obtained vectors were digested with SalI and NheI and then the DNA fragment comprising a DNA of a heavy chain variable region of antibody 341-1-19 was inserted thereinto. Finally, expression vectors which comprised a variable region of antibody 341-1-19, and a heavy chain constant region which was IgG2 in which valine at position 234, glycine at position 237 and proline at position 331 were substituted with alanine, alanine and serine, respectively, (numbering is based on the EU index of Kabat et al.) or was IgG2 in which proline at position 331 was substituted with serine (numbering is based on the EU index of Kabat et al) were completed (each of them was designated as N5KG2/V234A/G237A/P331S-341 vector and N5KG2/P331S-341 vector).

Furthermore, N5KG2_V234A_G237A_P331S and N5KG2_P331S vector were digested with BglII and BsiWI, respectively, and then the DNA fragment comprising a DNA encoding a light chain variable region of antibody 21.4.1 and DNA fragment comprising a DNA encoding a heavy chain variable region of the antibody 21.4.1 were inserted into the obtained vector similarly to thereby complete the expression vectors (they were designated as N5KG2N234A/G237A/P3315-21.4.1 vector and N5KG2/P331S-21.4.1 vector, respectively).

Example 2

Expression and Purification of Antibody

The expression vector constructed in Example 1 was purified using an EndoFree Plasmid Kit (Qiagen). This expression vector was introduced into suspended 293 cells (Invitrogen Life Technologies) using a FreeStyle™ 293 Expression System (Invitrogen Life Technologies) and transiently expressed thereby to obtain a culture supernatant containing each antibody. The culture supernatant (about 500 µg in terms of IgG) was filtered through a membrane filter (manufactured by Millipore) with a pore size of 0.22 µm and then charged into a HiTrap rProtein A FF (column volume: 1 mL) (Amersham Biosciences) which is an affinity column for antibody purification. After washing the column with PBS(−), the antibodies were eluted with 20 mM citrate buffer (pH 3.4) and recovered in a tube containing 200 mM phosphate buffer (pH 7.0). The antibodies obtained from the cells into which each of N5KG2N234A/G237A/P331S-341 vector, N5KG2/P331S-341 vector, N5KG2N234A/G237A/P331S-21.4.1 vector and N5KG2/P331S-21.4.1 vector was introduced were designated as IgG2-AAS(341) antibody, IgG2-S(341) antibody, IgG2-AAS(21.4.1) antibody and IgG2-S(21.4.1) antibody, respectively.

Example 3

Binding Activity of Antibody

In order to investigate whether each of IgG2-AAS(341) antibody, IgG2-S(341) antibody, IgG2-AAS(21.4.1) antibody, and IgG2-S(21.4.1) antibody obtained in Example 2 binds to human CD40, a binding activity of the antibody to Ramos cell (ATCC CRL-1596) which expresses human CD40 was measured.

The Ramos cell line was suspended in staining buffer (SB) of PBS containing 0.1% $NaN_3$, 2 mM EDTA, and 2% FCS at a density of $2 \times 10^{-6}$ cells/mL. The cell suspension (100 µL/well) was dispensed into a 96-well round-bottom plate (manufactured by Becton Dickinson). The purified antibody (50 µL) was added thereto, followed by incubation at ice temperature for 30 minutes. As negative control, an anti-human IgG2 antibody against 2,4-dinitrophenol was used and the purified antibodies (50 µL) were similarly added, followed by incubation at ice temperature for 15 minutes. After the cells were washed with SB, 50 µL of 250-fold diluted R-PE fluorescence-labeled anti-human antibodies (manufactured by Southern Biotechnology) was added thereto, followed by incubation at ice temperature for 15 minutes. The cells were washed twice with SB and suspended in 300 to 500 µL of FACS buffer. And the fluorescence intensity (MFI) of individual cells was measured by FACS (FACScalibur, manufactured by Becton Dickinson).

Figure 1B:
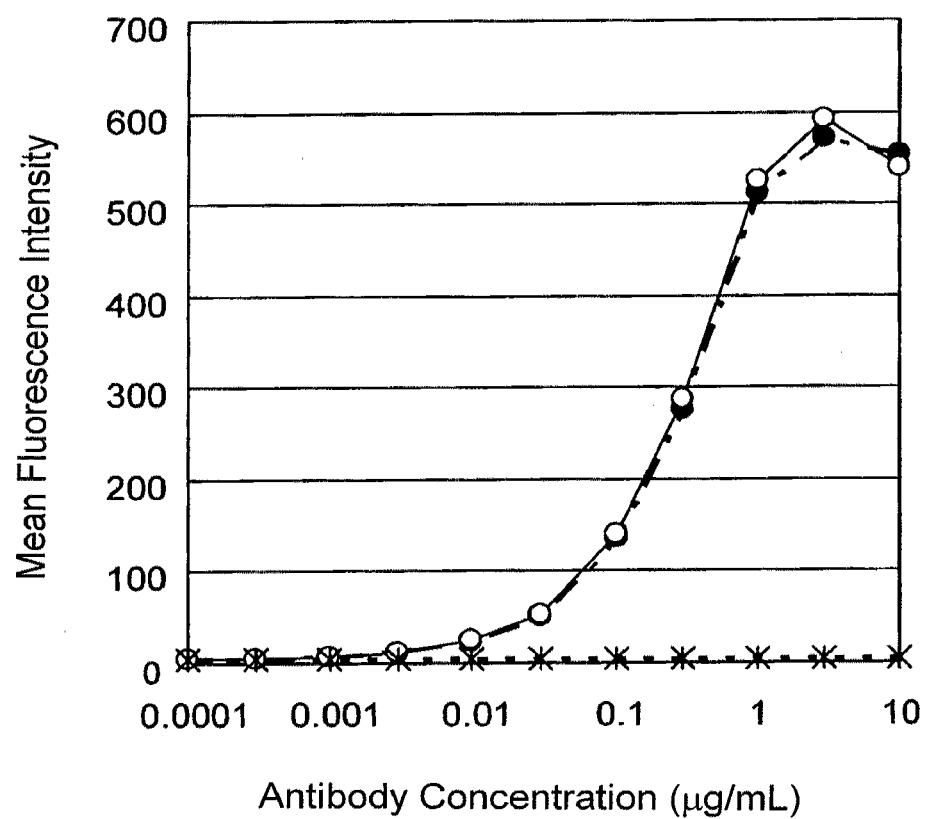
FIG. 1B shows a binding activity of IgG2-AAS(21.4.1) antibody. The abscissa represents the antibody concentration (μg/ml) and the ordinate represents the mean fluorescence intensity. The mean fluorescence intensity of IgG2-AAS (21.4.1) antibody is represented by the mark ● and the dashed line, the mean fluorescence intensity of IgG2-S(21.4.1) antibody is represented by the mark ○ and the solid line and the mean fluorescence intensity of the negative control antibody is represented by the mark * and the dotted line.

As a result, it was found that all of the antibodies bind to human CD40 (FIGS. 1A and 1B).

Example 4

Agonist Activity of Antibody

Both antibody KM341-1-19 and antibody 21.4.1 are known as an agonistic antibody. Therefore, the effect on an agonist activity due to the difference of a heavy chain constant region was examined. It was found that the expression of CD95 was elevated by adding CD40 ligand to Ramos cells. Accordingly, by adding the antibody instead of CD40 ligand, an agonist activity of the antibodies was evaluated using CD95 expression by the antibodies as an indicator.

First, $1.0 \times 10^{-6}$ cells/mL of Ramos cells were suspended in an RPMI1640 medium containing 10% fetal bovine serum, and seeded into a 96-well plate at 50 µL/well. The purified antibodies were added to a 96-well plate at 50 µL/well. After culturing overnight at 37° C. in the presence of 5% $CO_2$, the cells were recovered and analyzed by FACS in the same manner as in Example 3, using R-PE labeled anti-CD95 antibodies (manufactured by Pharmingen, N.J.).

Figure 2A:
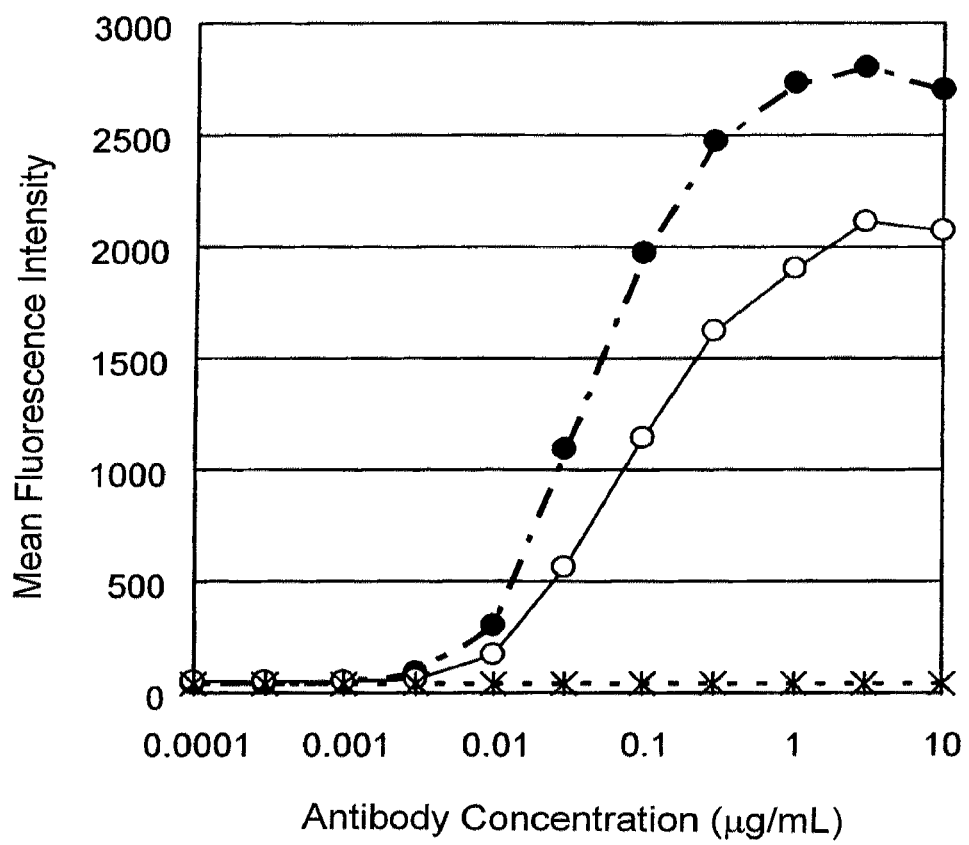
FIG. 2A shows an agonist activity of IgG2-AAS(341) antibody. The abscissa represents the antibody concentration (μg/ml) and the ordinate represents the mean fluorescence intensity. The mean fluorescence intensity of IgG2-AAS(341) antibody is represented by the mark ● and the dashed line, the mean fluorescence intensity of IgG2-S(341) antibody is represented by the mark ○ and the solid line and the mean fluorescence intensity of the negative control antibody is represented by the mark * and the dotted line.
Figure 2B:
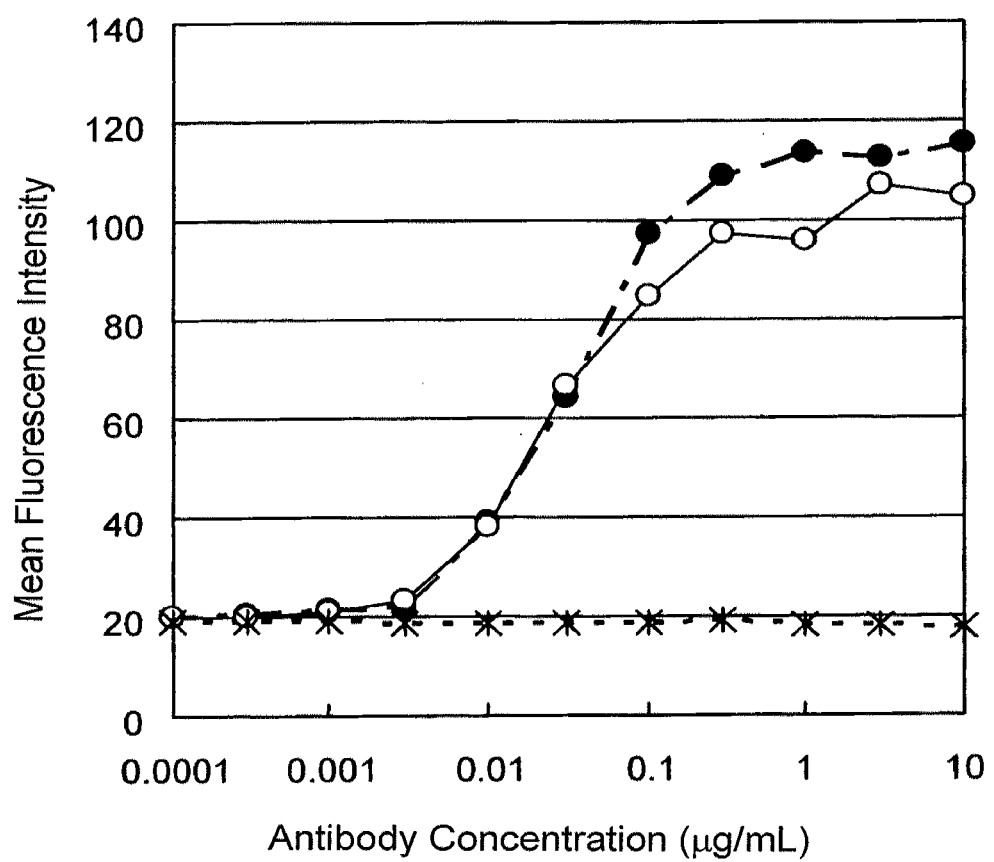
FIG. 2B shows an agonist activity of IgG2-AAS(21.4.1) antibody. The abscissa represents the antibody concentration (μg/ml) and the ordinate represents the mean fluorescence intensity. The mean fluorescence intensity of IgG2-AAS (21.4.1) antibody is represented by the mark ● and the dashed line, the mean fluorescence intensity of IgG2-S(21.4.1) antibody is represented by the mark ○ and the solid line and the mean fluorescence intensity of the negative control antibody is represented by the mark * and the dotted line.

As a result, both of IgG2-AAS(341) antibody and IgG2-AAS(21.4.1) antibody exhibited a remarkably higher agonist activity than reference antibodies, IgG2-S(341) antibody and IgG2-S(21.4.1) antibody (FIGS. 2A and 2B).

Example 5

Blood Residence Time of Antibodies

In order to examine blood residence time in the living body of the IgG2-AAS(341) antibody and IgG2-S(341) antibody prepared in Example 2, each of these antibodies was intravenously administrated to *Macaca fascicularis* and the drug concentration in serum was periodically measured.

The IgG2-AAS(341) antibody or IgG2-S(341) antibody (1 mg/kg) was intravenously administered. Blood samples were collected from a vein before the administration and after the administration, allowed to stands still at room temperature for 20 to 60 minutes and then centrifuged (room temperature, 3000 rpm, 15 minutes) to obtain sera which were preserved in an ultra-low temperature freezer during a period until measurement.

The drug concentration in serum was measured by the ELISA method. A human CD40-human Fc fusion protein (prepared by making reference to Example 1 of the specification of WO02/088186) was diluted with Tris buffered saline (SIGMA Cat # T6664) to give a concentration of 1 µg/ml, 100 µl of the obtained solution was added to each well of Immuno Plate (Greiner Cat #675097), and then incubated overnight at 4° C. The solution in wells was discarded and moisture therein was thoroughly removed. After adding 300 µl of Tris buffered saline containing 1% BSA (SIGMA Cat # A7638), incubation was carried out overnight at 4° C. A monkey serum was diluted 20 times with Tris buffered saline containing 1% BSA. The solution in wells was discarded, moisture therein was thoroughly removed, and 100 µl of the above-mentioned diluted serum was added to each well and incubated overnight at 4° C. Each well was washed 5 times with 300 µl of Tris buffered saline containing 0.1% Tween 20 and 0.5 mol/l of NaCl and the moisture was thoroughly removed. Anti-Human Kappa Light Chain Goat IgG-Biotin (Immuno-Biological Laboratories Co., Ltd., Cat #17249) was diluted to 20 ng/ml with Tris buffered saline containing 1% BSA, 100 µl of the obtained solution was added to each well and then allowed to stand still at room temperature for about 2 hours. One drop of each of the reagent A and reagent B attached to the Streptavidine-ABComplex/AP (DACO Cat # K0391) was added to 5 ml of 50 mmol/l Tris-HCl (pH 7.6) and then allowed to stand still in a cold and dark place for 30 minutes or more. This solution was diluted 51-fold with Sample diluent Buffer. Each well was washed 5 times with 300 µl of Tris buffered saline containing 0.1% Tween 20 and 0.5 mol/l of NaCl and the moisture was thoroughly removed. To each well, 100 µl of the above-mentioned Streptavidine-ABComplex/AP dilution liquid was added and then allowed to stand still at room temperature for about 1 hour. Each well was washed 5 times with 300 µl of Tris buffered saline containing 0.1% Tween 20 and 0.5 mol/l of NaCl and the moisture was thoroughly removed. The Lumi-phos 530 (Wako Pure Chemical Industries, Ltd., Cat #537-24662) was diluted two-fold with an aqueous solution (pH 10) containing 0.1% diethanolamine (Wako Pure Chemical Industries, Ltd., Cat #093-03115), 1 mmol/l $MgCl_2$ and 0.02% $NaN_3$, and 100 µl the obtained solution was added to each well. After mixing for about 15 seconds using a plate shaker, the solution was incubated at 30° C. for 20 minutes. By measuring chemiluminescence intensity, the antibody concentration was determined. In this connection, temperature of the plate reader was set to 30° C. during the measurement.

Figure 3:
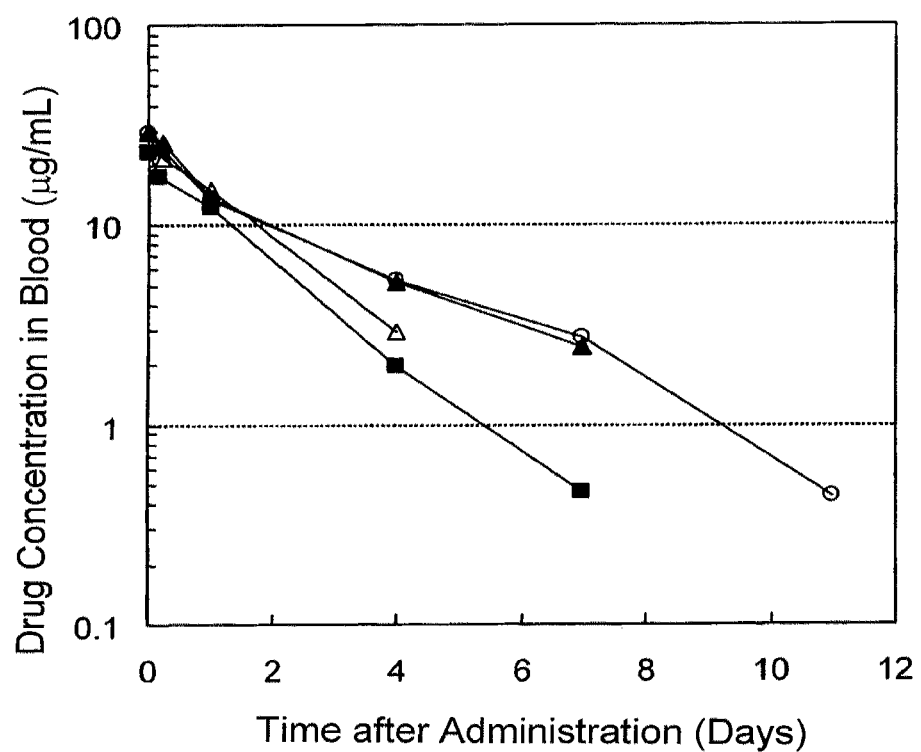
FIG. 3 shows the concentration of IgG2-AAS(341) antibody in blood. The abscissa represents the time after administration (days) and the ordinate represents the drug concentration in blood. The drug concentration in blood of IgG2-AAS(341) antibody is represented by the mark ● and the dashed line, the drug concentration in blood of IgG2-S(341) antibody is represented by the mark ○ and the solid line and the drug concentration in blood of the negative control antibody is represented by the mark * and the dotted line.

As a result, it was found that blood residence time of the IgG2-AAS(341) antibody was prolonged in comparison with the IgG2-S(341) antibody (FIG. 3).

Example 6

Blood Biochemical Parameters after Antibody Administration

In order to examine influences of the IgG2-AAS(341) antibody and IgG2-S(341) antibody prepared in Example 2 upon blood biochemical parameters in the individuals to which the antibody was administrated, each of these antibodies was intravenously administrated to a human CD40 BAC transgenic mouse and the antibody concentration in serum was periodically measured.

Firstly, human CD40 BAC transgenic mice were prepared. A cyclic BAC (bacterial artificial chromosome) clone comprising a human CD40 gene was purified by an anionic ion exchange column (MACHEREY-NAGEL; #740579), and the DNA solution was micro-injected into the fertilized egg pronucleus of C57BL/6J Jcl mouse (CLEA Japan Inc). Individuals were prepared by transplanting the DNA-injected fertilized egg to an oviduct of a female mouse in a state of pseudopregnancy. The tip of tail of each of the thus obtained individuals was digested overnight with a protease K/SDS and then a genomic DNA was prepared by phenol chloroform extraction and ethanol precipitation. A portion of the human CD40 gene region was amplified by PCR using the thus obtained genomic DNA as a template, and an individual having the human CD40 gene was selected. Using a heparin-coated capillary, 50 µl of the peripheral blood of this mouse was collected, mixed with 10 µl of PE-labeled anti-human CD40 antibody (Beckman Coulter; IM1936U) and incubated under ice temperature for 15 minutes. Thereafter, by carrying out hemolysis and immobilization using FACS Lysing Solution (BD), fluorescence was measured by FACS (FACScalibur, Becton Dickinson). As a result, it was found that the human CD40 was expressed in B cells, mononuclear cells and platelets which are generally known to express CD40.

Next, the IgG2-AAS(341) antibody or IgG2-S(341) antibody was diluted with phosphate buffer and administered to a human CD40 BAC transgenic mouse (four animals for each antibody) through a caudal vein (10 µg/head (a solution of 50 µg/ml was administered at a dose of 200 µl/head)). Blood samples were collected from veins at points of before the administration and 15 hour, 24 hours and 39 hours after the administration. Blood sera were obtained by carrying out centrifugation (room temperature, 9000 rpm, 2 minutes). The thus obtained sera were preserved in an ultra-low temperature freezer during the period until measurement. Each serum was diluted 50-fold with phosphate buffer, and AST and ALT were measured using TA-LN KAINOS (KAINOS Laboratories Inc., Cat # TDR5100) by the methods described in the attached documents.

Figure 4A:
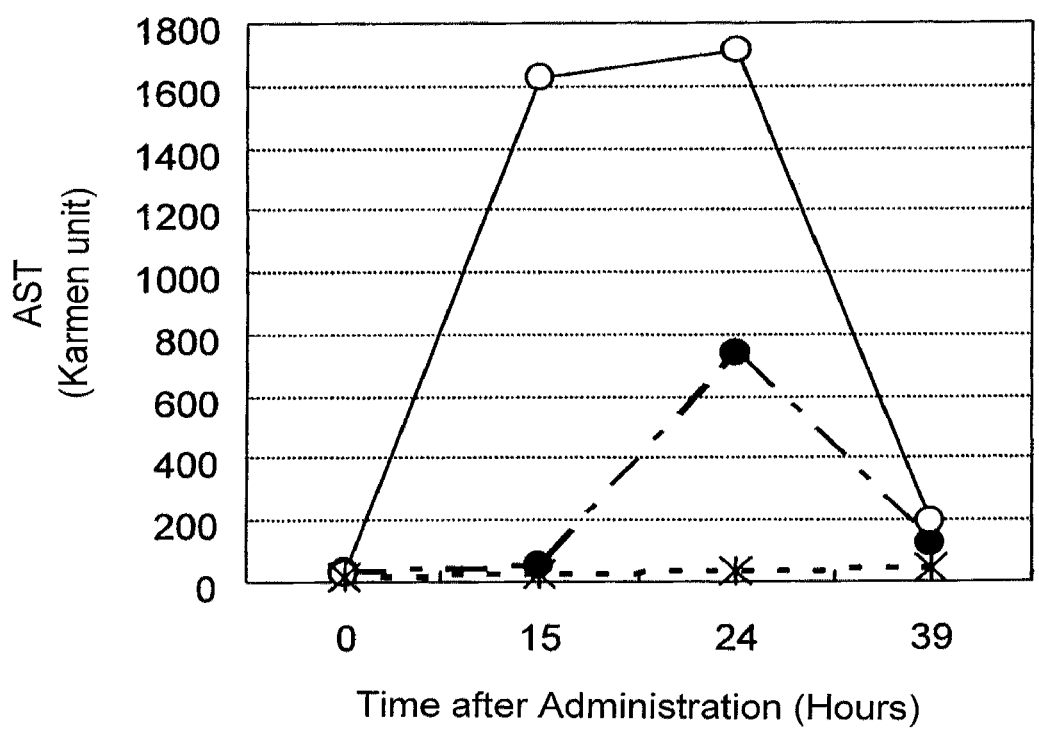
FIG. 4A shows the concentration of AST in blood. The abscissa represents the time after administration (hours) and the ordinate represents the activity value (Karmen unit). The AST at the time of administering IgG2-AAS(341) antibody is represented by the mark ● and the dashed line, the AST at the time of administering IgG2-S(341) antibody is represented by the mark ○ and the solid line and the AST at the time of administering PBS is represented by the mark * and the dotted line.
Figure 4B:
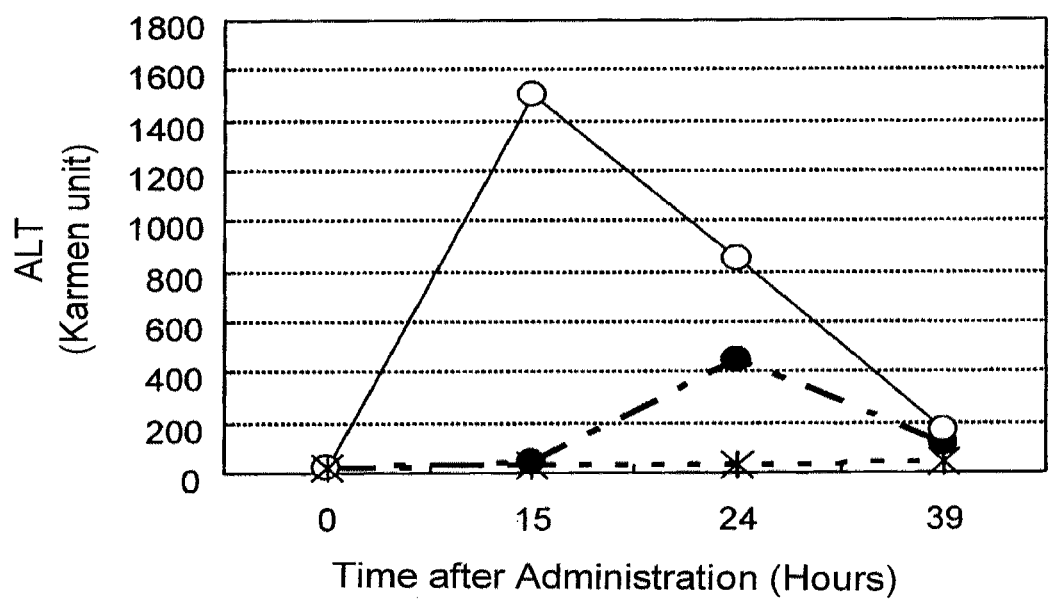
FIG. 4B shows the concentration of ALT in blood. The abscissa represents the time after administration (hours) and the ordinate represents the activity value (Karmen unit). The ALT at the time of administering IgG2-AAS(341) antibody is represented by the mark ● and the dashed line, the ALT at the time of administering IgG2-S(341) antibody is represented by the mark ○ and the solid line and the ALT at the time of administering PBS is represented by the mark * and the dotted line.

As a result, it was found that concentrations of AST and ALT are lowered by the IgG2-AAS(341) antibody in comparison with the IgG2-S(341) antibody (FIG. 4A and FIG. 4B).

Example 7

Growth Inhibitory Activity of Antibody for Tumor Cell

T24 cells (ATCC # HTB-4) were adjusted to give a density of $1.0 \times 10^5$ cells/ml using RPMI 1640 medium (GIBCO Cat #31800105) containing 10% fetal bovine serum (Invitrogen Cat #10099-141) and dispensed into a 96-well plate at 50 µl/well. The IgG2-AAS(341) antibody prepared in Example 2 was diluted, added to the 96-well plate at 50 µl/well and cultured at 37° C. for 3 days in the presence of 5% $CO_2$. Cell Titer-Glo Luminescent Cell Viability Assay (Promega Cat # G7570) was added thereto at 100 µl/well and allowed to stand still at room temperature for 10 minutes. The emission signal was measured using SpectraMax M5, and ratio of the number of survived cells at each concentration was calculated by regarding the number of survived cells when the antibody was not added as 100%. As a result, it was found that the IgG2-AAS(341) antibody inhibited growth of the T24 cells in a concentration dependent manner.

The partial DNA sequences and amino acid sequences of the antibody of the present invention are described below.

```
DNA sequence of the heavy chain of IgG2-AAS(341)
antibody
                                    (SEQ ID NO: 1)
ATGTCTGTCT CCTTCCTCAT CTTCCTGCCC GTGCTGGGCC

TCCCATGGGG TGTCCTGTCA CAGGTCCAAC TGCAGCAGTC

AGGTCCAGGA CTGGTGAAGC CCTCGCAGAC CCTCTCACTC
```

```
ACCTGTGCCA TCTCCGGGGA CAGTGTCTCT AGCAACAGTG
CTACTTGGAA CTGGATCAGG CAGTCCCCAT CGAGAGACCT
TGAGTGGCTG GGAAGGACAT ACTACAGGTC CAAGTGGTAT
CGTGATTATG TAGGATCTGT GAAAAGTCGA ATAATCATCA
ACCCAGACAC ATCCAACAAC CAGTTCTCCC TGCAGCTGAA
CTCTGTGACT CCCGAGGACA CGGCTATATA TTACTGTACA
AGAGCACAGT GGCTGGGAGG GGATTACCCC TACTACTACA
GTATGGACGT CTGGGGCCAA GGGACCACGG TCACCGTCTC
CTCAGCTAGC ACCAAGGGCC CATCGGTCTT CCCCCTGGCG
CCCTGCTCCA GGAGCACCTC CGAGAGCACA GCGGCCCTGG
GCTGCCTGGT CAAGGACTAC TTCCCCGAAC CGGTGACGGT
GTCGTGGAAC TCAGGCGCTC TGACCAGCGG CGTGCACACC
TTCCCAGCTG TCCTACAGTC CTCAGGACTC TACTCCCTCA
GCAGCGTGGT GACCGTGCCC TCCAGCAACT TCGGCACCCA
GACCTACACC TGCAACGTAG ATCACAAGCC CAGCAACACC
AAGGTGGACA AGACAGTTGA GCGCAAATGT TGTGTCGAGT
GCCCACCGTG CCCAGCACCA CCTGCAGCAG CACCGTCAGT
CTTCCTCTTC CCCCCAAAAC CCAAGGACAC CCTCATGATC
TCCCGGACCC CTGAGGTCAC GTGCGTGGTG GTGGACGTGA
GCCACGAAGA CCCCGAGGTC CAGTTCAACT GGTACGTGGA
CGGCGTGGAG GTGCATAATG CCAAGACAAA GCCACGGGAG
GAGCAGTTCA ACAGCACGTT CCGTGTGGTC AGCGTCCTCA
CCGTTGTGCA CCAGGACTGG CTGAACGGCA AGGAGTACAA
GTGCAAGGTC TCCAACAAAG CCTCCCAGC CTCCATCGAG
AAAACCATCT CCAAAACCAA AGGGCAGCCC CGAGAACCAC
AGGTGTACAC CCTGCCCCCA TCCCGGGAGG AGATGACCAA
GAACCAGGTC AGCCTGACCT GCCTGGTCAA AGGCTTCTAC
CCCAGCGACA TCGCCGTGGA GTGGGAGAGC AATGGGCAGC
CGGAGAACAA CTACAAGACC ACACCTCCCA TGCTGGACTC
CGACGGCTCC TTCTTCCTCT ACAGCAAGCT CACCGTGGAC
AAGAGCAGGT GGCAGCAGGG GAACGTCTTC TCATGCTCCG
TGATGCATGA GGCTCTGCAC AACCACTACA CGCAGAAGAG
CCTCTCCCTG TCTCCGGGTA AA
Amino Acid sequence of the heavy chain of
IgG2-AAS(341) antibody
                                    (SEQ ID NO: 2)
MSVSFLIFLP VLGLPWGVLS QVQLQQSGPG LVKPSQTLSL
TCAISGDSVS SNSATWNWIR QSPSRDLEWL GRTYYRSKWY
RDYVGSVKSR IIINPDTSNN QFSLQLNSVT PEDTAIYYCT
RAQWLGGDYP YYYSMDVWGQ GTTVTVSSAS TKGPSVFPLA
PCSRSTSEST AALGCLVKDY FPEPVTVSWN SGALTSGVHT
FPAVLQSSGL YSLSSVVTVP SSNFGTQTYT CNVDHKPSNT
KVDKTVERKC CVECPPCPAP PAAAPSVFLF PPKPKDTLMI
SRTPEVTCVV VDVSHEDPEV QFNWYVDGVE VHNAKTKPRE
EQFNSTFRVV SVLTVVHQDW LNGKEYKCKV SNKGLPASIE
KTISKTKGQP REPQVYTLPP SREEMTKNQV SLTCLVKGFY
PSDIAVEWES NGQPENNYKT TPPMLDSDGS FFLYSKLTVD
KSRWQQGNVF SCSVMHEALH NHYTQKSLSL SPGK DNA sequence of the heavy chain variable region
of IgG2-AAS(341) antibody
                                    (SEQ ID NO: 3)
CAGGTCCAAC TGCAGCAGTC AGGTCCAGGA CTGGTGAAGC
CCTCGCAGAC CCTCTCACTC ACCTGTGCCA TCTCCGGGGA
CAGTGTCTCT AGCAACAGTG CTACTTGGAA CTGGATCAGG
CAGTCCCCAT CGAGAGACCT TGAGTGGCTG GGAAGGACAT
ACTACAGGTC CAAGTGGTAT CGTGATTATG TAGGATCTGT
GAAAAGTCGA ATAATCATCA ACCCAGACAC ATCCAACAAC
CAGTTCTCCC TGCAGCTGAA CTCTGTGACT CCCGAGGACA
CGGCTATATA TTACTGTACA AGAGCACAGT GGCTGGGAGG
GGATTACCCC TACTACTACA GTATGGACGT CTGGGGCCAA
GGGACCACGG TCACCGTCTC CTCA Amino acid sequence of the heavy chain variable
region of IgG2-AAS(341) antibody
                                    (SEQ ID NO: 4)
QVQLQQSGPG LVKPSQTLSL TCAISGDSVS SNSATWNWIR
QSPSRDLEWL GRTYYRSKWY RDYVGSVKSR IIINPDTSNN
QFSLQLNSVT PEDTAIYYCT RAQWLGGDYP YYYSMDVWGQ
GTTVTVSSR DNA sequence of CDR1 of the heavy chain variable
region of IgG2-AAS(341) antibody
                                    (SEQ ID NO: 5)
AGCAACAGTG CTACTTGGAA C Amino acid sequence of CDR1 of the heavy chain
variable region of IgG2-AAS(341) antibody
                                    (SEQ ID NO: 6)
SNSATWN DNA sequence of CDR2 of the heavy chain variable
region of IgG2-AAS(341) antibody
                                    (SEQ ID NO: 7)
AGGACAT ACTACAGGTC CAAGTGGTAT CGTGATTATG
TAGGATCTGT GAAAAGT Amino acid sequence of CDR2 of the heavy chain
variable region of IgG2-AAS(341) antibody
                                    (SEQ ID NO: 8)
RTYYRSKWY RDYVGSVKS DNA sequence of CDR3 of the heavy chain variable
region of IgG2-AAS(341) antibody
                                    (SEQ ID NO: 9)
GCACAGT GGCTGGGAGG GGATTACCCC TACTACTACA
GTATGGACGT C Amino acid sequence of CDR3 of the heavy chain
variable region of IgG2-AAS(341) antibody
                                    (SEQ ID NO: 10)
AQWLGGDYP YYYSMDV
```

DNA sequence of the light chain of IgG2-AAS(341) antibody
(SEQ ID NO: 11)
ATGGAAGCCC AGCTCAGCT TCTCTTCCTC CTGCTACTCT

GGCTCCCAGA TACCACCGGA GAAATTGTGT TGACACAGTC

TCCAGCCACC CTGTCTTTGT CTCCAGGGGA AAGAGCCACC

CTCTCCTGCA GGGCCAGTCA GAGTGTTAGC AGCTACTTAG

CCTGGTACCA ACAGAAACCT GGCCAGGCTC CCAGGCTCCT

CATCTATGAT GCATCCAACA GGGCCACTGG CATCCCAGCC

AGGTTCAGTG GCAGTGGGTC TGGGACAGAC TTCACTCTCA

CCATCAGCAG CCTAGAGCCT GAAGATTTTG CAGTTTATTA

CTGTCAGCAG CGTAGCAACA CTTTCGGCCC TGGGACCAAA

GTGGATATCA AACGTACGGT GGCTGCACCA TCTGTCTTCA

TCTTCCCGCC ATCTGATGAG CAGTTGAAAT CTGGAACTGC

CTCTGTTGTG TGCCTGCTGA ATAACTTCTA TCCCAGAGAG

GCCAAAGTAC AGTGGAAGGT GGATAACGCC CTCCAATCGG

GTAACTCCCA GGAGAGTGTC ACAGAGCAGG ACAGCAAGGA

CAGCACCTAC AGCCTCAGCA GCACCCTGAC GCTGAGCAAA

GCAGACTACG AGAAACACAA AGTCTACGCC TGCGAAGTCA

CCCATCAGGG CCTGAGCTCG CCCGTCACAA AGAGCTTCAA

CAGGGGAGAG TGT

Amino Acid sequence of the light chain of IgG2-AAS(341) antibody
(SEQ ID NO: 12)
MEAPAQLLFL LLLWLPDTTG EIVLTQSPAT LSLSPGERAT

LSCRASQSVS SYLAWYQQKP GQAPRLLIYD ASNRATGIPA

RFSGSGSGTD FTLTISSLEP EDFAVYYCQQ RSNTFGPGTK

VDIKRTVAAP SVFIFPPSDE QLKSGTASVV CLLNNFYPRE

AKVQWKVDNA LQSGNSQESV TEQDSKDSTY SLSSTLTLSK

ADYEKHKVYA CEVTHQGLSS PVTKSFNRGE C

DNA sequence of the light chain variable region of IgG2-AAS(341) antibody
(SEQ ID NO: 13)
GAAATTGTGT TGACACAGTC TCCAGCCACC CTGTCTTTGT

CTCCAGGGGA AAGAGCCACC CTCTCCTGCA GGGCCAGTCA

GAGTGTTAGC AGCTACTTAG CCTGGTACCA ACAGAAACCT

GGCCAGGCTC CCAGGCTCCT CATCTATGAT GCATCCAACA

GGGCCACTGG CATCCCAGCC AGGTTCAGTG GCAGTGGGTC

TGGGACAGAC TTCACTCTCA CCATCAGCAG CCTAGAGCCT

GAAGATTTTG CAGTTTATTA CTGTCAGCAG CGTAGCAACA

CTTTCGGCCC TGGGACCAAA GTGGATATCA AA

Amino acid sequence of the light chain variable region of IgG2-AAS(341) antibody
(SEQ ID NO: 14)
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ RSNTFGPGTK VDIK

DNA sequence of CDR1 of the light chain variable region of IgG2-AAS(341) antibody
(SEQ ID NO: 15)
A GGGCCAGTCA GAGTGTTAGC AGCTACTTAG CC Amino acid sequence of CDR1 of the light chain variable region of IgG2-AAS(341) antibody
(SEQ ID NO: 16)
RASQSVS SYLA DNA sequence of CDR2 of the light chain variable region of IgG2-AAS(341) antibody
(SEQ ID NO: 17)
GAT GCATCCAACA GGGCCACT Amino acid sequence of CDR2 of the light chain variable region of IgG2-AAS(341) antibody
(SEQ ID NO: 18)
D ASNRAT DNA sequence of CDR3 of the light chain variable region of IgG2-AAS(341) antibody
(SEQ ID NO: 19)
CAGCAG CGTAGCAACA CT Amino acid sequence of CDR3 of the light chain variable region of IgG2-AAS(341) antibody
(SEQ ID NO: 20)
QQ RSNT DNA sequence of the heavy chain of IgG2-AAS (21.4.1) antibody
(SEQ ID NO: 21)
ATGGACTGGA CCTGGAGGAT CCTCTTCTTG GTGGCAGCAG

CCACAGGAGC CCACTCCCAG GTGCAGCTGG TGCAGTCTGG

GGCTGAGGTG AAGAAGCCTG GGGCCTCAGT GAAGGTCTCC

TGCAAGGCTT CTGGATACAC CTTCACCGGC TACTATATGC

ACTGGGTGCG ACAGGCCCCT GGACAAGGGC TTGAgtGGAT

GGGATGGATC AACCCTGACA GTGGTGGCAC AAACTATGCA

CAGAAGTTTC AGGGCAGGGT CACCATGACC AGGGACACGT

CCATCAGCAC AGCCTACATG GAGCTGAACA GGCTGAGATC

TGACGACACG GCCGTGTATT ACTGTGCGAG AGATCAGCCC

CTAGGATATT GTACTAATGG TGTATGCTCC TACTTTGACT

ACTGGGGCCA GGGAACCCTG GTCACCGTCT CCTCAGCTAG

CACCAAGGGC CCATCGGTCT TCCCCCTGGC GCCCTGCTCC

AGGAGCACCT CCGAGAGCAC AGCGGCCCTG GGCTGCCTGG

TCAAGGACTA CTTCCCCGAA CCGGTGACGG TGTCGTGGAA

CTCAGGCGCT CTGACCAGCG GCGTGCACAC CTTCCCAGCT

GTCCTACAGT CCTCAGGACT CTACTCCCTC AGCAGCGTGG

TGACCGTGCC CTCCAGCAAC TTCGGCACCC AGACCTACAC

CTGCAACGTA GATCACAAGC CCAGCAACAC CAAGGTGGAC

AAGACAGTTG AGCGCAAATG TTGTGTCGAG TGCCCACCGT

GCCCAGCACC ACCTGCAGCA GCACCGTCAG TCTTCCTCTT

CCCCCCAAAA CCCAAGGACA CCCTCATGAT CTCCCGGACC

CCTGAGGTCA CGTGCGTGGT GGTGGACGTG AGCCACGAAG

ACCCCGAGGT CCAGTTCAAC TGGTACGTGG ACGGCGTGGA

GGTGCATAAT GCCAAGACAA AGCCACGGGA GGAGCAGTTC

-continued

AACAGCACGT TCCGTGTGGT CAGCGTCCTC ACCGTTGTGC

ACCAGGACTG GCTGAACGGC AAGGAGTACA AGTGCAAGGT

CTCCAACAAA GGCCTCCCAG CCTCCATCGA GAAAACCATC

TCCAAAACCA AAGGGCAGCC CCGAGAACCA CAGGTGTACA

CCCTGCCCCC ATCCCGGGAG GAGATGACCA AGAACCAGGT

CAGCCTGACC TGCCTGGTCA AAGGCTTCTA CCCCAGCGAC

ATCGCCGTGG AGTGGGAGAG CAATGGGCAG CCGGAGAACA

ACTACAAGAC CACACCTCCC ATGCTGGACT CCGACGGCTC

CTTCTTCCTC TACAGCAAGC TCACCGTGGA CAAGAGCAGG

TGGCAGCAGG GGAACGTCTT CTCATGCTCC GTGATGCATG

AGGCTCTGCA CAACCACTAC ACGCAGAAGA GCCTCTCCCT

GTCTCCGGGT AAA

Amino Acid sequence of the heavy chain of
IgG2-AAS(21.4.1) antibody
(SEQ ID NO: 22)
MDWTWRILFL VAAATGAHSQ VQLVQSGAEV KKPGASVKVS

CKASGYTFTG YYMHWVRQAP GQGLEWMGWI NPDSGGTNYA

QKFQGRVTMT RDTSISTAYM ELNRLRSDDT AVYYCARDQP

LGYCTNGVCS YFDYWGQGTL VTVSSASTKG PSVFPLAPCS

RSTSESTAAL GCLVKDYFPE PVTVSWNSGA LTSGVHTFPA

VLQSSGLYSL SSVVTVPSSN FGTQTYTCNV DHKPSNTKVD

KTVERKCCVE CPPCPAPPAA APSVFLFPPK PKDTLMISRT

PEVTCVVVDV SHEDPEVQFN WYVDGVEVHN AKTKPREEQF

NSTFRVVSVL TVVHQDWLNG KEYKCKVSNK GLPASIEKTI

SKTKGQPREP QVYTLPPSRE EMTKNQVSLT CLVKGFYPSD

IAVEWESNGQ PENNYKTTPP MLDSDGSFFL YSKLTVDKSR

WQQGNVFSCS VMHEALHNHY TQKSLSLSPG K

DNA sequence of the heavy chain variable region
of IgG2-AAS(21.4.1) antibody
(SEQ ID NO: 23)
CAG

GTGCAGCTGG TGCAGTCTGG GGCTGAGGTG AAGAAGCCTG

GGGCCTCAGT GAAGGTCTCC TGCAAGGCTT CTGGATACAC

CTTCACCGGC TACTATATGC ACTGGGTGCG ACAGGCCCCT

GGACAAGGGC TTGAgtGGAT GGGATGGATC AACCCTGACA

GTGGTGGCAC AAACTATGCA CAGAAGTTTC AGGGCAGGGT

CACCATGACC AGGGACACGT CCATCAGCAC AGCCTACATG

GAGCTGAACA GGCTGAGATC TGACGACACG GCCGTGTATT

ACTGTGCGAG AGATCAGCCC CTAGGATATT GTACTAATGG

TGTATGCTCC TACTTTGACT ACTGGGGCCA GGGAACCCTG

GTCACCGTCT CCTCA

Amino acid sequence of the light chain variable
region of IgG2-AAS(21.4.1) antibody
(SEQ ID NO: 24)
Q VQLVQSGAEV KKPGASVKVS CKASGYTFTG YYMHWVRQAP

GQGLEWMGWI NPDSGGTNYA QKFQGRVTMT RDTSISTAYM

ELNRLRSDDT AVYYCARDQP LGYCTNGVCS YFDYWGQGTL

VTVSS

DNA sequence of the light chain of IgG2-AAS
(21.4.1) antibody
(SEQ ID NO: 25)
ATGAGGCTCC CTGCTCAGCT CCTGGGGCTC CTGCTGCTCT

GGTTCCCAGG TTCCAGATGC GACATCCAGA TGACCCAGTC

TCCATCTTCC GTGTCTGCAT CTGTAGGAGA CAGAGTCACC

ATCACTTGTC GGGCGAGTCA GGGTATTTAC AGCTGGTTAG

CCTGGTATCA GCAGAAACCA GGGAAAGCCC CTAACCTCCT

GATCTATACT GCATCCACTT TACAAAGTGG GGTCCCATCA

AGGTTCAGCG GCAGTGGATC TGGGACAGAT TTCACTCTCA

CCATCAGCAG CCTGCAACCT GAAGATTTTG CAACTTACTA

TTGTCAACAG GCTAACATTT TCCCGCTCAC TTTCGGCGGA

GGGACCAAGG TGGAGATCAA ACGTACGGTG GCTGCACCAT

CTGTCTTCAT CTTCCCGCCA TCTGATGAGC AGTTGAAATC

TGGAACTGCC TCTGTTGTGT GCCTGCTGAA TAACTTCTAT

CCCAGAGAGG CCAAAGTACA GTGGAAGGTG GATAACGCCC

TCCAATCGGG TAACTCCCAG GAGAGTGTCA CAGAGCAGGA

CAGCAAGGAC AGCACCTACA GCCTCAGCAG CACCCTGACG

CTGAGCAAAG CAGACTACGA GAAACACAAA GTCTACGCCT

GCGAAGTCAC CCATCAGGGC CTGAGCTCGC CCGTCACAAA

GAGCTTCAAC AGGGGAGAGT GT

Amino Acid sequence of the light chain of
IgG2-AAS(21.4.1) antibody
(SEQ ID NO: 26)
MRLPAQLLGL LLLWFPGSRC DIQMTQSPSS VSASVGDRVT

ITCRASQGIY SWLAWYQQKP GKAPNLLIYT ASTLQSGVPS

RFSGSGSGTD FTLTISSLQP EDFATYYCQQ ANIFPLTFGG

GTKVEIKRTV AAPSVFIFPP SDEQLKSGTA SVVCLLNNFY

PREAKVQWKV DNALQSGNSQ ESVTEQDSKD STYSLSSTLT

LSKADYEKHK VYACEVTHQG LSSPVTKSFN RGEC

DNA sequence of the light chain variable region
of IgG2-AAS(21.4.1) antibody
(SEQ ID NO: 27)
GACATCCAGA TGACCCAGTC TCCATCTTCC GTGTCTGCAT

CTGTAGGAGA CAGAGTCACC ATCACTTGTC GGGCGAGTCA

GGGTATTTAC AGCTGGTTAG CCTGGTATCA GCAGAAACCA

GGGAAAGCCC CTAACCTCCT GATCTATACT GCATCCACTT

TACAAAGTGG GGTCCCATCA AGGTTCAGCG GCAGTGGATC

TGGGACAGAT TCACTCTCA CCATCAGCAG CCTGCAACCT

GAAGATTTTG CAACTTACTA TTGTCAACAG GCTAACATTT

-continued
TCCCGCTCAC TTTCGGCGGA GGGACCAAGG TGGAGATCAA

ACGT

Amino acid sequence of the light chain variable
region of IgG2-AAS(21.4.1) antibody
(SEQ ID NO: 28)
DIQMTQSPSS VSASVGDRVT ITCRASQGIY SWLAWYQQKP

GKAPNLLIYT ASTLQSGVPS RFSGSGSGTD FTLTISSLQP

EDFATYYCQQ ANIFPLTFGG GTKVEIKR

DNA sequence of the heavy chain constant region
of IgG2-AAS(341) antibody
(SEQ ID NO: 29)
GCTAGC ACCAAGGGCC CATCGGTCTT CCCCCTGGCG CCCTGCTCCA

GGAGCACCTC CGAGAGCACA GCGGCCCTGG GCTGCCTGGT

CAAGGACTAC TTCCCCGAAC CGGTGACGGT GTCGTGGAAC

TCAGGCGCTC TGACCAGCGG CGTGCACACC TTCCCAGCTG

TCCTACAGTC CTCAGGACTC TACTCCCTCA GCAGCGTGGT

GACCGTGCCC TCCAGCAACT TCGGCACCCA GACCTACACC

TGCAACGTAG ATCACAAGCC CAGCAACACC AAGGTGGACA

AGACAGTTGA GCGCAAATGT TGTGTCGAGT GCCCACCGTG

CCCAGCACCA CCTGCAGCAG CACCGTCAGT CTTCCTCTTC

CCCCCAAAAC CCAAGGACAC CCTCATGATC TCCCGGACCC

CTGAGGTCAC GTGCGTGGTG GTGGACGTGA GCCACGAAGA

CCCCGAGGTC CAGTTCAACT GGTACGTGGA CGGCGTGGAG

GTGCATAATG CCAAGACAAA GCCACGGGAG GAGCAGTTCA

ACAGCACGTT CCGTGTGGTC AGCGTCCTCA CCGTTGTGCA

CCAGGACTGG CTGAACGGCA AGGAGTACAA GTGCAAGGTC

TCCAACAAAG GCCTCCCAGC CTCCATCGAG AAAACCATCT

CCAAAACCAA AGGGCAGCCC CGAGAACCAC AGGTGTACAC

CCTGCCCCCA TCCCGGGAGG AGATGACCAA GAACCAGGTC

AGCCTGACCT GCCTGGTCAA AGGCTTCTAC CCCAGCGACA

TCGCCGTGGA GTGGGAGAGC AATGGGCAGC CGGAGAACAA

CTACAAGACC ACACCTCCCA TGCTGGACTC CGACGGCTCC

TTCTTCCTCT ACAGCAAGCT CACCGTGGAC AAGAGCAGGT

GGCAGCAGGG GAACGTCTTC TCATGCTCCG TGATGCATGA

GGCTCTGCAC AACCACTACA CGCAGAAGAG CCTCTCCCTG

TCTCCGGGTA AA

Amino acid sequence of the heavy chain constant
region of IgG2-AAS(341) antibody
(SEQ ID NO: 30)
ASTKG PSVFPLAPCS RSTSESTAAL GCLVKDYFPE PVTVSWNSGA

LTSGVHTFPA VLQSSGLYSL SSVVTVPSSN FGTQTYTCNV

DHKPSNTKVD KTVERKCCVE CPPCPAPPAA APSVFLFPPK

PKDTLMISRT PEVTCVVVDV SHEDPEVQFN WYVDGVEVHN

AKTKPREEQF NSTFRVVSVL TVVHQDWLNG KEYKCKVSNK

GLPASIEKTI SKTKGQPREP QVYTLPPSRE EMTKNQVSLT

CLVKGFYPSD IAVEWESNGQ PENNYKTTPP MLDSDGSFFL

YSKLTVDKSR WQQGNVFSCS VMHEALHNHY TQKSLSLSPG K

DNA sequence of the heavy chain constant region
of IgG2-S(341) antibody
(SEQ ID NO: 31)
GCTAGCACCAAGGGCCCATCGGTCTTCCCCCTGGCG

CCCTGCTCCAGGAGCACCTCCGAGAGCACAGCGGCCCTGGGCTGCCTGG

TCAAGGACTACTTCCCCGAACCGGTGACGGTGTCGTGGAACTCAGGCGC

TCTGACCAGCGGCGTGCACACCTTCCCAGCTGTCCTACAGTCCTCAGGA

CTCTACTCCCTCAGCAGCGTGGTGACCGTGCCCTCCAGCAACTTCGGCA

CCCAGACCTACACCTGCAACGTAGATCACAAGCCCAGCAACACCAAGGT

GGACAAGACAGTTGAGCGCAAATGTTGTGTCGAGTGCCCACCGTGCCCA

GCACCACCTGTGGCAGGACCGTCAGTCTTCCTCTTCCCCCCAAAACCCA

AGGACACCCTCATGATCTCCCGGACCCCTGAGGTCACGTGCGTGGTGGT

GGACGTGAGCCACGAAGACCCCGAGGTCCAGTTCAACTGGTACGTGGAC

GGCGTGGAGGTGCATAATGCCAAGACAAAGCCACGGGAGGAGCAGTTCA

ACAGCACGTTCCGTGTGGTCAGCGTCCTCACCGTTGTGCACCAGGACTG

GCTGAACGGCAAGGAGTACAAGTGCAAGGTCTCCAACAAAGCCCTCCCA

GCCTCCATCGAGAAAACCATCTCCAAAACCAAAGGGCAGCCCCGAGAAC

CACAGGTGTACACCCTGCCCCCATCCCGGGAGGAGATGACCAAGAACCA

GGTCAGCCTGACCTGCCTGGTCAAAGGCTTCTACCCCAGCGACATCGCC

GTGGAGTGGGAGAGCAATGGGCAGCCGGAGAACAACTACAAGACCACAC

CTCCCATGCTGGACTCCGACGGCTCCTTCTTCCTCTACAGCAAGCTCAC

CGTGGACAAGAGCAGGTGGCAGCAGGGGAACGTCTTCTCATGCTCCGTG

ATGCATGAGGCTCTGCACAACCACTACACGCAGAAGAGCCTCTCCCTGT

CTCCGGGTAAA

Amino acid sequence of the heavy chain constant
region of IgG2-S(341) antibody
(SEQ ID NO: 32)
ASTKGPSVFPLAPCSRSTSESTAALGCLVKDY

FPEPVTVSWNSGALTSGVHTFPAVLQSSGLYSLSSVVTVPSSNFGTQTY

TCNVDHKPSNTKVDKTVERKCCVECPPCPAPPVAGPSVFLFPPKPKDTL

MISRTPEVTCVVVDVSHEDPEVQFNWYVDGVEVHNAKTKPREEQFNSTF

RVVSVLTVVHQDWLNGKEYKCKVSNKGLPASIEKTISKTKGQPREPQVY

TLPPSREEMTKNQVSLTCLVKGFYPSDIAVEWESNGQPENNYKTTPPML

DSDGSFFLYSKLTVDKSRWQQGNVFSCSVMHEALHNHYTQKSLSLSPGK

Amino acid sequence of IgG2 allotype 1
(SEQ ID NO: 33)
ASTKG PSVFPLAPCS RSTSESTAAL GCLVKDYFPE PVTVSWNSGA

LTSGVHTFPA VLQSSGLYSL SSVVTVPSSN FGTQTYTCNV

DHKPSNTKVD KTVERKCCVE CPPCPAPPVA GPSVFLFPPK

PKDTLMISRT PEVTCVVVDV SHEDPEVQFN WYVDGVEVHN

AKTKPREEQF NSTFRVVSVL TVVHQDWLNG KEYKCKVSNK

GLPAPIEKTI SKTKGQPREP QVYTLPPSRE EMTKNQVSLT

```
-continued
CLVKGFYPSD IAVEWESNGQ PENNYKTTPP MLDSDGSFFL

YSKLTVDKSR WQQGNVFSCS VMHEALHNHY TQKSLSLSPG K

Amino acid sequence of IgG2 allotype 2
                                        (SEQ ID NO: 34)
ASTKG PSVFPLAPCS RSTSESTAAL GCLVKDYFPE PVTVSWNSGA

LTSGVHTFPA VLQSSGLYSL SSVVTVTSSN FGTQTYTCNV

DHKPSNTKVD KTVERKCCVE CPPCPAPPVA GPSVFLFPPK

PKDTLMISRT PEVTCVVVDV SHEDPEVQFN WYVDGMEVHN

AKTKPREEQF NSTFRVVSVL TVVHQDWLNG KEYKCKVSNK

GLPAPIEKTI SKTKGQPREP QVYTLPPSRE EMTKNQVSLT

CLVKGFYPSD IAVEWESNGQ PENNYKTTPP MLDSDGSFFL

YSKLTVDKSR WQQGNVFSCS VMHEALHNHY TQKSLSLSPG K

Amino acid sequence of IgG2 allotype 3
                                        (SEQ ID NO: 35)
ASTKG PSVFPLAPCS RSTSESTAAL GCLVKDYFPE PVTVSWNSGA

LTSGVHTFPA VLQSSGLYSL SSVVTVPSSS LGTQTYTCNV

DHKPSNTKVD KTVERKCCVE CPPCPAPPVA GPSVFLFPPK

PKDTLMISRT PEVTCVVVDV SHEDPEVQFN WYVDGVEVHN

AKTKPREEQF NSTFRVVSVL TVVHQDWLNG KEYKCKVSNK

GLPAPIEKTI SKTKGQPREP QVYTLPPSRE EMTKNQVSLT

CLVKGFYPSD IAVEWESNGQ PENNYKTTPP MLDSDGSFFL

YSKLTVDKSR WQQGNVFSCS VMHEALHNHY TQKSLSLSPG K
```

While the invention has been described in detail and with reference to specific embodiments thereof, it will be apparent to one skill in the art that various changes and modifications can be made therein without departing from the spirit and scope thereof.

This application is based on U.S. provisional application filed on Apr. 20, 2009 (U.S. provisional application No. 61/170,738), the entire contents of which are incorporated hereinto by reference. All references cited herein are incorporated in their entirety.

INDUSTRIAL APPLICABILITY

The present invention can provide a monoclonal antibody which comprises a heavy chain constant region which is IgG2 wherein valine at position 234, glycine at position 237 and proline at position 331 are at least substituted with alanine, alanine and serine, respectively (numbering is based on the EU index of Kabat et al); has an agonist activity; and binds to human CD40; DNA encoding the monoclonal antibody; a vector comprising the DNA; a transformant obtainable by introducing the vector; a method for producing the monoclonal antibody comprising using the transformant; and a pharmaceutical composition and a therapeutic agent comprising the monoclonal antibody.

Free Text of Sequence Listing

SEQ ID NO:1—Description of Artificial Sequence: IgG2—DNA sequence of the heavy chain of IgG2-AAS(341) antibody SEQ ID NO:2—Description of Artificial Sequence: IgG2—Amino Acid sequence of the heavy chain of IgG2-AAS(341) antibody SEQ ID NO:3—Description of Artificial Sequence: IgG2—DNA sequence of the heavy chain variable region of IgG2-AAS(341) antibody SEQ ID NO:4—Description of Artificial Sequence: IgG2—Amino acid sequence of the heavy chain variable region of IgG2-AAS(341) antibody SEQ ID NO:5—Description of Artificial Sequence: IgG2—DNA sequence of CDR1 of the heavy chain variable region of IgG2-AAS(341) antibody SEQ ID NO:6—Description of Artificial Sequence: IgG2—Amino acid sequence of CDR1 of the heavy chain variable region of IgG2-AAS(341) antibody SEQ ID NO:7—Description of Artificial Sequence: IgG2—DNA sequence of CDR2 of the heavy chain variable region of IgG2-AAS(341) antibody SEQ ID NO:8—Description of Artificial Sequence: IgG2—Amino acid sequence of CDR2 of the heavy chain variable region of IgG2-AAS(341) antibody SEQ ID NO:9—Description of Artificial Sequence: IgG2—DNA sequence of CDR3 of the heavy chain variable region of IgG2-AAS(341) antibody SEQ ID NO:10—Description of Artificial Sequence: IgG2—Amino acid sequence of CDR3 of the heavy chain variable region of IgG2-AAS(341) antibody SEQ ID NO:11—Description of Artificial Sequence: IgG2—DNA sequence of the light chain of IgG2-AAS(341) antibody SEQ ID NO:12—Description of Artificial Sequence: IgG2—Amino Acid sequence of the light chain of IgG2-AAS(341) antibody SEQ ID NO:13—Description of Artificial Sequence: IgG2—DNA sequence of the light chain variable region of IgG2-AAS(341) antibody SEQ ID NO:14—Description of Artificial Sequence: IgG2—Amino acid sequence of the light chain variable region of IgG2-AAS(341) antibody SEQ ID NO:15—Description of Artificial Sequence: IgG2—DNA sequence of CDR1 of the light chain variable region of IgG2-AAS(341) antibody SEQ ID NO:16—Description of Artificial Sequence: IgG2—Amino acid sequence of CDR1 of the light chain variable region of IgG2-AAS(341) antibody SEQ ID NO:17—Description of Artificial Sequence: DNA sequence of CDR2 of the light chain variable region of IgG2-AAS(341) antibody SEQ ID NO:18—Description of Artificial Sequence: IgG2—Amino acid sequence of CDR2 of the light chain variable region of IgG2-AAS(341) antibody SEQ ID NO:19—Description of Artificial Sequence: IgG2—DNA sequence of CDR3 of the light chain variable region of IgG2-AAS(341) antibody SEQ ID NO:20—Description of Artificial Sequence: IgG2—Amino acid sequence of CDR3 of the light chain variable region of IgG2-AAS(341) antibody SEQ ID NO:21—Description of Artificial Sequence: IgG2—DNA sequence of the heavy chain of IgG2-AAS(21.4.1) antibody SEQ ID NO:22—Description of Artificial Sequence: Amino Acid sequence of the heavy chain of IgG2-AAS(21.4.1) antibody SEQ ID NO:23—Description of Artificial Sequence: IgG2—DNA sequence of the heavy chain variable region of IgG2-AAS(21.4.1) antibody SEQ ID NO:24—Description of Artificial Sequence: IgG2—Amino acid sequence of the light chain variable region of IgG2-AAS(21.4.1) antibody SEQ ID NO:25—Description of Artificial Sequence: IgG2—DNA sequence of the light chain of IgG2-AAS(21.4.1) antibody SEQ ID NO:26—Description of Artificial Sequence: IgG2—Amino Acid sequence of the light chain of IgG2-AAS(21.4.1) antibody SEQ ID NO:27—Description of Artificial Sequence: IgG2—DNA sequence of the light chain variable region of IgG2-AAS(21.4.1) antibody SEQ ID NO:28—Description of Artificial Sequence: IgG2—Amino acid sequence of the light chain variable region of IgG2-AAS(21.4.1) antibody SEQ ID NO:29—Description of Artificial Sequence: IgG2—DNA sequence of the heavy chain constant region of IgG2-AAS(341) antibody SEQ ID NO:30—Description of Artificial Sequence: IgG2—Amino acid sequence of the heavy chain constant region of IgG2-AAS(341) antibody SEQ ID NO:31—Description of Artificial Sequence: DNA sequence of the heavy chain constant region of IgG2-S(341) antibody SEQ ID NO:32—Description of Artificial Sequence: Amino acid sequence of the heavy chain constant region of IgG2-S(341) antibody

The invention claimed is:

1. A monoclonal antibody
    (a) which comprises a heavy chain constant region which is IgG2 wherein amino acid residues at positions 234, 237 and 331 of the IgG2 are substituted with alanine, alanine and serine, respectively; has an agonist activity; and binds to human CD40, wherein the amino acid numbering is based on the EU Index of Kabat et al.; or
    (b) which comprises the heavy chain constant region represented by SEQ ID NO:30, has an agonist activity, and binds to human CD40,
    wherein said monoclonal antibody has a heavy chain variable region comprising CDR1, CDR2 and CDR3 represented by SEQ ID NOs: 6, 8 and 10, respectively, and has a light chain variable region comprising CDR1, CDR2 and CDR3 represented by SEQ ID NOs: 16, 18 and 20, respectively.

2. The monoclonal antibody according to claim 1, which comprises the heavy chain variable region represented by SEQ ID NO:4, and the light chain variable region represented by SEQ ID NO:14.

3. The monoclonal antibody according to claim 1, which comprises a heavy chain variable region of an antibody produced by a hybridoma KM341-1-19 (FERM BP-7759) and a light chain variable region of an antibody produced by a hybridoma KM341-1-19 (FERM BP-7759).

4. The monoclonal antibody according to claim 1, which competes with an antibody produced by a hybridoma KM341-1-19 (FERM BP-7759).

5. The monoclonal antibody according to claim 1, which binds to a part or the entirety of an epitope on human CD40 to which an antibody produced by a hybridoma KM341-1-19 (FERM BP-7759) binds.

6. The monoclonal antibody according to claim 1, which comprises a polypeptide wherein a secretion signal is removed from the polypeptide represented by SEQ ID NO:2, and a polypeptide wherein a secretion signal is removed from the polypeptide represented by SEQ ID NO:12.

7. A pharmaceutical composition comprising the monoclonal antibody according to claim 1 as an active ingredient and a pharmaceutically acceptable carrier.

8. A method for inducing cell-mediated- and/or humoral-immunity against malignant tumors or infections, comprising administering the antibody of claim 1 to a patient with a malignant tumor or infection.

9. A pharmaceutical composition comprising the monoclonal antibody according to claim 6 as an active ingredient and a pharmaceutically acceptable carrier.

10. A method for inducing cellular apoptosis in malignant tumors expressing CD40, comprising administering the antibody of claim 1 to a patient with a malignant tumor expressing CD40.

* * * * *

SEQUENCE LISTING

```
<160> NUMBER OF SEQ ID NOS: 37

<210> SEQ ID NO 1
<211> LENGTH: 1422
<212> TYPE: DNA
<213> ORGANISM: Artificial Sequence
<220> FEATURE:
<223> OTHER INFORMATION: DNA sequence of heavy chain of IgG2-AAS(341)
      antibody

<400> SEQUENCE: 1
atgtctgtct ccttcctcat cttcctgccc gtgctgggcc tcccatgggg tgtcctgtca     60
caggtccaac tgcagcagtc aggtccagga ctggtgaagc cctcgcagac cctctcactc    120
acctgtgcca tctccgggga cagtgtctct agcaacagtg ctacttggaa ctggatcagg    180
cagtccccat cgagagacct tgagtggctg ggaaggacat actacaggtc caagtggtat    240
cgtgattatg taggatctgt gaaaagtcga ataatcatca cccagacac atccaacaac     300 cagttctccc tgcagctgaa ctctgtgact cccgaggaca cggctatata ttactgtaca    360
agagcacagt ggctgggagg ggattacccc tactactaca gtatggacgt ctggggccaa    420
gggaccacgg tcaccgtctc ctcagctagc accaagggcc catcggtctt ccccctggcg    480
ccctgctcca ggagcacctc cgagagcaca gcggccctgg gctgcctggt caaggactac    540
ttccccgaac cggtgacggt gtcgtggaac tcaggcgctc tgaccagcgg cgtgcacacc    600
ttcccagctg tcctacagtc ctcaggactc tactccctca gcagcgtggt gaccgtgccc    660
tccagcaact cggcaccca gacctacacc tgcaacgtag atcacaagcc cagcaacacc     720
aaggtggaca agacagttga gcgcaaatgt tgtgtcgagt gcccaccgtg cccagcacca    780
cctgcagcag caccgtcagt cttcctcttc cccccaaaac ccaaggacac cctcatgatc    840
tcccggaccc ctgaggtcac gtgcgtggtg gtggacgtga gccacgaaga ccccgaggtc    900
cagttcaact ggtacgtgga cggcgtggag gtgcataatg ccaagacaaa gccacgggag    960
gagcagttca acagcacgtt ccgtgtggtc agcgtcctca ccgttgtgca ccaggactgg   1020
ctgaacggca aggagtacaa gtgcaaggtc tccaacaaag gcctcccagc ctccatcgag   1080
aaaaccatct ccaaaaccaa agggcagccc cgagaaccac aggtgtacac cctgccccca   1140
tcccgggagg agatgaccaa gaaccaggtc agcctgacct gcctggtcaa aggcttctac   1200
cccagcgaca tcgccgtgga gtgggagagc aatgggcagc cggagaacaa ctacaagacc   1260
acacctccca tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aa                      1422
```

```
<210> SEQ ID NO 2
<211> LENGTH: 474
<212> TYPE: PRT
<213> ORGANISM: Artificial Sequence
<220> FEATURE:
<223> OTHER INFORMATION: Amino Acid sequence of heavy chain of
      IgG2-AAS(341) antibody

<400> SEQUENCE: 2

Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Ser Ala Thr Trp Asn Trp Ile Arg Gln Ser Pro Ser
    50                  55                  60

Arg Asp Leu Glu Trp Leu Gly Arg Thr Tyr Tyr Arg Ser Lys Trp Tyr
65                  70                  75                  80

Arg Asp Tyr Val Gly Ser Val Lys Ser Arg Ile Ile Asn Pro Asp
                85                  90                  95

Thr Ser Asn Asn Gln Phe Ser Leu Gln Leu Asn Ser Val Thr Pro Glu
            100                 105                 110

Asp Thr Ala Ile Tyr Tyr Cys Thr Arg Ala Gln Trp Leu Gly Gly Asp
        115                 120                 125

Tyr Pro Tyr Tyr Tyr Ser Met Asp Val Trp Gly Gln Gly Thr Thr Val
    130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Asn Phe
    210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Ala Ala Ala Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Phe Arg Val Val Ser Val Leu Thr Val Val
                325                 330                 335

His Gln Asp Trp Leu Asn Gly Lys Glu Tyr Lys Cys Lys Val Ser Asn
            340                 345                 350

Lys Gly Leu Pro Ala Ser Ile Glu Lys Thr Ile Ser Lys Thr Lys Gly
        355                 360                 365
```

```
Gln Pro Arg Glu Pro Gln Val Tyr Thr Leu Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 3
<211> LENGTH: 384
<212> TYPE: DNA
<213> ORGANISM: Artificial Sequence
<220> FEATURE:
<223> OTHER INFORMATION: DNA sequence of heavy chain variable region of
      IgG2-AAS(341) antibody

<400> SEQUENCE: 3
caggtccaac tgcagcagtc aggtccagga ctggtgaagc cctcgcagac cctctcactc      60
acctgtgcca tctccgggga cagtgtctct agcaacagtg ctacttggaa ctggatcagg     120
cagtccccat cgagagacct tgagtggctg gaaggacat actacaggtc caagtggtat      180
cgtgattatg taggatctgt gaaaagtcga ataatcatca acccagacac atccaacaac     240
cagttctccc tgcagctgaa ctctgtgact cccgaggaca cggctatata ttactgtaca     300
agagcacagt ggctgggagg ggattacccc tactactaca gtatggacgt ctggggccaa     360
gggaccacgg tcaccgtctc ctca                                            384

<210> SEQ ID NO 4
<211> LENGTH: 128
<212> TYPE: PRT
<213> ORGANISM: Artificial Sequence
<220> FEATURE:
<223> OTHER INFORMATION: Amino acid sequence of heavy chain variable
      region of IgG2-AAS(341) antibody

<400> SEQUENCE: 4

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Asp Leu Glu
        35                  40                  45

Trp Leu Gly Arg Thr Tyr Tyr Arg Ser Lys Trp Tyr Arg Asp Tyr Val
    50                  55                  60

Gly Ser Val Lys Ser Arg Ile Ile Ile Asn Pro Asp Thr Ser Asn Asn
65                  70                  75                  80

Gln Phe Ser Leu Gln Leu Asn Ser Val Thr Pro Glu Asp Thr Ala Ile
                85                  90                  95
```

```
Tyr Tyr Cys Thr Arg Ala Gln Trp Leu Gly Gly Asp Tyr Pro Tyr Tyr
            100                 105                 110

Tyr Ser Met Asp Val Trp Gly Gln Gly Thr Thr Val Thr Val Ser Ser
        115                 120                 125

<210> SEQ ID NO 5
<211> LENGTH: 21
<212> TYPE: DNA
<213> ORGANISM: Artificial Sequence
<220> FEATURE:
<223> OTHER INFORMATION: DNA sequence of CDR1 of heavy chain variable
      region of IgG2-AAS(341) antibody

<400> SEQUENCE: 5
agcaacagtg ctacttggaa c                                            21

<210> SEQ ID NO 6
<211> LENGTH: 7
<212> TYPE: PRT
<213> ORGANISM: Artificial Sequence
<220> FEATURE:
<223> OTHER INFORMATION: Amino acid sequence of CDR1 of heavy chain
      variable region of IgG2-AAS(341) antibody

<400> SEQUENCE: 6

Ser Asn Ser Ala Thr Trp Asn
1               5

<210> SEQ ID NO 7
<211> LENGTH: 54
<212> TYPE: DNA
<213> ORGANISM: Artificial Sequence
<220> FEATURE:
<223> OTHER INFORMATION: DNA sequence of CDR2 of heavy chain variable
      region of IgG2-AAS(341) antibody

<400> SEQUENCE: 7
aggacatact acaggtccaa gtggtatcgt gattatgtag gatctgtgaa aagt         54

<210> SEQ ID NO 8
<211> LENGTH: 18
<212> TYPE: PRT
<213> ORGANISM: Artificial Sequence
<220> FEATURE:
<223> OTHER INFORMATION: Amino acid sequence of CDR2 of heavy chain
      variable region of IgG2-AAS(341) antibody

<400> SEQUENCE: 8

Arg Thr Tyr Tyr Arg Ser Lys Trp Tyr Arg Asp Tyr Val Gly Ser Val
1               5                   10                  15

Lys Ser

<210> SEQ ID NO 9
<211> LENGTH: 48
<212> TYPE: DNA
<213> ORGANISM: Artificial Sequence
<220> FEATURE:
<223> OTHER INFORMATION: DNA sequence of CDR3 of heavy chain variable
      region of IgG2-AAS(341) antibody

<400> SEQUENCE: 9
gcacagtggc tgggagggga ttacccctac tactacagta tggacgtc                48
```

<210> SEQ ID NO 10
<211> LENGTH: 16
<212> TYPE: PRT
<213> ORGANISM: Artificial Sequence
<220> FEATURE:
<223> OTHER INFORMATION: Amino acid sequence of CDR3 of heavy chain variable region of IgG2-AAS(341) antibody

<400> SEQUENCE: 10

Ala Gln Trp Leu Gly Gly Asp Tyr Pro Tyr Tyr Tyr Ser Met Asp Val
1               5                   10                  15

<210> SEQ ID NO 11
<211> LENGTH: 693
<212> TYPE: DNA
<213> ORGANISM: Artificial Sequence
<220> FEATURE:
<223> OTHER INFORMATION: DNA sequence of light chain of IgG2-AAS(341) antibody

<400> SEQUENCE: 11

```
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
ggccaggctc ccaggctcct catctatgat gcatccaaca gggccactgg catcccagcc     240
aggttcagtg gcagtgggtc tgggacagac ttcactctca ccatcagcag cctagagcct     300
gaagattttg cagtttatta ctgtcagcag cgtagcaaca cttttcggcc ctgggaccaaa   360
gtggatatca aacgtacggt ggctgcacca tctgtcttca tcttcccgcc atctgatgag     420
cagttgaaat ctggaactgc ctctgttgtg tgcctgctga ataacttcta tcccagagag     480
gccaaagtac agtggaaggt ggataacgcc ctccaatcgg gtaactccca ggagagtgtc     540
acagagcagg acagcaagga cagcacctac agcctcagca gcaccctgac gctgagcaaa     600
gcagactacg agaaacacaa agtctacgcc tgcgaagtca cccatcaggg cctgagctcg     660
cccgtcacaa agagcttcaa caggggagag tgt                                  693
```

<210> SEQ ID NO 12
<211> LENGTH: 231
<212> TYPE: PRT
<213> ORGANISM: Artificial Sequence
<220> FEATURE:
<223> OTHER INFORMATION: Amino Acid sequence of light chain of IgG2-AAS(341) antibody

<400> SEQUENCE: 12

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Thr Phe Gly Pro Gly Thr Lys Val Asp Ile Lys Arg Thr Val Ala
            115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
            165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
            195                 200                 205

Tyr Ala Cys Glu Val Thr His Gln Gly Leu Ser Ser Pro Val Thr Lys
            210                 215                 220

Ser Phe Asn Arg Gly Glu Cys
225                 230

<210> SEQ ID NO 13
<211> LENGTH: 312
<212> TYPE: DNA
<213> ORGANISM: Artificial Sequence
<220> FEATURE:
<223> OTHER INFORMATION: DNA sequence of light chain variable region of
      IgG2-AAS(341) antibody

<400> SEQUENCE: 13
gaaattgtgt tgacacagtc tccagccacc ctgtctttgt ctccagggga aagagccacc        60
ctctcctgca gggccagtca gagtgttagc agctacttag cctggtacca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg cagtttatta ctgtcagcag cgtagcaaca cttttcggccc tgggaccaaa      300 gtggatatca aa                                                           312

<210> SEQ ID NO 14
<211> LENGTH: 104
<212> TYPE: PRT
<213> ORGANISM: Artificial Sequence
<220> FEATURE:
<223> OTHER INFORMATION: Amino acid sequence of light chain variable
      region of IgG2-AAS(341) antibody

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Thr Phe Gly
                85                  90                  95

Pro Gly Thr Lys Val Asp Ile Lys
            100

```
<210> SEQ ID NO 15
<211> LENGTH: 33
<212> TYPE: DNA
<213> ORGANISM: Artificial Sequence
<220> FEATURE:
<223> OTHER INFORMATION: DNA sequence of CDR1 of light chain variable
      region of IgG2-AAS(341) antibody

<400> SEQUENCE: 15
agggccagtc agagtgttag cagctactta gcc                                33

<210> SEQ ID NO 16
<211> LENGTH: 11
<212> TYPE: PRT
<213> ORGANISM: Artificial Sequence
<220> FEATURE:
<223> OTHER INFORMATION: Amino acid sequence of CDR1 of light chain
      variable region of IgG2-AAS(341) antibody

<400> SEQUENCE: 16

Arg Ala Ser Gln Ser Val Ser Ser Tyr Leu Ala
1               5                   10

<210> SEQ ID NO 17
<211> LENGTH: 21
<212> TYPE: DNA
<213> ORGANISM: Artificial Sequence
<220> FEATURE:
<223> OTHER INFORMATION: DNA sequence of CDR2 of light chain variable
      region of IgG2-AAS(341) antibody

<400> SEQUENCE: 17
gatgcatcca acagggccac t                                              21

<210> SEQ ID NO 18
<211> LENGTH: 7
<212> TYPE: PRT
<213> ORGANISM: Artificial Sequence
<220> FEATURE:
<223> OTHER INFORMATION: Amino acid sequence of CDR2 of light chain
      variable region of IgG2-AAS(341) antibody

<400> SEQUENCE: 18

Asp Ala Ser Asn Arg Ala Thr
1               5

<210> SEQ ID NO 19
<211> LENGTH: 18
<212> TYPE: DNA
<213> ORGANISM: Artificial Sequence
<220> FEATURE:
<223> OTHER INFORMATION: DNA sequence of CDR3 of light chain variable
      region of IgG2-AAS(341) antibody

<400> SEQUENCE: 19
cagcagcgta gcaacact                                                  18

<210> SEQ ID NO 20
<211> LENGTH: 6
<212> TYPE: PRT
<213> ORGANISM: Artificial Sequence
<220> FEATURE:
<223> OTHER INFORMATION: Amino acid sequence of CDR3 of light chain
      variable region of IgG2-AAS(341) antibody

<400> SEQUENCE: 20

Gln Gln Arg Ser Asn Thr
1               5
```

<210> SEQ ID NO 21
<211> LENGTH: 1413
<212> TYPE: DNA
<213> ORGANISM: Artificial Sequence
<220> FEATURE:
<223> OTHER INFORMATION: DNA sequence of heavy chain of IgG2-AAS(21.4.1)
      antibody

<400> SEQUENCE: 21

```
atggactgga cctggaggat cctcttcttg gtggcagcag ccacaggagc ccactcccag      60
gtgcagctgg tgcagtctgg ggctgaggtg aagaagcctg ggcctcagt gaaggtctcc     120
tgcaaggctt ctggatacac cttcaccggc tactatatgc actgggtgcg acaggcccct    180
ggacaagggc ttgagtggat gggatggatc aaccctgaca gtggtggcac aaactatgca    240
cagaagtttc agggcagggt caccatgacc agggacacgt ccatcagcac agcctacatg    300
gagctgaaca ggctgagatc tgacgacacg gccgtgtatt actgtgcgag agatcagccc    360
ctaggatatt gtactaatgg tgtatgctcc tactttgact actggggcca gggaaccctg    420
gtcaccgtct cctcagctag caccaagggc ccatcggtct tccccctggc gccctgctcc    480
aggagcacct ccgagagcac agcggccctg ggctgcctgg tcaaggacta cttccccgaa    540
ccggtgacgg tgtcgtggaa ctcaggcgct ctgaccagcg gcgtgcacac cttcccagct    600
gtcctacagt cctcaggact ctactccctc agcagcgtgg tgaccgtgcc ctccagcaac    660
ttcggcaccc agacctacac ctgcaacgta gatcacaagc ccagcaacac caaggtggac    720
aagacagttg agcgcaaatg ttgtgtcgag tgcccaccgt gcccagcacc acctgcagca    780
gcaccgtcag tcttcctctt ccccccaaaa cccaaggaca cctcatgat ctcccggacc    840
cctgaggtca cgtgcgtggt ggtggacgtg agccacgaag accccgaggt ccagttcaac    900
tggtacgtgg acggcgtgga ggtgcataat gccaagacaa agccacggga ggagcagttc    960
aacagcacgt tccgtgtggt cagcgtcctc accgttgtgc accaggactg gctgaacggc   1020
aaggagtaca agtgcaaggt ctccaacaaa ggcctcccag cctccatcga gaaaaccatc   1080
tccaaaacca agggcagcc cgagaaccca caggtgtaca ccctgccccc atcccgggag   1140
gagatgacca gaaccaggt cagcctgacc tgcctggtca aaggcttcta ccccagcgac   1200
atcgccgtgg agtgggagag caatgggcag ccggagaaca actacaagac cacacctccc   1260
atgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaaga gcctctccct gtctccgggt aaa                                1413
```

<210> SEQ ID NO 22
<211> LENGTH: 471
<212> TYPE: PRT
<213> ORGANISM: Artificial Sequence
<220> FEATURE:
<223> OTHER INFORMATION: Amino Acid sequence of heavy chain of
      IgG2-AAS(21.4.1) antibody

<400> SEQUENCE: 22

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

```
Thr Gly Tyr Tyr Met His Trp Val Arg Gln Ala Pro Gly Gln Gly Leu
 50                  55                  60
Glu Trp Met Gly Trp Ile Asn Pro Asp Ser Gly Gly Thr Asn Tyr Ala
 65                  70                  75                  80
Gln Lys Phe Gln Gly Arg Val Thr Met Thr Arg Asp Thr Ser Ile Ser
                 85                  90                  95
Thr Ala Tyr Met Glu Leu Asn Arg Leu Arg Ser Asp Asp Thr Ala Val
                100                 105                 110
Tyr Tyr Cys Ala Arg Asp Gln Pro Leu Gly Tyr Cys Thr Asn Gly Val
            115                 120                 125
Cys Ser Tyr Phe Asp Tyr Trp Gly Gln Gly Thr Leu Val Thr Val Ser
130                 135                 140
Ser Ala Ser Thr Lys Gly Pro Ser Val Phe Pro Leu Ala Pro Cys Ser
145                 150                 155                 160
Arg Ser Thr Ser Glu Ser Thr Ala Ala Leu Gly Cys Leu Val Lys Asp
                165                 170                 175
Tyr Phe Pro Glu Pro Val Thr Val Ser Trp Asn Ser Gly Ala Leu Thr
            180                 185                 190
Ser Gly Val His Thr Phe Pro Ala Val Leu Gln Ser Ser Gly Leu Tyr
        195                 200                 205
Ser Leu Ser Ser Val Val Thr Val Pro Ser Ser Asn Phe Gly Thr Gln
210                 215                 220
Thr Tyr Thr Cys Asn Val Asp His Lys Pro Ser Asn Thr Lys Val Asp
225                 230                 235                 240
Lys Thr Val Glu Arg Lys Cys Cys Val Glu Cys Pro Pro Cys Pro Ala
                245                 250                 255
Pro Pro Ala Ala Ala Pro Ser Val Phe Leu Phe Pro Pro Lys Pro Lys
            260                 265                 270
Asp Thr Leu Met Ile Ser Arg Thr Pro Glu Val Thr Cys Val Val Val
        275                 280                 285
Asp Val Ser His Glu Asp Pro Glu Val Gln Phe Asn Trp Tyr Val Asp
290                 295                 300
Gly Val Glu Val His Asn Ala Lys Thr Lys Pro Arg Glu Glu Gln Phe
305                 310                 315                 320
Asn Ser Thr Phe Arg Val Val Ser Val Leu Thr Val His Gln Asp
                325                 330                 335
Trp Leu Asn Gly Lys Glu Tyr Lys Cys Lys Val Ser Asn Lys Gly Leu
            340                 345                 350
Pro Ala Ser Ile Glu Lys Thr Ile Ser Lys Thr Lys Gly Gln Pro Arg
        355                 360                 365
Glu Pro Gln Val Tyr Thr Leu Pro Pro Ser Arg Glu Glu Met Thr Lys
370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Met Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
```

```
Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 23
<211> LENGTH: 378
<212> TYPE: DNA
<213> ORGANISM: Artificial Sequence
<220> FEATURE:
<223> OTHER INFORMATION: DNA sequence of heavy chain variable region of
      IgG2-AAS(21.4.1) antibody

<400> SEQUENCE: 23
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctg acagtggtgg cacaaactat      180
gcacagaagt tcagggcag ggtcaccatg accagggaca cgtccatcag cacagcctac      240
atggagctga acaggctgag atctgacgac acggccgtgt attactgtgc gagagatcag     300
cccctaggat attgtactaa tggtgtatgc tcctactttg actactgggg ccagggaacc     360
ctggtcaccg tctcctca                                                    378

<210> SEQ ID NO 24
<211> LENGTH: 126
<212> TYPE: PRT
<213> ORGANISM: Artificial Sequence
<220> FEATURE:
<223> OTHER INFORMATION: Amino acid sequence of heavy chain variable
      region of IgG2-AAS(21.4.1) antibody

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser
        115                 120                 125

<210> SEQ ID NO 25
<211> LENGTH: 702
<212> TYPE: DNA
<213> ORGANISM: Artificial Sequence
<220> FEATURE:
<223> OTHER INFORMATION: DNA sequence of light chain of IgG2-AAS(21.4.1)
      antibody
```

<400> SEQUENCE: 25

```
atgaggctcc ctgctcagct cctggggctc ctgctgctct ggttcccagg ttccagatgc    60
gacatccaga tgacccagtc tccatcttcc gtgtctgcat ctgtaggaga cagagtcacc   120
atcacttgtc gggcgagtca gggtatttac agctggttag cctggtatca gcagaaacca   180
gggaaagccc ctaacctcct gatctatact gcatccactt tacaaagtgg ggtcccatca   240
aggttcagcg gcagtggatc tgggacagat ttcactctca ccatcagcag cctgcaacct   300
gaagattttg caacttacta ttgtcaacag gctaacattt tcccgctcac tttcggcgga   360
gggaccaagg tggagatcaa acgtacggtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gt                      702
```

<210> SEQ ID NO 26
<211> LENGTH: 234
<212> TYPE: PRT
<213> ORGANISM: Artificial Sequence
<220> FEATURE:
<223> OTHER INFORMATION: Amino Acid sequence of light chain of IgG2-AAS(21.4.1) antibody

<400> SEQUENCE: 26

```
Met Arg Leu Pro Ala Gln Leu Leu Gly Leu Leu Leu Trp Phe Pro
1               5                   10                  15
Gly Ser Arg Cys Asp Ile Gln Met Thr Gln Ser Pro Ser Ser Val Ser
            20                  25                  30
Ala Ser Val Gly Asp Arg Val Thr Ile Thr Cys Arg Ala Ser Gln Gly
        35                  40                  45
Ile Tyr Ser Trp Leu Ala Trp Tyr Gln Gln Lys Pro Gly Lys Ala Pro
    50                  55                  60
Asn Leu Leu Ile Tyr Thr Ala Ser Thr Leu Gln Ser Gly Val Pro Ser
65                  70                  75                  80
Arg Phe Ser Gly Ser Gly Ser Gly Thr Asp Phe Thr Leu Thr Ile Ser
                85                  90                  95
Ser Leu Gln Pro Glu Asp Phe Ala Thr Tyr Tyr Cys Gln Gln Ala Asn
            100                 105                 110
Ile Phe Pro Leu Thr Phe Gly Gly Gly Thr Lys Val Glu Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
```

His Lys Val Tyr Ala Cys Glu Val Thr His Gln Gly Leu Ser Ser Pro
    210             215                 220

Val Thr Lys Ser Phe Asn Arg Gly Glu Cys
225             230

<210> SEQ ID NO 27
<211> LENGTH: 324
<212> TYPE: DNA
<213> ORGANISM: Artificial Sequence
<220> FEATURE:
<223> OTHER INFORMATION: DNA sequence of light chain variable region of
      IgG2-AAS(21.4.1) antibody

<400> SEQUENCE: 27
gacatccaga tgacccagtc tccatcttcc gtgtctgcat ctgtaggaga cagagtcacc        60
atcacttgtc gggcgagtca gggtatttac agctggttag cctggtatca gcagaaacca       120
gggaaagccc ctaacctcct gatctatact gcatccactt tacaaagtgg ggtcccatca       180
aggttcagcg gcagtggatc tgggacagat ttcactctca ccatcagcag cctgcaacct       240
gaagattttg caacttacta ttgtcaacag gctaacattt tcccgctcac tttcggcgga       300
gggaccaagg tggagatcaa acgt                                              324

<210> SEQ ID NO 28
<211> LENGTH: 108
<212> TYPE: PRT
<213> ORGANISM: Artificial Sequence
<220> FEATURE:
<223> OTHER INFORMATION: Amino acid sequence of light chain variable
      region of IgG2-AAS(21.4.1) antibody

<400> SEQUENCE: 28

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys Arg
            100                 105

<210> SEQ ID NO 29
<211> LENGTH: 978
<212> TYPE: DNA
<213> ORGANISM: Artificial Sequence
<220> FEATURE:
<223> OTHER INFORMATION: DNA sequence of heavy chain constant region of
      IgG2-AAS(341) antibody

<400> SEQUENCE: 29
gctagcacca agggcccatc ggtcttcccc ctggcgccct gctccaggag cacctccgag        60
agcacagcgg ccctgggctg cctggtcaag gactacttcc ccgaaccggt gacggtgtcg       120
tggaactcag gcgctctgac cagcggcgtg cacaccttcc cagctgtcct acagtcctca       180
ggactctact ccctcagcag cgtggtgacc gtgccctcca gcaacttcgg cacccagacc       240

```
tacacctgca acgtagatca caagcccagc aacaccaagg tggacaagac agttgagcgc    300
aaatgttgtg tcgagtgccc accgtgccca gcaccacctg cagcagcacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt tgtgcaccag gactggctga acggcaagga gtacaagtgc    600
aaggtctcca acaaaggcct cccagcctcc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacac ctcccatgct ggactccgac    840
ggctccttct tcctctacag caagctcacc gtggacaaga gcaggtggca gcaggggaac    900
gtcttctcat gctccgtgat gcatgaggct ctgcacaacc actacacgca gaagagcctc    960
tccctgtctc cgggtaaa                                                   978
```

<210> SEQ ID NO 30
<211> LENGTH: 326
<212> TYPE: PRT
<213> ORGANISM: Artificial Sequence
<220> FEATURE:
<223> OTHER INFORMATION: Amino acid sequence of heavy chain constant
      region of IgG2-AAS(341) antibody

<400> SEQUENCE: 30

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Ser Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 31
<211> LENGTH: 978
<212> TYPE: DNA
<213> ORGANISM: Artificial Sequence
<220> FEATURE:
<223> OTHER INFORMATION: DNA sequence of heavy chain constant region of
      IgG2-S(341) antibody

<400> SEQUENCE: 31
gctagcacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagcctcc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaa                                                   978

<210> SEQ ID NO 32
<211> LENGTH: 326
<212> TYPE: PRT
<213> ORGANISM: Artificial Sequence
<220> FEATURE:
<223> OTHER INFORMATION: Amino acid sequence of heavy chain constant
      region of IgG2-S(341) antibody
```

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 33
<211> LENGTH: 326
<212> TYPE: PRT
<213> ORGANISM: Homo sapiens

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 34
<211> LENGTH: 326
<212> TYPE: PRT
<213> ORGANISM: Homo sapiens

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80
```

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 35
<211> LENGTH: 326
<212> TYPE: PRT
<213> ORGANISM: Homo sapiens

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

```
Thr Leu Met Ile Ser Arg Thr Pro Glu Val Thr Cys Val Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 36
<211> LENGTH: 1616
<212> TYPE: DNA
<213> ORGANISM: Homo sapiens

<400> SEQUENCE: 36
gccaaggctg gggcagggga gtcagcagag gcctcgctcg ggcgcccagt ggtcctgccg      60
cctggtctca cctcgctatg gttcgtctgc ctctgcagtg cgtcctctgg ggctgcttgc     120
tgaccgctgt ccatccagaa ccacccactg catgcagaga aaacagtac  ctaataaaca     180 gtcagtgctg ttctttgtgc cagccaggac agaaactggt gagtgactgc acagagttca     240
ctgaaacgga atgccttcct tgcggtgaaa gcgaattcct agacacctgg aacagagaga     300
cacactgcca ccagcacaaa tactgcgacc ccaacctagg gcttcgggtc agcagaaggg     360
gcacctcaga aacagacacc atctgcacct gtgaagaagg ctggcactgt acgagtgagg     420
cctgtgagag ctgtgtcctg caccgctcat gctcgcccgg ctttgggtc  aagcagattg     480 ctacaggggt ttctgatacc atctgcgagc cctgcccagt cggcttcttc tccaatgtgt     540
catctgcttt cgaaaaatgt cacccttgga caagctgtga gaccaaagac tggttgtgc      600 aacaggcagg cacaaacaag actgatgttg tctgtggtcc ccaggatcgg ctgagagccc     660
tggtggtgat cccatcatc  ttcgggatcc tgtttgccat cctcttggtg ctggtcttta     720
tcaaaaaggt ggccaagaag ccaaccaata aggcccccca cccaagcag  gaaccccagg     780 agatcaattt tcccgacgat cttcctggct ccaacactgc tgctccagtg caggagactt     840 tacatgatg  ccaaccggtc acccaggagg atggcaaaga gagtcgcatc tcagtgcagg     900
agagacagtg aggctgcacc cacccaggag tgtggccacg tgggcaaaca ggcagttggc     960
```

```
cagagagcct ggtgctgctg ctgctgtggc gtgagggtga ggggctggca ctgactgggc    1020
atagctcccc gcttctgcct gcaccccctgc agtttgagac aggagacctg gcactggatg   1080
cagaaacagt tcaccttgaa gaacctctca cttcaccctg gagcccatcc agtctcccaa    1140
cttgtattaa agacagaggc agaagtttgg tggtggtggt gttggggtat ggtttagtaa    1200
tatccaccag accttccgat ccagcagttt ggtgcccaga gaggcatcat ggtggcttcc    1260
ctgcgcccag gaagccatat acacagatgc ccattgcagc attgtttgtg atagtgaaca   1320
actggaagct gcttaactgt ccatcagcag gagactggct aaataaaatt agaatatatt    1380
tatacaacag aatctcaaaa acactgttga gtaaggaaaa aaaggcatgc tgctgaatga    1440
tgggtatgga acttttaaa aaagtacatg cttttatgta tgtatattgc ctatggatat     1500
atgtataaat acaatatgca tcatatattg atataacaag ggttctggaa gggtacacag    1560
aaaacccaca gctcgaagag tggtgacgtc tggggtgggg aagaagggtc tggggg        1616
```

<210> SEQ ID NO 37
<211> LENGTH: 277
<212> TYPE: PRT
<213> ORGANISM: Homo sapiens

<400> SEQUENCE: 37

```
Met Val Arg Leu Pro Leu Gln Cys Val Leu Trp Gly Cys Leu Leu Thr
 1               5                  10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
    65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255
```

-continued

```
Gly Cys Gln Pro Val Thr Gln Glu Asp Gly Lys Glu Ser Arg Ile Ser
            260                 265                 270
Val Gln Glu Arg Gln
        275
```